US007910307B2

(12) United States Patent
Felden

(10) Patent No.: US 7,910,307 B2
(45) Date of Patent: Mar. 22, 2011

(54) EUBACTERIAL TMRNA SEQUENCES AND USES THEREOF

(75) Inventor: Brice Felden, Le Lou du Lac (FR)

(73) Assignee: University of Utah Research Foundation, Salt Lake City, UT (US)

( * ) Notice: Subject to any disclaimer, the term of this patent is extended or adjusted under 35 U.S.C. 154(b) by 267 days.

(21) Appl. No.: 12/163,337

(22) Filed: Jun. 27, 2008

(65) Prior Publication Data

US 2009/0117569 A1 May 7, 2009

Related U.S. Application Data

(62) Division of application No. 11/329,230, filed on Jan. 11, 2006, now Pat. No. 7,611,843, which is a division of application No. 09/958,206, filed as application No. PCT/US00/08988 on Apr. 6, 2000, now Pat. No. 7,115,366.

(60) Provisional application No. 60/128,058, filed on Apr. 7, 1999.

(51) Int. Cl.

| | |
|---|---|
| ***C12Q 1/68*** | (2006.01) |
| ***A01N 43/04*** | (2006.01) |
| ***A61K 31/70*** | (2006.01) |
| ***C07H 21/02*** | (2006.01) |
| ***C07H 21/04*** | (2006.01) |
| ***C12P 19/34*** | (2006.01) |

(52) U.S. Cl. ......... 435/6; 435/91.1; 435/91.2; 514/44 R; 536/23.1; 536/23.7

(58) Field of Classification Search ........................ None
See application file for complete search history.

(56) References Cited

U.S. PATENT DOCUMENTS

2006/0234260 A1 * 10/2006 Griffais et al. .................... 435/6

OTHER PUBLICATIONS

Felden et al., "Eubacterial tmRNAs: everywhere except the alpha-Proteobacteria?" Biochimica et Biophysica Acta 1446:145-148, 1999.

N. Nameki et al., "Three of four pseudoknots in tmRNA are interchangeable and are substitutable with single-stranded RNAs," FEBS Lett 470(3):345-349, Mar. 31, 2000.

N. Nameki et al., "Functional and structural analysis of a pseudoknot upstream of the tag-encoded sequence in *E. coli* tmRNA," J. Mol. Biol 286(3):733-744, Feb. 26, 1999.

W. Schönhuber et al., "Utilization of tmRNA squences for bacterial identification,".MBC Microbiology 2001, 1:20 (online, 8 pages).

K.P. Williams et al., "Phylogenetic analysis of tmRNA secondary structure," RNA 2:1306-1310, 1996.

Zwieb et al., "Survey and Summary, Comparative sequence analysis of tmRNA," Nucleic Acids Research 27(10):2063-2071, 1999.

Huang, C. et al., "Charged tmRNA but not tmRNA-mediated proteolysis is essential for Neisseria gonorrhoeae vitability,"The EMBO Journal, vol 19, No. 5, pp. 1098-1107, 2000, copyright European Molecular Biology Organization.

Ley, B.E. et al., "Eubacterial approach to the diagnosis of bacterial infection," Archives of Disease in Childhood 1997;77:148-149.

* cited by examiner

*Primary Examiner* — Janet Epps-Smith
(74) *Attorney, Agent, or Firm* — Rothwell, Figg, Ernst & Manbeck pc

(57) ABSTRACT

The present invention is directed to eubacterial tmDNA sequences and the corresponding tmRNA sequences. The present invention is further directed to alignments of eubacterial tmDNA sequences and the use of the sequences and sequence alignments for the development of antibacterial drugs. The present invention is also directed to the use of the sequences for the development of diagnostic assays.

6 Claims, 24 Drawing Sheets

```
5'   H1                    H5                       H2
Tab.saccha  *********-**********CGGGGGUAGUAGAGGUAAAAGUAGCGAGC
C.acetobut  *********-***************************************
C.stercora  *********-**********CGGGGUUAU-UGAAGCAAGAGUAGCGGGU
C.perfrige  *********-**********CGGGGGUAAGAUGGGUUUGAUAAGCGAGU
C.lentocel  *********-**********CGGGGGUCACAUCUACUGGGGCAGCCAUC
Hlb.mobili  *********-**********CGGGGAACGUGUUUGCUUGGGAUGCGAGC
Hsp.gestii  *********-**********CGGGGAACGUGUUUGCUUAGGACGCGAGC
Bb.brevis   *********-**********CGGGGAUGG-UAGAGCAUGAGAAGCGAGC
B.subtilis  GGGGACGUU-ACGGAUUCGACAGGGAUGGAUCGAGCUUGAGCUGCGAGC
B.badius    *********-**********CAGGGAUAGUUCGAGCUUGGGCUGCGAGC
B.megateri  ggggacguu-acggauucgacAGGG-UAGUUCGAGCUUAGGUUGCGAGU
B.thermole  *********-**********CGGGGGUAGGUCGAGCUUAAGCGGCGAGC
Eco.fecium  *********-**********CAGGCACAGUUUGAGCUUGAAUUGCGUUU
Eco.faecal  GGGGGCGUU-ACGGAUUCGACAGGCAUAG-UUGAGCUUGAAUUGCGUUU
Stc.pyogen  GGGGUUGUU-ACGGAUUCGACAGGCAUUA-UGAGGCAUGUUUUGCGUCC
Stc.pneumo  GGGGUCGUU-ACGGAUUCGACAGGCAUUA-UGAGGCAUAUUUUGCGACU
Stc.gordon  GGGGUCGUU-ACGGAUUCGACAGGCAUUA-UGAGGCAUAUUUUGCGACU
Stc.mutans  GGGGUCGUU-ACGGAUUCGACAGGCAUUA-UGAGACCUAUUUUGCGACU
Stp.epider  *********-**********CAGGGGUCC-CCGAGCUUAUUAAGCGUGU
Stp.aureuT  GGGGACGUUCAUGGAUUCGACAGGGGUCCCCCGAGCUCAUUAAGCGUGU
L.acidophi  *********-**********CAGGCGUAG-ACCCGCAUUGACUGCGGUU
                                                  PK1
Tab.saccha  CGAGGU--UCCAUCUG-CUCG-UAAA-ACGGUGGAC---UUAAAU
C.acetobut  *********************-*************---******
C.stercora  AGAGGAUUCUCGUUGGCCUCU-UUAA-AAAACGAGA--GCUAAAA
C.perfrige  CGAGGGAAGCAUGGUGCCUCGAUAAUAAAGUAUGCA---UUAAAG
C.lentocel  CGUAGAACGCCGGAGUCUACG-UUAA-AAGCUGGCA---CUUAAA
Hlb.mobili  CGGGUUG--CCGCCAGGACCG-UAAA--AAGGGCGG---AAGGCU
Hsp.gestii  CGGGUUG--CCGCCAGGACCG-UAAA--AAGGGCGG---AAGGCU
Bb.brevis   CGGGGGG--UUGCGGACCUCG-UCAC--CAACGCAA---ACGCCA
B.subtilis  CGAGA-----GGCG-AUCUCG-UAAA---CACGCAC---UUAAAU
B.badius    CGGAG-----GGCCGUCUUCG-U-AC-CAACGCAAACGCCUAAAU
B.megateri  CGAGG-----AGAUGGCCUCG-UUAA--AACAUCAA-CGCCAAUA
B.thermole  CGAGG----GGGACGUCCUCG-UAAA--AACGUCAC---CUAAAG
Eco.fecium  CGUAG----GUUACGUCUACG-UUAAAACGUUACAG---UUAAAU
Eco.faecal  CGUAG----GUUACGGCUACG-UUAAAACGUUACAG---UUAAAU
Stc.pyogen  CAUC---------GGCAGAUG-UAAA---UUGCCAG---UUAAAU
Stc.pneumo  CGU---------GUGGCGACG-UAAA---CGCUCAG---UUAAAU
Stc.gordon  CAUC--------UAGCGGAUG-UAAA---ACGCCAG---UUAAAU
Stc.mutans  CAUC--------UAGCGGAUG-UAAA---ACGCCAG---UUAAAU
Stp.epider  CGGAG-----GGUUGGCUCCG-UCAUCAACACAUUUCGGUUAAAU
Stp.aureus  CGGAG-----GGUUGUCUUCG-UCAUCAACACACACAGUUUAUA-
L.acidophi  CGUAG----GUUACGUCUACG-UAAAAACGUUACAG---UUAAAU
```

FIG. 3A

```
                      ┌─CODING SEQUENCE                                      H4
                      ↓                                                    ┌──────┐
Tab.saccha  AUAAAC gcaaacgauaau--------------uuagcuuagcugcuUAA UA-CAAGCAGC---
C.acetobut  ****** *************_____*****************_***********___
C.stercora  AUAAAC gcaaacaacgauaacuac---------gcuuuagcugcugcgUAA GUAACACGCAGCC--
C.perfrige  AUAAAC gcagaagauaau--------------uuugcauuagcagcuUAA UUUAGCGCUGCU---
C.lentocel  GUAAAC gcugaagauaau--------------uuagcaaucgcugccUAA UA-AGGC-GC----
Hlb.mobili  UUAAUU gccgaagauaac--------------uacgcuuuagcugcuUUA UUGCAGUCUAA----
Hsp.gestii  UUAAUU gccgaagauaac--------------uacgcuuuagcugcuUAA UUGCAGUCUAA----
Bb.brevis   UUAACU ggcaacaaacaa--------------cuuucucucgcugcuUAA UAACCAGUGAG----
B.subtilis  AUAACU ggcaaaacuaacaguuuuaaccaaaacguagcauuagcugccUAA UAAGCGCAGCGA---
B.badius    AUAACU ggcaaaaaagau--------------uuagcuuuagcugccUAA UAUAGGUUCAGCU--
B.megateri  AUAACU ggcaaaucuaacaauaac--------uucgcuuuagcugcaUAA UAGUAGCUUAGC---
B.thermole  AUAACU ggcaaacaaaac--------------uacgcuuuagcugccUAA UUGCUGCAGCUA---
Eco.fecium  AUAACU gcuaaaaacgaaaacaacucu-----uacgcuuuagcugccUAA AAA-CAGUUAGCGUA
Eco.faecal  AUAACU gcuaaaaacgaaaacaauucu-----uucgcuuuagcugccUAA AAACCAGCUAGCGAA
Stc.pyogen  AUAACU gcaaaaaauacaaacucu--------uacgcuuuagcugccUAA AAACCAGCUAGCGU-
Stc.pneumo  AUAACU gcaaaaaauaacacuucu--------uacgcucuagcugccUAA AAACCAGCAGGCGU-
Stc.gordon  AUAACU gcaaaaaauaauacuucu--------uacgcuuuagcugccUAA AAACCAGCGGGCGU-
Stc.mutans  AUAACU gcaaaaaauacaaauucu--------uacgcaguagcugccUAA AAACCAGCCUGUGU-
Stp.epider  AUAACU gacaaaucaaacaauaau--------uucgcaguagcugcgUAA UAGCCACUGC-----
Stp.aureus  AUAACU ggcaaaucaaacaauaau--------uucgcaguagcugccUAA UCGCA-CU-CUGC--
L.acidophi  AUAACU gcaaauaacaaaaauucu--------uacgcauuagcugcuUAA UUUAGCGCAUGCGU-

Tab.saccha  CGUUCAA-CCUU-UGAU-UCCCAC--AUCA-AAGGAUUGGGCGUCG---AUUUAGUGGGG
C.acetobut  ***********_*************_****_***AAUCUGGCGUCG----AGAGCGGGG
C.stercora  CGUCGG-C-CCCGGGGUUCCUGC---GCCUCGGGAUACCGGCGUCA---UCAAGGCAGG
C.perfrige  CAUCCUU--CCU-CAAUUGCCCACG-GUUG-AGAGUAAGGGUGUCAUUUAAAAGUGGGG
C.lentocel  AGUCCU----CCU-AGGUCUUCCGCA-GCCU-AGAUC-AGGGCUUCG---ACUCGCGGAU
Hlb.mobili  CCUCUU-C-UCC-UC-UGUGCUCUCGGUGA-GGAUGUAAGGGGUCA-UUUAAGAGAGCU
Hsp.gestii  CCUCUU-C-UCC-UC-UGUGCUCUCGGUGA-GGAUGUAAGGGGUCA-UUUAAGAGAGCU
Bb.brevis   GCUCUC-CCACU-GCAUCGGCCCGU-GUGC-CGUGGAUAGGGCUCAACUUUAACGGGCU
B.subtilis  GCUCUUC--CUG-ACAU-UGCCUAU-GUGU-CUGU-GAAGAGCACA-UCCAAGUAGGCU
B.badius    GCUCCU--CCCG-CUAU-CGUCCAU-GUAGUCGGGUAAGGGGUCCAAACUUAGUGGACU
B.megateri  GUUCCU--CCCU-CCAU-CGCCCAU-GUGGUAGGGUAAGGGACUCACUUUAAGUGGGCU
B.thermole  GCUCCUC--CCG-CCAU-CGCCCGC-GUGG-CGUUCGAGGGGCUCAUAUGGAGCGGGCU
Eco.fecium  GAUCCU--CUCG-GCAU-CGCCCAU-GUGCUCGAGUAAGGGUCUCAAAUUUAGUGGGAU
Eco.faecal  GAUCCU--CCCG-GCAU-CGCCCAU-GUGCUCGGGUCAGGGUCCUAAUCGAAGUGGGAU
Stc.pyogen  GACUUCU--ACA-AGAU-UGCUUGU-GUCC-UGUU-AGAAGUC-UCAAAAUAGCAAGCU
Stc.pneumo  GACCC--GAUUU-GGAU-UGCUCGU-GUUC-AAUGA-CAGGUCUUAUUAUUAGCGAGAU
Stc.gordon  GACCC--GAUUC-GGAU-UGCUUGU-GUCU-GAUGA-CAGGUCUUAUUAUUAGCAAGCU
Stc.mutans  GAUCAAU--AAC-AAAU-UGCUUGU-GUUU-GUUG-AUUGGUCUUAUUGUUAACAAGCU
Stp.epider  AUCGCC-UAACA-GCAU-CUCCAC-GUGC-UGUUAACGCGAUUCAACCCUAGUAGGAU
Stp.aureus  AUCGCC-UAACA-GCAU-UUCCAU-GUGC-UGUUAACGCGAUUCAACCUUAAUAGGAU
L.acidophi  UGCUCU-UUGUC-GGUU-UACUCGU-GGCU-GACAC-UGAGUAUCA-ACUUAGCGAGUU
                                                                    └──────┘
                                                                       PK2
```

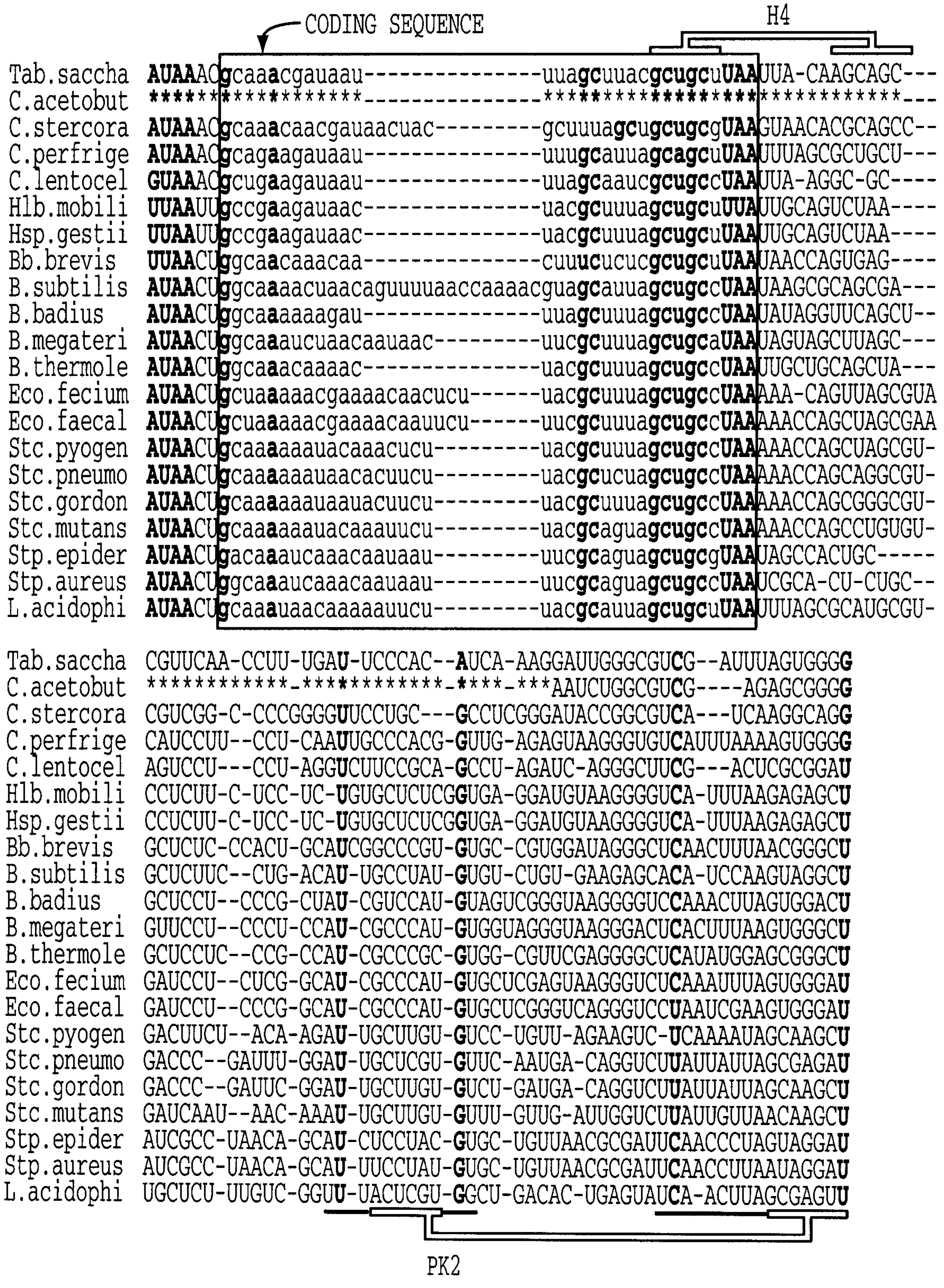

Figure 3C:
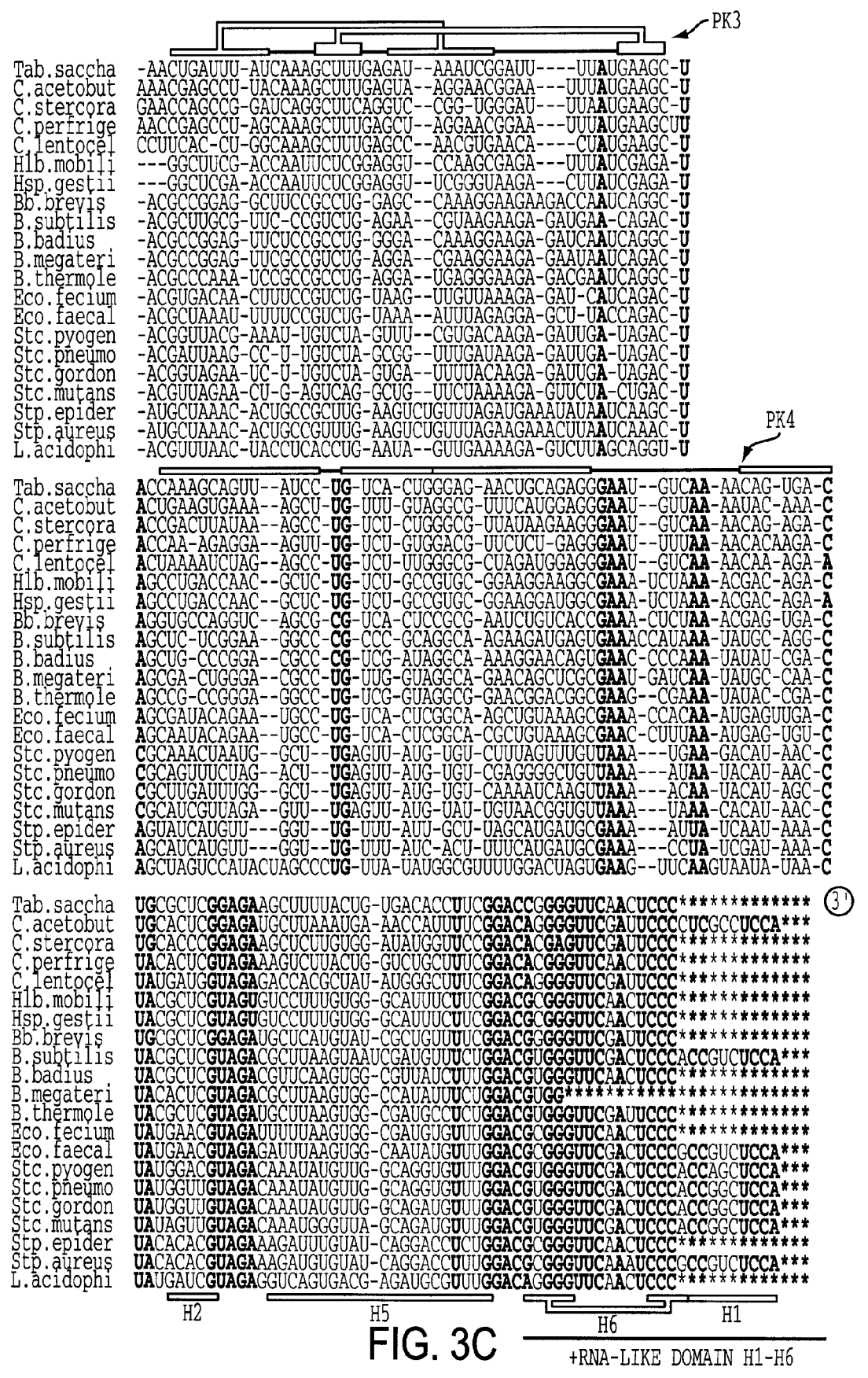

```
Tab.saccha -AACUGAUUU-AUCAAAGCUUUGAGAU--AAAUCGGAUU----UUAUGAAGC-U
C.acetobut AAACGAGCCU-UACAAAGCUUUGAGUA--AGGAACGGAA---UUUAUGAAGC-U
C.stercora GAACCAGCCG-GAUCAGGCUUCAGGUC--CGG-UGGGAU---UUAAUGAAGC-U
C.perfrige AACCGAGCCU-AGCAAAGCUUUGAGCU--AGGAACGGAA---UUUAUGAAGCUU
C.lentocel CCUUCAC-CU-GGCAAAGCUUUGAGCC--AACGUGAACA----CUAUGAAGC-U
Hlb.mobili ---GGCUUCG-ACCAAUUCUCGGAGGU--CCAAGCGAGA---UUUAUCGAGA-U
Hsp.gestii ---GGCUCGA-ACCAAUUCUCGGAGGU--UCGGGUAAGA---CUUAUCGAGA-U
Bb.brevis  -ACGCCGGAG-GCUUCCGCCUG-GAGC--CAAAGGAAGAAGACCAAUCAGGC-U
B.subtilis -ACGCUUGCG-UUC-CCGUCUG-AGAA--CGUAAGAAGA-GAUGAA-CAGAC-U
B.badius   -ACGCCGGAG-UUCUCCGCCUG-GGGA--CAAAGGAAGA-GAUCAAUCAGGC-U
B.megateri -ACGCCGGAG-UUCGCCGUCUG-AGGA--CGAAGGAAGA-GAAUAAUCAGAC-U
B.thermole -ACGCCCAAA-UCCGCCGCCUG-AGGA--UGAGGGAAGA-GACGAAUCAGGC-U
Eco.fecium -ACGUGACAA-CUUUCCGUCUG-UAAG--UUGUUAAAGA-GAU-CAUCAGAC-U
Eco.faecal -ACGCUAAAU-UUUUCCGUCUG-UAAA--AUUUAGAGGA-GCU-UACCAGAC-U
Stc.pyogen -ACGGUUACG-AAAU-UGUCUA-GUUU--CGUGACAAGA-GAUUGA-UAGAC-U
Stc.pneumo -ACGAUUAAG-CC-U-UGUCUA-GCGG--UUUGAUAAGA-GAUUGA-UAGAC-U
Stc.gordon -ACGGUAGAA-UC-U-UGUCUA-GUGA--UUUUACAAGA-GAUUGA-UAGAC-U
Stc.mutans -ACGUUAGAA-CU-G-AGUCAG-GCUG--UUCUAAAAGA-GUUCUA-CUGAC-U
Stp.epider -AUGCUAAAC-ACUGCCGCUUG-AAGUCUGUUUAGAUGAAAUAUAAUCAAGC-U
Stp.aureus -AUGCUAAAC-ACUGCCGUUUG-AAGUCUGUUUAGAAGAAACUUAAUCAAAC-U
L.acidophi -ACGUUUAAC-UACCUCACCUG-AAUA--GUUGAAAAGA-GUCUUAGCAGGU-U
```

PK4

```
Tab.saccha ACCAAAGCAGUU--AUCC-UG-UCA-CUGGGAG-AACUGCAGAGGGAAU--GUCAA-AACAG-UGA-C
C.acetobut ACUGAAGUGAAA--AGCU-UG-UUU-GUAGGCG-UUUCAUGGAGGGAAU--GUUAA-AAUAC-AAA-C
C.stercora ACCGACUUAUAA--AGCC-UG-UCU-CUGGGCG-UUAUAAGAAGGGAAU--GUCAA-AACAG-AGA-C
C.perfrige ACCAA-AGAGGA--AGUU-UG-UCU-GUGGACG-UUCUCU-GAGGGAAU--UUUAA-AACACAAGA-C
C.lentocel ACUAAAAUCUAG--AGCC-UG-UCU-UUGGGCG-CUAGAUGGAGGGAAU--GUCAA-AACAA-AGA-A
Hlb.mobili AGCCUGACCAAC--GCUC-UG-UCU-GCCGUGC-GGAAGGAAGGCGAAA-UCUAAA-ACGAC-AGA-C
Hsp.gestii AGCCUGACCAAC--GCUC-UG-UCU-GCCGUGC-GGAAGGAUGGCGAAA-UCUAAA-ACGAC-AGA-A
Bb.brevis  AGGUGCCAGGUC--AGCG-CG-UCA-CUCCGCG-AAUCUGUCACCGAAA-CUCUAA-ACGAG-UGA-C
B.subtilis AGCUC-UCGGAA--GGCC-CG-CCC-GCAGGCA-AGAAGAUGAGUGAAACCAUAAA-UAUGC-AGG-C
B.badius   AGCUG-CCCGGA--CGCC-CG-UCG-AUAGGCA-AAAGGAACAGUGAAC-CCCAAA-UAUAU-CGA-C
B.megateri AGCGA-CUGGGA--CGCC-UG-UUG-GUAGGCA-GAACAGCUCGCGAAU-GAUCAA-UAUGC-CAA-C
B.thermole AGCCG-CCGGGA--GGCC-UG-UCG-GUAGGCG-GAACGGACGGCGAAG--CGAAA-UAUAC-CGA-C
Eco.fecium AGCGAUACAGAA--UGCC-UG-UCA-CUCGGCA-AGCUGUAAAGCGAAA-CCACAA-AUGAGUUGA-C
Eco.faecal AGCAAUACAGAA--UGCC-UG-UCA-CUCGGCA-CGCUGUAAAGCGAAC-CUUUAA-AUGAG-UGU-C
Stc.pyogen CGCAAACUAAUG--GCU--UGAGUU-AUG-UGU-CUUUAGUUUGUUAAA---UGAA-GACAU-AAC-C
Stc.pneumo CGCAGUUUCUAG--ACU--UGAGUU-AUG-UGU-CGAGGGGCUGUUAAA---AUAA-UACAU-AAC-C
Stc.gordon CGCUUGAUUUGG--GCU--UGAGUU-AUG-UGU-CAAAAUCAAGUUAAA---ACAA-UACAU-AGC-C
Stc.mutans CGCAUCGUUAGA--GUU--UGAGUU-AUG-UAU-UGUAACGGUGUUAAA---UAAA-CACAU-AAC-C
Stp.epider AGUAUCAUGUU---GGU--UG-UUU-AUU-GCU-UAGCAUGAUGCGAAA---AUUA-UCAAU-AAA-C
Stp.aureus AGCAUCAUGUU---GGU--UG-UUU-AUC-ACU-UUUCAUGAUGCGAAA---CCUA-UCGAU-AAA-C
L.acidophi AGCUAGUCCAUACUAGCCCUG-UUA-UAUGGCGUUUUGGACUAGUGAAG--UUCAAGUAAUA-UAA-C
```

```
Tab.saccha UGCGCUCGGAGAAGCUUUUACUG-UGACACCUUCGGACCGGGGUUCAACUCCC************* 3'
C.acetobut UGCACUCGGAGAUGCUUAAAUGA-AACCAUUUUCGGACAGGGGUUCGAUUCCCCUCGCCUCCA***
C.stercora UGCACCCGGAGAAGCUCUUGUGG-AUAUGGUUCCGGACACGAGUUCGAUUCCC*************
C.perfrige UACACUCGUAGAAAGUCUUACUG-GUCUGCUUUCGGACACGGGUUCAACUCCC*************
C.lentocel UAUGAUGGUAGAGACCACGCUAU-AUGGGCUUUCGGACAGGGGUUCGAUUCCC*************
Hlb.mobili UACGCUCGUAGUGUCCUUUGUGG-GCAUUUCUUCGGACGCGGGUUCAACUCCC*************
Hsp.gestii UACGCUCGUAGUGUCCUUUGUGG-GCAUUUCUUCGGACGCGGGUUCAACUCCC*************
Bb.brevis  UGCGCUCGGAGAUGCUCAUGUAU-CGCUGUUUUCGGACGGGGGUUCGAUUCCC*************
B.subtilis UACGCUCGUAGACGCUUAAGUAAUCGAUGUUUCUGGACGUGGGUUCGACUCCCACCGUCUCCA***
B.badius   UACGCUCGUAGACGUUCAAGUGG-CGUUAUCUUUGGACGUGGGUUCAACUCCC*************
B.megateri UACACUCGUAGACGCUUAAGUGG-CCAUAUUUCUGGACGUGG************************
B.thermole UACGCUCGUAGAUGCUUAAGUGG-CGAUGCCUCUGGACGUGGGUUCGAUUCCC*************
Eco.fecium UAUGAACGUAGAUUUUUAAGUGG-CGAUGUGUUUGGACGCGGGUUCAACUCCC*************
Eco.faecal UAUGAACGUAGAGAUUUAAGUGG-CAAUAUGUUUGGACGCGGGUUCGACUCCCGCCGUCUCCA***
Stc.pyogen UAUGGACGUAGACAAAUAUGUUG-GCAGGUGUUUGGACGUGGGUUCGACUCCCACCAGCUCCA***
Stc.pneumo UAUGGUUGUAGACAAAUAUGUUG-GCAGGUGUUUGGACGUGGGUUCGACUCCCACCGGCUCCA***
Stc.gordon UAUGGUUGUAGACAAAUAUGUUG-GCAGAUGUUUGGACGUGGGUUCGACUCCCACCGGCUCCA***
Stc.mutans UAUAGUUGUAGACAAAUGGGUUA-GCAGAUGUUUGGACGUGGGUUCGACUCCCACCGGCUCCA***
Stp.epider UACACACGUAGAAAGAUUUGUAU-CAGGACCUCUGGACGCGGGUUCAACUCCC*************
Stp.aureus UACACACGUAGAAAGAUGUGUAU-CAGGACCUUUGGACGCGGGUUCAAAUCCCGCCGUCUCCA***
L.acidophi UAUGAUCGUAGAGGUCAGUGACG-AGAUGCGUUUGGACAGGGGUUCAACUCCC*************
```

+RNA-LIKE DOMAIN H1-H6

```
Aqf.aeolic  CG-GGCUACUCGGU--CGCACGGG-GCUGAGUAGCUGACACCUAACCCGUGCU
Tt.maritim  A--CCGAUUCAG--UUCGCCUUCCGGCCUGAAUCGGGAAAACUCAGGAAGGCU
Tt.neapoli  A--CCGAUCUGGGCUCCGCCUUCCGGCCCGGAUCGGGAAGGUUCAGGAAGGCU
T.thermoph  A--GCCCGGGGC--CACGCCCUCU--AACCCCGGGCGAAGCUUGAAGGGGGCU
D.radiodur  A--GCCC-AGGC--GAUUCUCCAU--AGCCGACGGCGAAACU-UUAUGGAGCU
D.proteoly  A--GCUU-AGGU--GAGGUUCCAU--AGCCAAAAGUGAAACC-AAAUGGAAAU    PK3
Tmc.roseum  GCCCCUGGCCCA--AGCGCCGGUG---CGGGCCAGGUCAAGCGUGAUCCGGCU
Ctb.proteo  GC-UCUUAAGCAG--UGGCACCAG--CUGUUUAAGGGUGAAAAGAGUGGUGCU
Her.aurant  CGCUCCCCUAGUU--AUGUCUGUG--GGCUAGGGG--CUAAGAUUAACAGGCU
Tdb.commun  UU-GGGAGGCUUAA-UCGGUGGGG-UUAAGCCUCCCGAGAUUACAUCCCACCU
Ver.spinos  G--GCCAAAAGAGC-GGGCGACCG-GC-CCCAAGGCGAGAUCUACAGGCCGCU
Dcg.thermo  GCCCCUUCCG-----ACUCCCCUA-----AGGAAGGGAAAGA-UGUAGGGGAU

Aqf.aeolic  A--CCCUC-GGGGAGCUUGCCCGUGGGCGACCC-GAGGG--GAAAUCC-UGAACACGGGC
Tt.maritim  G-UGGGAGAGGACACCCUGCCCGUGGGAGGUCC-CUCCC--GAGAGCG-AAAACACGGGC
Tt.neapoli  G-UGGGAAGCGACACCCUGCCCGUGGGGGGUC-CUUCCC--GAGACAC-GAAACACGGGC
T.thermoph  C-GCUCCUGGCC--GCCCGUCCGCGGGCCAAGCCAGGAG--GACACGC-GAAACGCGGAC
D.radiodur  A-CGGCCUGCGAGAACCUGCCCACUGGUGAGCGCCGGCCC-GACAAUC-AAACAGUGGGA
D.proteoly  A-AGGCGGACGGCAGCCUGUUUGCUGGCAGCCCAGGCCC--GACAAUU-UAAGAGCAGAC    PK4
Tmc.roseum  C-GGCUGACCGGGAUCCUGUCGGUGGGAGCCUGG-CAGC--GACAGUA--GAACACCGAC
Ctb.proteo  G--GGCAGUGCGGUU-GGGCU-UCCUGGGCUGCACUGUC--GAGACUU-CACAGGAGGGC
Her.aurant  G-GUCGUGGC-CCGCUUUGUCUAUCGGGUGGUGCACCGAU-AAGAUUU-AAUCAAUAGAC
Tdb.commun  G--GUAGGGUUGCUUGGUGCCUGUGACAAGCA-CCCUAC--GAGAUUU--UCCCACAGGC
Ver.spinos  G--GAUGGACGGCAUCCUGGCAGUAGGAGGCUGGACAUC--GAGAUCA--AAUNAUUGCC
Dcg.thermo  AGGUGCUUACAGAAUCCUGCGGGAGGGAGUCUGUAAGUGCCGAAAAGUUAAAACUCCCGC

Aqf.aeolic  UAAGCC-UGUAGAGCCUCGGAUGUGGCCGCCGUCCUCGGACGCGGGUUCGAUUCCCGCCGCCUCCACCA
Tt.maritim  UGCGCU-CGGAGAAGCCCAGGGG---CCUCCAUCUUCGGACGGGGGUUCGAAUCCCCCCGCCUCCACCA
Tt.neapoli  UGCGCU-CGGAGAAGCCCAGGGG---CCUCCAUCUUCGGACGGGGGUUCGAUUCCCGCCGCCUCCA***
T.thermoph  UACGCG-CGUAGAGGCcacgccc---cggcgaccuucggacgggggguucgauucccccccaccuccacca
D.radiodur  UACACA-CGUAGACGCA-CGCUG---GACGGACCUUUGGACGGCGGUUCGACUCCGCCCACCUCCACCA
D.proteoly  UACGCA-CGUAGAUGCA-CGCUG---GAUGGACCUUUGGACGGCGGUUCGAUUCCCGCCGCCU-CACCA
Tmc.roseum  UAAGCC-UGUAGCAUAUCCUCGG---CUGAACGCUCUGGACGGGGGUUCAACUCCCGCCAGCUCCACCA
Ctb.proteo  UAAGCC-UGUAGACGCGAAAGGU---GGCGGCUCGUCGGACGCGGGUUCGAUUCCCGCCGCCUCCACCA
Her.aurant  UACGCU-UGUAGAUGCUUGCGGU----UUAACUUUUUGGACGCGGGUUCGAUUCCCGCCGCCUCCACCA
Tdb.commun  UAAGCC-UGUAGCGGUUUAAUCU---GAACUAUCUCCGGACGCGGGUUCGAUUCCCGCCGCCUCCACCA
Ver.spinos  UGAGCA-UGGAGACGCUUUCAUA-----AAGGNGUUCGGACAGGG************************
Dcg.thermo  UAAGCU-UGUAGAGGCUUUUGAU---UCUUGCUCUCUGGACGCGGGUUCGAUUCCCGCCGCCUCCACCA  3'
              H2            H5                       H6          H1
```

+RNA-LIKE DOMAIN H1-H6

FIG. 4B

```
Alc.faecal  GCAGUGUUAU-UUACAAAGAAU--C-GAAUCGGUCUGCGCCACGAAGUCCGGUUCUAAAA-CUUAGUGGAU
Alc.eutrop  GCGAGGUCAU-UUACGUCAGAU--A-AGCUCCGGAAGGGUCACGAAGCCGGGGACGAAAA-CCUAGUGACU
Ral.picket  GCGAGGUCAU-UUACGUCAGAU--A-AGCUUUAGGUGAGUCACGGGCCUAGAGACGAAAA-CUUAGUGAAU
Nis.gonorr  GCAACGUCAUCUUACAUUGACU--G-GUUUCCAGCCGGGUUACUUGGCAGGAAAUAAGACUUAAGGUAACU
Nis.meninS  GCAACGUCAUCUUACAUUGACU--G-GUUUCCUGCCGGGUUAUUUGGCAGGAAAUGAGAUUUAAGGUAACU
Chb.violac  GUAGUGUCACUCUACAUCUGCU--A-GUGCUGUUCCGGGUUACUUGGUUCAGUGCGAAAUAAUAGGUAACU
Nms.cryoto  GCAGAGUCAU-UAG-CAAGGAU--C-GCGUUCUGUAGGGUCACUUUACAGAACGUUAAACAAUAGGUGACU   PK3
Mtb.glycog  GCAGCGUCAU-UAAGAGAGGAU--C-GUGCGAUAUUGGGUUACUUAAUAUCGUAUUAAAUCCAAGGUAACU
Ps.testost  GCAAGGGAAU-UUUCAUUAGCU--G-GCUGGAUACCGGGCUUCUUGGUAUUUGGCGAGAUUUUAGGAAGCU
Vx.paradox  GCAAGGAUAA-CUACAUGGGCU--G-GCUCCGAUCCGGGUACCUUGGGUCGGGGCGAGAAAAUAGGGUACU
Hph.paller  GCAAGGUAAU-UUACAUCGGCU--G-GUUCUGCGUCGGGCACCUUGGCGCAGGAUGAGAUUCAAGGAUGCU
Brd.pertus  GCAGCGACAU-UCACAAGGAAU--C-GCCACCGCUGGGGUCACA-CGGCGUUGGUUUAAA-UUACGUGAAU
                PK2

Alc.faecal  CGCCAAGG-AAAGGCCUGUCA-AUUGGCAUAGUCCAAGGUUAAAACUUAAAAUUAAU-UGAC
Alc.eutrop  CGCCGUCG-UAGAGCGUGUUC-GUCCGCGAUG-CGCCGGUUAAAU---CAAA-UGACAGAAC
Ral.picket  CGCCGUCG-UAGAGCGUGUUC-GUCCGCGAUG-CGGCGGUUAAAU---CAAA-UGACAGAAC
Nis.gonorr  GGUUUCCA-AAAGGCCUGUUG-GUCGGCAUGA-UGGAAAUAAGAUUUUCAAAUAGACACAAC
Nis.meninS  GGUUUCCA-AAAGGCCUGUUG-GUCGGCAUGA-UGGAAAUAAGAUUUUCAAAUAGACACAAC
Chb.violac  CGCCAAAGUCCA-GCCUGUCC-GUCGGCGUGG-CAGAGGUUAAAUC--CAAA-UGACACGAC
Nms.cryoto  CGCCUGCC-AUCAGCCCGCCA-GCUGGCGGUU-GUCAGGUUAAAU---UAAA-GAGCAUGGC   PK4
Mtb.glycog  CGCCUGCU-GUUUGCUUGCUC-GUUGGUGAGC-AUCAGGUUAAAU---CAAA-CAACACAGC
Ps.testost  GGCUACCCAAGCAGCGUGUGC-CUGCGGGGUUUGGGUGGCGAGAUU--UAAA-ACAGAGCAC
Vx.paradox  GGCGUCCGGUUUAGCGUGUGA-CUGCGCGACUCCGGAAGCGAGACU--CAAA-ACAGAUCAC
Hph.paller  GGCUUCCCGUUUAGCGUGCCA-CUGCGCGACUCGGGCGGCGAGACC--CAAA-UCAGACGGC
Brd.pertus  CGCCCUGG-UCCGGCCCGUCG-AUCGGCUAAGUCCAGGGUUAAAUC--CAAAUAGAU-CGAC

Alc.faecal  UACACAUGUAGAACUGUCUGUGGACGGCUUGCGGACGGGGGUUCGAUUCCC*************
Alc.eutrop  UAAGUAUGUAGAACUCUCUGUGGAGGGCUUACGGACGCGGGUUCGAUUCCCGCCGGCUCCACCA
Ral.picket  UAAGUAUGUAGAACUCUCUGUGGAGGGCUUGCGGACGCGGGUUCGAUUCCC*************
Nis.gonorr  UAAGUAUGUAGAACGCUUUGUAGAGGACUUUCGGACGGGGGUUCGAUUCCCCCCGCCUCCACCA
Nis.meninS  UAAGUAUGUAGAACGCUUUGUAGAGGACUUUCGGACGGGGGUUCGAUUCCCCCCGCCUCCACCA
Chb.violac  UAAGUAUGUAGAACUCACUGUAGAGGACUUUCGGACGCGGGUUCAACUCCC*************
Nms.cryoto  UAAGUAUGUAGAACUGUCUGUAGAGGACUUGCGGACGCGGGUUCAACUCCC*************
Mtb.glycog  UAAGUAUGUAGAACUGUCUGUGGAGGGCUUGCGGACGGGGGUUCGAUUCCC*************
Ps.testost  UAAACAUGUAGAUCUGUCCGGCGAAGGCUUACGGACGCGGGUUCAAUUCCCGCCGGCUCCA***
Vx.paradox  UAAACAUGUAGAACUGCGCGAUGAAGGCUUGCGGACGGGGGUUCAACUCCC*************
Hph.paller  UACACAUGUAGAACUGCUCGAAAAAGGCUUGCGGACGGGGGUUCAACUCCC*************
Brd.pertus  UAAGCAUGUAGAACUGGUUGCGGAGGGCUUGCGGACGGGGGUUCAAUUCCCCCCGGCUCCACCA  3'
              H2        H5                     H6               H1
```

FIG. 9B

```
5'    H1                            H5                H2
Leg.pneumo  ********************CGUGGGUUGCAAAACCGGAAGUGCAUGC
Chr.vinosu  ********************CGUGGGUCGCGAAACCUAAGGUGCAUGC
Dcb.nodosu  **********************************CUCGAGGUGCAUGU
Ps.aerugin  GGGGCCGAUU-AGGAUUCGACGCCGGUAACAAAACUUGAGGGGCAUGC
Ps.fluores  ********************CGCCGGUUGCGAACCUUUAGGUGCAUGC
Mar.hydroc  ********************CGCCGGUGACGAACCCUUGGGUGCAUGC
Shw.putref  GGGGGCGAUUCUGGAUUCGACAGGAUUCACGAAACCCUGGGAGCAUGC
Psm.halopl  ********************CGGAAUUCAAGAAGCCCGAGGUGCAUGU
Ae.salmoni  ********************CAAGAUUCACGAAACCCAAGGUGCAUGC
S.typhimur  GGGGCUGAUUCUGGAUUCGACGGGAUUUGCGAAACCCAAGGUGCAUGC
E.coli      GGGGCUGAUUCUGGAUUCGACGGGAUUUGCGAAACCCAAGGUGCAUGC
Yer.pestis  GGGGCUGAUUCUGGAUUCGACGGGAUUCGCGAAACCCAAGGUGCAUGC
V.cholerae  GGGGCUGAUUCAGGAUUCGACGGGAAUUUUGCAGUCUGAGGUGCAUGC
H.influenz  GGGGCUGAUUCUGGAUUCGACGGGAUUAGCGAAGCCCAAGGUGCACGU
H.actinomy  GGGGCUGAUUCUGGAUUCGACGGGAUUAGCGAAGCCCGAAGUGCACGU

                          PK1
Leg.pneumo  CGAG-AAGGAGAUC-UCUCGUAAAUA-AGA-CUCAAUUA-AAU
Chr.vinosu  CGAG-GUGCGGUUGACCUCGUAAAAC--CCUCCGCAAA--CUU
Dcb.nodosu  CGAG-AAUGAGAGAAUCUCGUUAAAU--ACUUUCAAAA--CUU
Ps.aerugin  CGAGCUGGUAGCAGAACUCGUAAAUUCGCUGCUGCAAA--CUU
Ps.fluores  CGAGUUGGUAACAGAACUCGUAAAUCCACUGUUGCAACUUUCU
Mar.hydroc  CGAGAUGGCAGCGAAUCUCGUAAAUCCAAAGCUGCAAC--GUA
Shw.putref  CGAG-GGGCGGUUGGCCUCGUAAA----AAGCCGCAAA--GUU
Psm.halopl  CGAG-GUGCGGUUUGCCUCGUAAAA---AAGCCGCAAUU-UAA
Ae.salmoni  CGAG-GUGCGGUAGGCCUCGUUAAC---AAACCGCAAA--AAA
S.typhimur  CGAG-GGGCGGUUGGCCUCGUAAA----AAGCCGCAAA--AAA
E.coli      CGAG-GGGCGGUUGGCCUCGUAAA----AAGCCGCAAA---AA
Yer.pestis  CGAG-GUGCGGUG-GCCUCGUAAA----AAACCGCAAA-AAAA
V.cholerae  CGAG-GUGCGGUAGGCCUCGUUAAC---AAACCGCAAA--AAA
H.influenz  CGAG-GUGCGGUAGGCCUCGUAAAU---AAACCGCAAA--AAA
H.actinomy  CGAG-GUGCGGUAGGCCUCGUAAAU---AAACCGCAAA--AAA     CODING SEQUENCE

Leg.pneumo  A-UAAAUgcaaacgaugaaaacuuugcugguggggaagcuaucgcugccUAA-----UAAGCACUUU
Chr.vinosu  A-UAGUUgccaacgacgacaacuac------------gcucucgcugcuUAA-----UCCCAGCGGG
Dcb.nodosu  A-UAGUUgcaaacgacgacaacuac------------gcuuuagcggcuUAA-----UUCCCGCUUU
Ps.aerugin  A-UAGUUgccaacgacgacaacuac------------gcucuagcugcuUAA------UGCGGCUAG
Ps.fluores  A-UAGUUgccaaugacgaaaccuac---ggggaauacgcucucgcugcgUAA-------GCAGCCUU
Mar.hydroc  A-UAGUCgcaaacgacgaaaacuac------------gcacuggcggcgUAA---GCCGUU-CCAGU
Shw.putref  A-UAGUUgcaaacgacgauaacuac------------gcucuagccgcuUAA------UGCCGCUAG
Psm.halopl  AGUAAUCgcaaacgacgauaacuac------------ucucuagcagcuUAG------GCUGGCUAG
Ae.salmoni  A-UAGUCgcaaacgacgaaaacuac------------gcacuagcagcuUAAUAACCUGCAUAGAGC
S.typhimur  A-UAGUCgcaaacgacgaaaccuac------------gcuuuagcagcuUAAUAACCUGCUUAGAGC
E.coli      A-UAGUCgcaaacgacgaaaacuac------------gcuuuagcagcuUAAUAACCUGCUUAGAGC
Yer.pestis  A-UAGUUgcaaacgacgaaaacuac------------gcacuagcagcuUAAUAACCUGCUUAGAGC
V.cholerae  A-UAGUCgcaaacgacgaaaacuac------------gcacuagcagcuUAAUACCCUGCUCAGAGC
H.influenz  A-UACUCgcaaacgacgaacaauac------------gcuuuagcagcuUAAUAACCUGCAUUUAGC
H.actinomy  A-UAGUCgcaaacgacgaacaauac------------gcuuuagcagcuUAAUAACCUGCCUUUAGC
                                                                  H4
```

FIG. 10A

```
Leg.pneumo   AGUUAAACCAUCACUGUGUACUGGCCAAUAAACCCAGUAUC
Chr.vinosu
Dcb.nodosu
Ps.aerugin
Ps.fluores   AGCCCUUCCCUCCUGGUACCUUCGGGUCCAG
Mar.hydroc
Shw.putref
Psm.halopl
Ae.salmoni
S.typhimur
E.coli
Yer.pestis
V.cholerae
H.influenz
H.actinomy

Leg.pneumo   CCGUUCG-ACCGAGCCC--GCUUAUC-GGUAUCGAA-------UCAACGGUCAU-AAGAGAU-AAGCU
Chr.vinosu   CCUCUGA-CCGUCACUU--GCCUGUGGGCGGCGGAUU------CCAGGGGUAAC-CUCACAC-AGGAU
Dcb.nodosu   CGCUUAC-CUAGAUUU---GUCUGUGGGUUUACC---------GUAAGCGACAU--UAACAC-AGAAU
Ps.aerugin   CAGUCGC-UAGGGGAU---GCCUGUAAACCCGAAA---------CGACUGUCAG-AUAGAAC-AGGAU
Ps.fluores   CAAUCAU-CAGGGGAU---GUCUGUAAACCCAAAG---------UGAUUGUCAU-AUAGAAC-AGAAU
Mar.hydroc   CGUCCUG-GCUGAGGC---GCCUAUAACUCAGUAGCAACAUCCCAGGACGUCAU-CGCUUAU-AGGCU
Shw.putref   CCAUCUA-CCACACGCUUUGCACAUGGGCAGUGGAUU-------UGAUGGUCAU-CUCACAUCGUGCU
Psm.halopl   CGCUCCU-UCCAUGUAU--UCUUGUG-GACUGGAUUUU------GGAGUGUCACCCUAACAC-CUGAU
Ae.salmoni   CCUUCUA-CCCUAGCUU--GCCUGUGUCCUAGGGAAUC------GGAAGGUCAU-CCUUCAC-AGGAU
S.typhimur   CCUCUCU-CCCUAGCCUCCGCUCUUAGGACGGGGAUCA-----AGAGAGGUCAAACCCAAAA-GAGAU
E.coli       CCUCUCU-CCCUAGCCUCCGCUCUUAGGACGGGGAUCA-----AGAGAGGUCAAACCCAAAA-GAGAU
Yer.pestis   CCUCUCU-CCCUAGCCUCCGCUCUUAGGACGGGGAUCA-----AGAGAGGUCAAACCUAAAA-GAGCU
V.cholerae   CCUUCCU-CCCUAGCUUCCGCUUGUAAGACGGGGAAAUC----AGGAAGGUCAAACCAAAUC-AAGCU
H.influenz   CUUCGCG-CUCCAGCUUCCGCUCGUAAGACGGGGAUAA-----CGCGGAGUCAAACCAAAAC-GAGAU
H.actinomy   CUUCGCU-CCCCAGCUUCCGCUCGUAAGACGGGGAUAA-----AGCGGAGUCAAACCAAAAC-GAGAU
```

```
Leg.pneumo  -AGCG-UCCU-AAUCU--AUCCC-GGGUU-AUGG-CGCGAAA-CU-CA--GGGAAU
Chr.vinosu  -CGUG-GUGA-CGGGA--GUCCG-GACCU-GAUC-CACUAAAACC-UA-ACGGAAU
Dcb.nodosu  -CGCU-GGUU-AACG--CGUCCGC-UGUU-AAUC-GGUUAAA-UU-AA-GCGGAAU
Ps.aerugin  -CGCC-GCCA-AGUU--CGCUGUA-GACG-UAAC-GGCUAAAACU-CA-UACAGCU
Ps.fluores  -CGCC-GUGC-AGUA--CGUUGUG-GACG-AAGC-GGCUAAAACU-UA-CACAACU
Mar.hydroc  GCUCC-GUUC-ACCAG-AGCUCA-CUGGU-GUUC-GGCUAAG-AU-UA-AAGAGCU
Shw.putref  -AGCGAGGGA-ACCC--UGUCUGG-GGGU-GAAC-CGCGAAACAG-UA-CCGGACU
Psm.halopl  -CGCGACGGA-AACCC-UGGCCG-GGGUU-GAAG-CGUUAAAACU-AA-GCGGCCU
Ae.salmoni  -CGUG-UGGA-AGUCC-UGCUCG-GGGCG-GAAG-CAUUAAAACC-AA-UCGAGCU
S.typhimur  -CGCG-CGGA-UGCCC-UGCCUG-GGGUU-GAAG-CGUUAAAACG-AA-UCAGGCU
E.coli      -CGCG-UGGA-AGCCC-UGCCUG-GGGUU-GAAG-CGUUAAAACUUAA-UCAGGCU
Yer.pestis  -CGUG-UGGA-AACCU-UGCCUG-GGGUG-GAAG-CAUUAAAACU-AA-UCAGGAU
V.cholerae  -GGCG-UGGA-UUCCCCCACCUGA-GGGAUGAAG-CGCGAGAUCU-AAUUCAGGUU
H.influenz  -CGUG-UGGA-AGCCACCGUUUGA-GGAUCGAAG-CACUAAAUUG-AA-UCAAACU
H.actinomy  -CGUG-UGGA-AGCCACCGUUUGA-GGAUCGAAG-CAUUAAAUUA-AA-UCAAAGU
```

```
Leg.pneumo  CGCUGUGUAU-CAUCCUGCCC-GUCGGAGGAGCCACAGUUAAAUUCAAAAGACAAGGC--
Chr.vinosu  CGCCGACUGAUCGCCCUGCCC-UUCGGCGGCAGAAGGCUAAAAACAAUAGAGUGGGC--
Dcb.nodosu  CGCUUGUAAA-AUGCCUGAGC-GUUGGCUGUUUAUGAGUUAAACCUAAUUAACUGCUC--
Ps.aerugin  CGCUCCAAGC--ACCCUGCCA-CUCGGCGGCGCGGAGUUAA-CUCAGUAGAGCUGGC--
Ps.fluores  CGCCCAAAGC--ACCCUGCCC-GUCGGGUCGCUGAGGGUUAA-CUUAAUAGACACGGC--
Mar.hydroc  CGCCUCUUGC--ACCCUGACC-UUCGGGUCGCUUGAGGUUAA-AUCAAUAGAA-GGACAC
Shw.putref  CACCGUGUGG-GAUCCUGUCU-UUCGGAGUUCAAACGGUUAA-ACAAUA-GAA-AGAC--
Psm.halopl  CGCCUUUAUC-UACCGUGUUU-GUCCGGGAUUUAAAGGUUAA-UUAAAU-GACAAUAC--   PK4
Ae.salmoni  AGUCAAUUCG-UGGCGUGUCU-CUCCGCAGCGGGUUGGCGAA-UGUAAA-GAG-UGAC--
S.typhimur  AGUCUGGUAG-UGGCGUGUCC-GUCCGCAGGUGCCAGGCGAA-UGUAAA-GAC-UGAC--
E.coli      AGUUUGUUAG-UGGCGUGUCC-GUCCGCAGCUGGCAAGCGAA-UGUAAA-GAC-UGAC--
Yer.pestis  AGUUUGUCAG-UAGCGUGUCC-AUCCGCAGCUGGCCGGCGAA-UGUAAU-GAUUGGAC--
V.cholerae  AGCCAUUCGU-UAGCGUGUCG-GUUCGCAGGCG-GUGGUGAA-AUUAAA-GAU-CGAC--
H.influenz  AGCUUAAGUU-UAGCGUGUCU-GUCCGCA-UGCUUAAGUGAA-AUUAAA-GACGAGAC--
H.actinomy  AGCUUAAUUG-UCGCGUGUCC-GUCAGCA-GGAUUAAGUGAA-UUUAAA-GACCGGAC--
```

```
Leg.pneumo  UAUGCAUGUAGAGCUAAAGGCAGAGGACUUGCGGACGCGG************************
Chr.vinosu  UAAGCAUGUAGGACCGAGGGCAGAGGGCUUGCGGACGCGG************************
Dcb.nodosu  UAAACAUGUAGUACCAAAAGUUAAGGAUUCGCGGACGGGGGUUCAAAUCCCCCCGCCUCCACCA
Ps.aerugin  UAAGCAUGUAGAACCGAUAGCGGAGAGCUGGCGGACGGGGGUUCAAAUCCCCCCGGCUCCACCA
Ps.fluores  UACGCAUGUAGUACCGACAGCAGAGUACUGGCGGACGGGG************************
Mar.hydroc  UAAGCAUGUAGACCUCAAGGCCUAGUGCUGGCGGACGCGG************************
Shw.putref  UAAGCAUGUAGCGCCUUGGAUGUAGGUUUUCUGGACGCGGGUUCAAGUCCCGCCGCCUCCACCA
Psm.halopl  UAAACAUGUAGUACCGACGGUCGAGGCUUUUCGGACGGGG************************
Ae.salmoni  UAAGCAUGUAGUACCGAGGAUGUAGUAAUUUUGGACGGGG************************
S.typhimur  UAAGCAUGUAGUACCGAGGAUGUAGGAAUUUCGGACGCGGGUUCAACUCCCGCCAGCUCCACCA
E.coli      UAAGCAUGUAGUACCGAGGAUGUAGGAAUUUCGGACGCGGGUUCAACUCCCGCCAGCUCCACCA
Yer.pestis  UAAGCAUGUAGUGCCGACGGUGUAGUAAUUUCGGACGGGGGUUCAAAUCCCCCCAGCUCCACCA
V.cholerae  UAAGCAUGUAGUACCAAAGAUGAAUGGUUUUCGGACGGGGGUUCAACUCCCCCCAGCUCCACCA
H.influenz  UAAACGUGUAGUACUGAAGGUAGAGUAAUUUCGGACGGGGGUUCAACUCCCCCCAGCUCCACCA
H.actinomy  UAAACGUGUAGUGCUAACGGCAGAGGAAUUUCGGACGGGGGUUCAACUCCCCCCAGCUCCACCA  3'
```

EUBACTERIAL TMRNA SEQUENCES AND USES THEREOF

CROSS-REFERENCE TO RELATED APPLICATIONS

The present application is division of U.S. patent application Ser. No. 11/329,230 filed on 11 Jan. 2006, which in turn in a division of U.S. patent application Ser. No. 09/958,206 filed on 20 Feb. 2002, now U.S. Pat. No. 7,115,366, which in turn is a national stage filing under 35 U.S.C. §371 of International patent application No. PCT/US00/08988 filed on 6 Apr. 2000, which in turn is related to and claims priority under 35 U.S.C. §119(e) to U.S. provisional patent application Ser. No. 60/128,058 filed on 7 Apr. 1999. Each of these applications is incorporated herein by reference.

This application was made with Government support under Grant No. GM 48152, funded by the National Institutes of Health, Bethesda, Md. The Government has certain rights in this invention.

BACKGROUND OF THE INVENTION

The present invention is directed to eubacterial tmDNA sequences and the corresponding tmRNA sequences. The present invention is further directed to alignments of eubacterial tmDNA sequences and use of the sequences and sequence alignments for the development of antibacterial drugs. The present invention is also directed to the use of the sequences for the development of diagnostic assays.

The publications and other materials used herein to illuminate the background of the invention or provide additional details respecting the practice are incorporated by reference, and for convenience are respectively grouped in the appended List of References.

Eubacterial tmRNAs (10Sa RNAs) are unique since they function, at least in *E. coli*, both as tRNA and as mRNA (for a review, see Muto et al., 1998). These ≈360±10% nucleotide RNAs are charged with alanine at their 3'-ends (Komine et al., 1994; Ushida et al., 1994) and also have a short reading frame coding for 9 to 27 amino acids depending on the bacterial species. *E. coli* tmRNA mediates recycling of ribosomes stalled at the end of terminatorless mRNAs, via a trans-translation process (Tu et al., 1995; Keiler et al., 1996; Himeno et al., 1997). In *E. coli*, this amino acid tag is co-translationally added to polypeptides synthesized from mRNAs lacking a termination codon, and the added 11 amino acid C-terminal tag makes the protein a target for specific proteolysis (Keiler et al., 1996).

Structural analyses based on phylogenetic (Felden, et al., 1996; Williams and Bartel, 1996) and probing (Felden et al., 1997; Hickerson et al., 1998) data have led to a compact secondary structure model encompassing 6 helices and 4 pseudoknots. tmRNAs have some structural similarities with canonical tRNAs, especially with tRNA acceptor branches. *E. coli* tmRNA contains two modified nucleosides, 5-methyluridine and pseudouridine, located in the tRNA-like domain of the molecule, in a seven-nucleotide loop mimicking the conserved sequence of T loops in canonical tRNAs (Felden et al., 1998).

Fifty-three tmRNA sequences are now known from both experimental data and Blast searches on sequenced genomes (summarized in Williams, 1999; Wower and Zwieb, 1999). These sequences cover only 10 phyla, less than one third of the known bacterial taxa. It is desired to determine additional tmRNA sequences and to use the tmRNA sequences for drug development.

SUMMARY OF THE INVENTION

The present invention relates to eubacterial tmDNA sequences and the corresponding tmRNA sequences. The present invention further relates to alignments of eubacterial tmDNA sequences and use of the sequences and sequence alignments for the development of antibacterial drugs.

In one aspect of the present invention, an extensive phylogenetic analysis was performed. Fifty-eight new tmDNA sequences including members from nine additional phyla were determined. Remarkably, tmDNA sequences could be amplified from all species tested apart from those in the alpha-Proteobacteria. This aspect of the invention allowed a more systematical study of the structure and overall distribution of tmRNA within eubacteria In a second aspect of the invention, alignments are made with the newly isolated tmDNA sequences and previously disclosed tmRNA sequences.

In a third aspect of the invention, the alignments of the tmRNA sequences allow the identification of targets for development of antibacterial drugs.

In a fourth aspect of the invention, the novel tmDNA or tmRNA sequences of the present invention are used to develop diagnostic assays, such as amplification-based assays, for the bacterial species disclosed herein.

BRIEF DESCRIPTION OF THE FIGURES

FIGS. 3A, 3B and 3C show the sequence alignment, structural domains and structural features for the tmRNA of several species of Firmicutes. The tmRNA sequences are set forth in SEQ ID NOs:67-87.

FIGS. 4A and 4B show the sequence alignment, structural domains and structural features for the tmRNA of several species of Thermophiles. The tmRNA sequences are set forth in SEQ ID NOs:88-99.

FIGS. 7A-1, 7A-2, 7B, 7C and 7D show the sequence alignment, structural domains and structural features for the tmRNA of several species of Mesophiles (7A-1, 7A-2, 7C, 7D) and environmental sludge (7B). The tmRNA sequences of the Mesophiles are set forth in SEQ ID NOs:118-123 and 125-128, and the tmRNA sequence of the environmental sludge is set forth in SEQ ID NO:124. The tmRNA sequences of several species of *Chlamydia* are set forth in SEQ ID NOs:129-131.

FIGS. 9A and 9B show the sequence alignment, structural domains and structural features for the tmRNA of several species of Pourpres beta. The tmRNA sequences are set forth in SEQ ID NOs:143-154.

FIGS. 10A, 10B and 10C show the sequence alignment, structural domains and structural features for the tmRNA of several species of Pourpres gamma. The tmRNA sequences are set forth in SEQ ID NOs:155-169.

DETAILED DESCRIPTION OF THE INVENTION

Figure 1A:
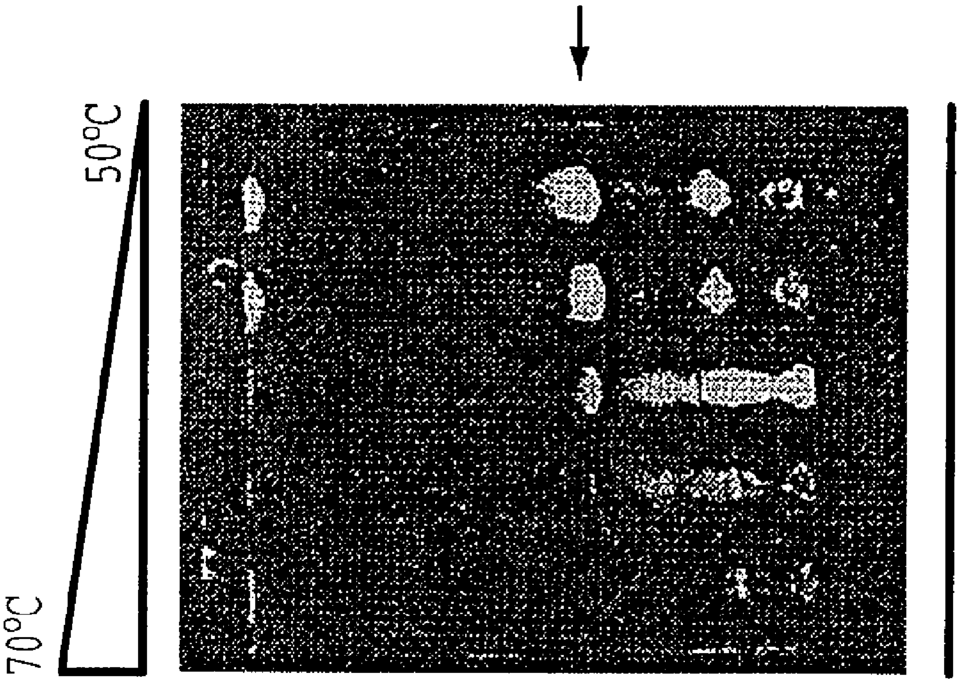
FIGS. 1A-1B show the effect of the annealing temperature (FIG. 1A) and magnesium concentration (FIG. 1B) on amplifying eubacterial tmRNA genes from genomic DNAs using PCR. A: Varying the annealing temperature from 50° to 70° C. during the PCR amplification of *Thermus aquaticus* (1). B; Varying the magnesium concentration to amplify tmDNA genes from *Thermus aquaticus* (1), negative effect of increasing the magnesium concentration), *Acholeplasma laidlawii* (2), positive effect of increasing the magnesium concentration, the upper band is the tmDNA gene) and from *Mycoplasma salivarium* (3), no discernible effect of magnesium ions in that concentration range). The arrows point toward the 4 novel tmDNA genes that have been sequenced.

The present invention is directed to eubacterial tmDNA sequences and the corresponding tmRNA sequences. The present invention is further directed to alignments of eubacterial tmDNA sequences and use of the sequences and sequence alignments for the development of antibacterial drugs.

The novel eubacterial tmDNA sequences determined in accordance with the present invention are set forth in Tables 1-58, below. The alignment of tmRNA sequences is shown in FIGS. 3A-11B, which also show the structural domains and structural features of the tmRNA. The present invention also includes the tmRNA sequences set forth in these figures to the extent they differ from the sequences set forth in Tables 1-58.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria. Thus, the present invention is further directed to the development of drugs for the therapeutic treatment of bacteria, generically or specifically. Suitable drugs are developed on the basis of the tmRNA sequences as described herein.

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. Since these pseudoknots are not found in all canonical transfer RNAs, they can also be targeted with specific drugs. Disruption of either PK1 or PK2 or PK3 with a specific drug would lead to inactive tmRNA molecules in vivo.

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding (such as shown for *Escherichia coli*; Matveeva et al., 1997), and thus, is also available for interaction with other drugs. Moreover, the coding sequence is a critical functional domain of the molecule in its quality-control mechanism in cells.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 basepairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

It has recently been discovered that even the alpha-proteobacteria possess tmRNA genes. These genes are permuted and are made in two parts, connected via a processed linker. These tmRNA gene sequences from alpha-proteobacteria were not found in the course of the present invention because usual PCR methods could not amplify them.

Recent reports have shown that whereas the gene encoding tmRNA is non-essential in *E. coli* (does not kill the bacteria when disrupted), it is indeed essential in *Neisseria gonorrheae* (Huang et al., 2000). Also, tmRNA is directly involved in *Salmonella typhymurium* pathogenticity (Julio et al., 2000).

In summary, tmRNA genes are present in all eubacterial genomes, with no exceptions, but are not present in any genomes from archebacteries or eukaryotes, with the exception of some chloroplasts. The very specific location of tmRNA genes within one of the three main kingdoms of life make them ideal targets for the design of novel antibiotics that will, in principle, interfere very weakly with human biochemistry, compared to usual antibiotics. For a recent review about designing novel antibiotics, see Breithaupt (1999).

The present invention is also directed to diagnostic assays and kits for the detection of bacterial infection, particularly infections caused by bacterial agents disclosed herein. In one embodiment, the coding sequence of each bacterial species is used to design specific primers for use in amplification-based diagnostic assays for infectious diseases. Specific primers are designed in accordance with well known techniques, and such design is readily done by a skilled artisan. Amplification-based diagnostic assays are performed in accordance with conventional techniques well known to skilled artisans. Examples of amplification-based assays include, but are not limited to, polymerase chain reaction (PCR) amplification, strand displacement amplification (SDA), ligase chain reaction (LCR) amplification, nucleic acid sequence based amplification (3SR or NASBA) and amplification methods based on the use of Q-beta replicase.

Drugs which target the sequences described herein are active agents can be formulated in pharmaceutical compositions, which are prepared according to conventional pharmaceutical compounding techniques (*Remington's,* 1990). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences* (18).

Alternatively, targeting therapies may be used to deliver the active agent more specifically to certain types of cell, by the use of targeting systems such as antibodies or cell-specific ligands. Targeting may be desirable for a variety of reasons, e.g. if the agent is unacceptably toxic, or would otherwise require too high a dosage, or otherwise be unable to enter the target cells.

Antisense active agents can also be delivered by techniques described in U.S. Pat. Nos. 5,811,088; 5,861,290 and 5,767,102.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

1. Extraction of Genomic DNA

Bacterial genomic DNAs were prepared from ≈10 mg freeze-dried cells provided from ATCC (American Type Culture Collection, Virginia, USA). Cell pellets were resuspended in 750 μL of lysis buffer (50 mM Tris (pH 8.0), 50 mM EDTA and 20% sucrose). 150 μL of a 10 mg/mL solution of lysozyme was mixed and let stand at room temperature for 15 min. 150 μL of 1% SDS was added and let stand at room temperature for 15 minutes. Four to five phenol/chloroform extractions were performed, until the sample was clear and there was no interphase. Two to five μL of a 10 mg/mL solution of RNase DNase-free was added and incubated at room temperature for 30 minutes. After a phenol/chloroform extraction of the enzyme, the genomic DNA was precipitated with 1/10 volume of 3M NaOAc (pH 5.5) and 1 volume isopropanol, and stored at −20° C. for 2 hours. After centrifugation, the genomic DNAs were washed with 70% ethanol, vacuum-dried and diluted in sterile water to a final concentration of 10 ng/μL.

2. Primer Sets for PCR Reactions

The following primer sets were used during the PCR: primer set A (based on *E. coli* tmRNA termini):

```
5'-GGG GCT GAT TCT GGA TTC GAC-3'    (SEQ ID NO: 1)
and

5'-TGG AGC TGG CGG GAG TTG AAC-3';   (SEQ ID NO: 2)
```

primer set B (based on *T. neapolitana* tmRNA termini):

```
5'-GGG GGC GGA AAG GAT TCG ACG-3'    (SEQ ID NO: 3)
and

5'-TGG AGG CGG CGG GAA TCG AAC-3';   (SEQ ID NO: 4)
```

primer set C (based on *M. pneumoniae* tmRNA termini):

```
5'-GGG GAT GTC ATG GTT TTG ACA-3'    (SEQ ID NO: 5)
and

5'-TGG AGA TGG CGG GAA TCG AAC-3';   (SEQ ID NO: 6)
and
```

primer set D (based on *C. tepidum* tmRNA termini):

```
5'-GGG GAT GAC AGG CTA TCG ACA-3'    (SEQ ID NO;7)
and

5'-TGG AGA TGG CGG GAC TTG AAC-3'.   (SEQ ID NO: 8)
```

3. PCR Reaction

Sequences of tmRNA genes were obtained by polymerase chain reaction (PCR) in 25 μL using 40 ng of genomic DNA per reaction. The following general scheme was utilized for all of the sequences:

(a) 94° C. to 96° C. for 4 min. (first denaturation of genomic DNAs, done only once); then (b) 35 to 40 PCR cycles with 2.5 to 5 Units of Taq DNA polymerase in a 25 μL reaction volume, according to the following scheme (40 ng of genomic DNAs/PCR reaction):

1. denature at 94° to −96° C. for 25 to 30 sec;
2. anneal at 44° to 55° C. for 20 to 30 sec; and
3. extension at 72° C. for 10 sec.

The magnesium conc. was optimized for each phyla from 3.5 to 13.5 mM.

4. Elution of Amplified DNAs

The various PCR-amplified tmDNA bands were gel purified (5% PAGE), stained (ethidium bromide staining), cut using a sterile razor blade, and shaken over-night (passive elution, using a vibrator) in a 350 μl solution containing 10 mM Tris-HCl buffer (pH 8.1). The following day, the PCR amplified tmDNAs were ethanol precipitated, washed in 70% ETOH, vacuum dried and the DNA pellets were dissolved in 18 μl of RNase-DNase free sterile water.

5. DNA Sequencing

Six μL of amplified DNAs were added to 3.2 picomoles of the primer that was used in the PCR. To verify the novel tmDNA sequences, each of the two primers were used independently to sequence each of the two PCR-amplified DNA strands. Some tmDNAs were already engineered at their 5'-ends with a T7 promoter, to be able to transcribe directly the tmDNAs into tmRNAs by in vitro transcription.

Dye terminator sequencing was achieved at the DNA sequencing facility of the Human Genetics Institute. In addition to novel tmRNA sequences that are not available publicly, several tmDNA sequences that were already known have been verified and several sequencing mistakes have been found and corrected (especially for *Alcaligenes eutrophus* tmRNA).

Example 2

Amplification Reactions for Eubacterial tmDNA

Eubacterial tmDNA was amplified by PCR in accordance with Example 1, using the following conditions.

*Acidobacterium:*

Primer Set B; Annealing temp. during PCR: 53° C. for 20 sec; $Mg^{2+}$ conc.: 4.5 mM.

*Coprothermobacter:*

Primer Set B; Annealing temp. during PCR: 55° C. for 30 sec; $Mg^{2+}$ conc.: 5.5 mM.

Cytophagales:

Primer Set A; Annealing temp. during PCR: 46° C. for 30 sec; $Mg^{2+}$ conc.: 4.5 mM.

*Dictyoglomus:*

Primer set B; Annealing temp. during PCR: 55° C. for 30 sec; $Mg^{2+}$ conc.: 4.5 mM.

Environmental Samples:

Sludge DNA

Primer set C; Annealing temp. during PCR: 51° C. for $20^{sec;\ Mg2+}$ conc.: 13.5 mM.

Rumenal Fluid DNA

Primer set D; Annealing temp. during PCR: 50° C. for 30 sec; $Mg^{2+}$ conc.: 9.5 mM.

*Fibrobacter:*

Primer set A; Annealing temp. during PCR: 51° C.; $Mg^{2+}$ conc.: 3.5 mM.

Firmicutes:

Fusobacteria:

Primer set A; Annealing temp. during PCR: 52° C.; $Mg^{2+}$ conc.: 5.5 mM.

High G-C:

Primer set A; Annealing temp. during PCR: 50-55° C.; $Mg^{2+}$ conc.: 4.5 mM.

Low G-C:

Primer sets A or B; Annealing temp. during PCR: 52° C.; $Mg^{2+}$ conc.: 5.5 to 7.5 mM.

Mycoplasmes:

Primer set A; Annealing temp. during PCR: 52° C.; $Mg^{2+}$ conc.: 3.5 to 5.5 mM.

Green Non-Sulfur:

Primer sets A or B; Annealing temp. during PCR: 46 to 52° C.; $Mg^{2+}$ conc.: 4.5 mM.

Green Sulfur:

Primer set A; Annealing temp. during PCR: 46° C.; $Mg^{2+}$ conc.: 4.5 mM.

Planctomycetales:

Primer set A; Annealing temp. during PCR: 48 to 52° C.; $Mg^{2+}$ conc.: 7.5 mM.

Proteobacteria:

beta:

Primer sets A and/or B; Annealing temp. during PCR: 50° C. for 25 sec; $Mg^{2+}$ conc.: 3.5 mM.

delta:

Primer set B; Annealing temp. during PCR: 55° C.; $Mg^{2+}$ conc.: 3.5 to 4.5 mM.

epsilon:

Primer set A; Annealing temp. during PCR: 46° C. for 30 sec; $Mg^{2+}$ conc.: 3.5 mM.

gamma:

Primer set A; Annealing temp. during PCR: 44 C for 30 sec; $Mg^{2+}$ conc.: 5.5 mM.

Spirochetes:

Primer set A; Annealing temp. during PCR: 52° C.; $Mg^{2+}$ conc.: 4.5 mM.

*Thermodesulfobacterium:*

Primer set B; Annealing temp. during PCR: 55° C.; $Mg^{2+}$ conc.: 5.5 mM.

Thermotogales:

Primer set B; Annealing temp. during PCR: 46° C.; $Mg^{2+}$ conc.: 7.5 mM.

Deinococcales:

Primer set B; Annealing temp. during PCR: 52° C.; $Mg^{2+}$ conc.: 3.5 mM.

Verrucomicrobia:

Primer set A; Annealing temp. during PCR: 53° C. for 25 sec; $Mg^{2+}$ conc.: 3.5 mM.

Example 3

Amplification of Eubacterial tmDNA

Figure 1B:
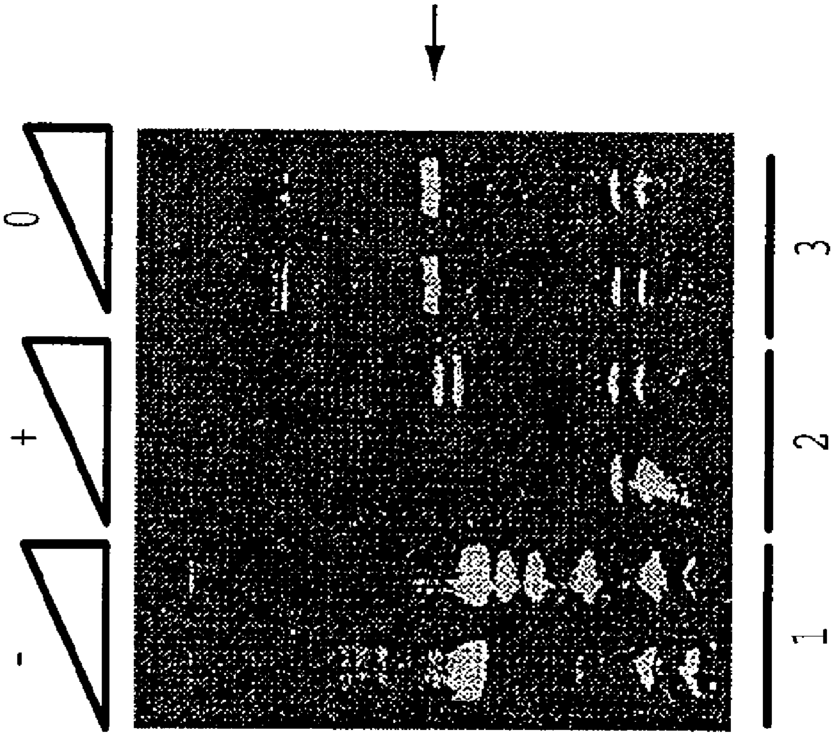

Specific PCR amplification of tmRNA genes was achieved for both thermophilic and mesophilic eubacterial tmRNA genes. For the novel tmDNA genes found in thermophiles, both the magnesium concentration and the annealing temperature (FIG. 1A) were optimized. As shown in FIG. 1A, a specific amplification of *Thermus aquaticus* tmDNA was observed with an annealing temperature around 50° C., whereas at higher temperatures there is a gradual decrease in the amount of amplified tmDNA. For mesophiles, the magnesium concentration during PCR was critical (FIG. 1B), but the annealing temperature could vary from 44° C. to 60° C. without significant effects on the amplification. FIG. 1B shows various effects of increasing the magnesium concentration on the PCR amplification of three novel eubacterial tmDNA genes. Increasing magnesium concentration from 3.5 mM to 5.5 mM has either a negative (FIG. 1B, panel 1), a positive (FIG. 1B, panel 2) or no effect on specifically amplifying eubacterial tmDNA genes.

Figure 2:
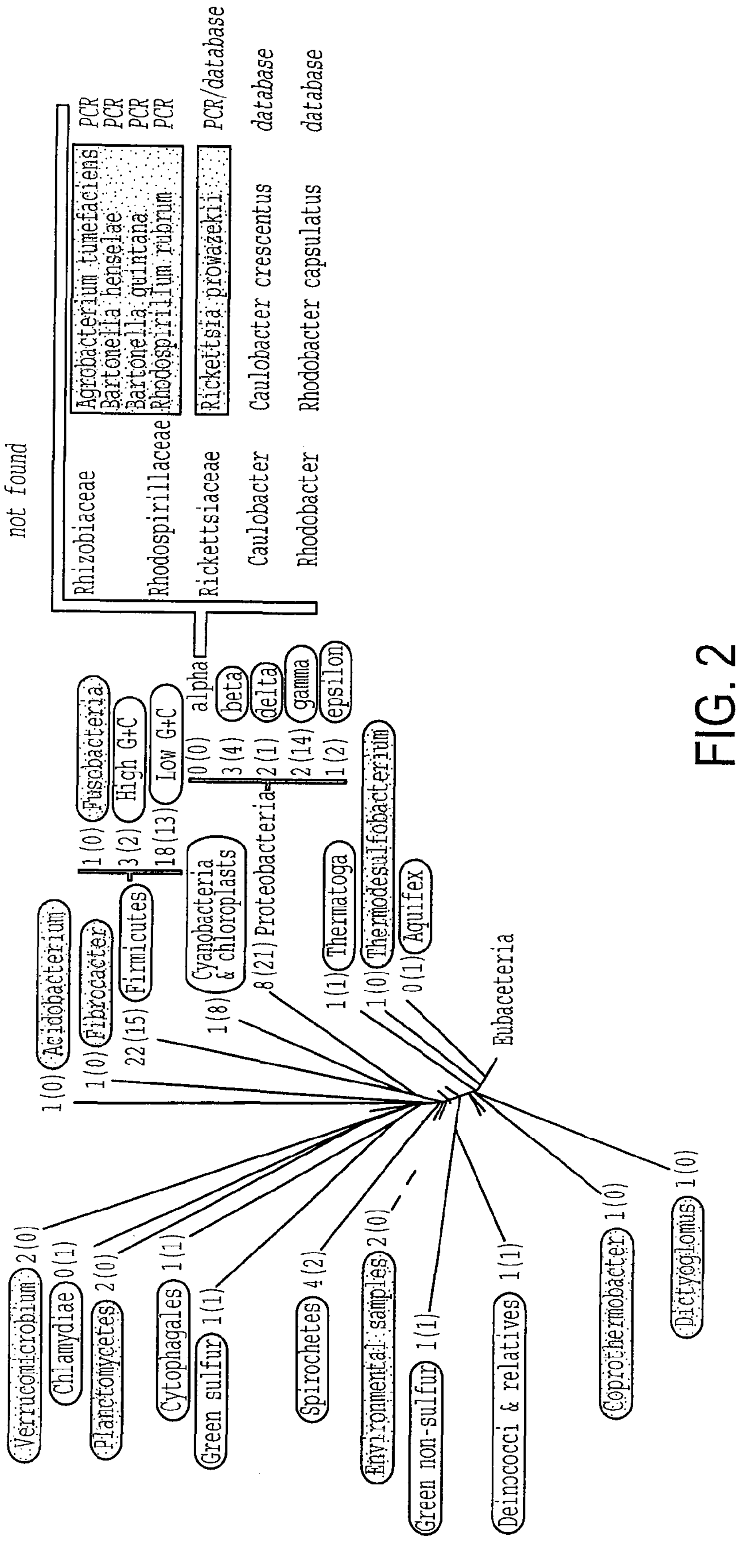
FIG. 2 shows the distribution of tmDNA sequences within eubacterial genomes. The circled phyla or subgroups contain tmDNA sequences and those shaded are new members of this category. The numbers shown close to each phylum are the 51 tmDNA sequences that have are disclosed herein and the numbers in parenthesis are the 53 tmDNA sequences that were previously known (summarized in Williams, 1999; Wower and Zwieb, 1999). The environmental samples are indicated with a dashed line as their connection to the tree is unknown. The 5 alpha-Proteobacteria in which tmDNA sequences were not detected by PCR analysis are labeled "PCR" and the 3 analyzed by Blast search of the complete, or nearly complete, sequenced genomes are labeled "database".
Figure 4A:
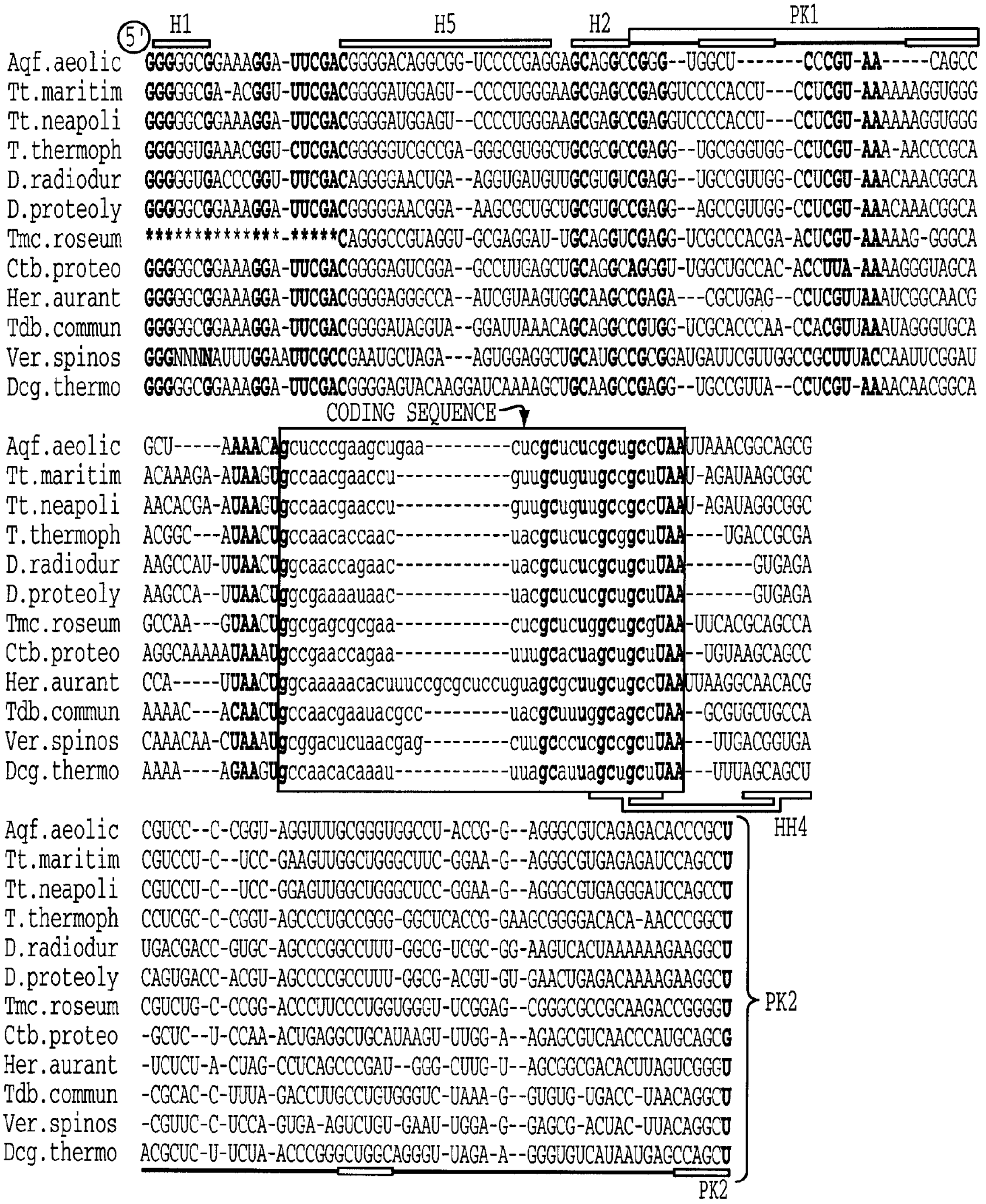
Figure 5A:
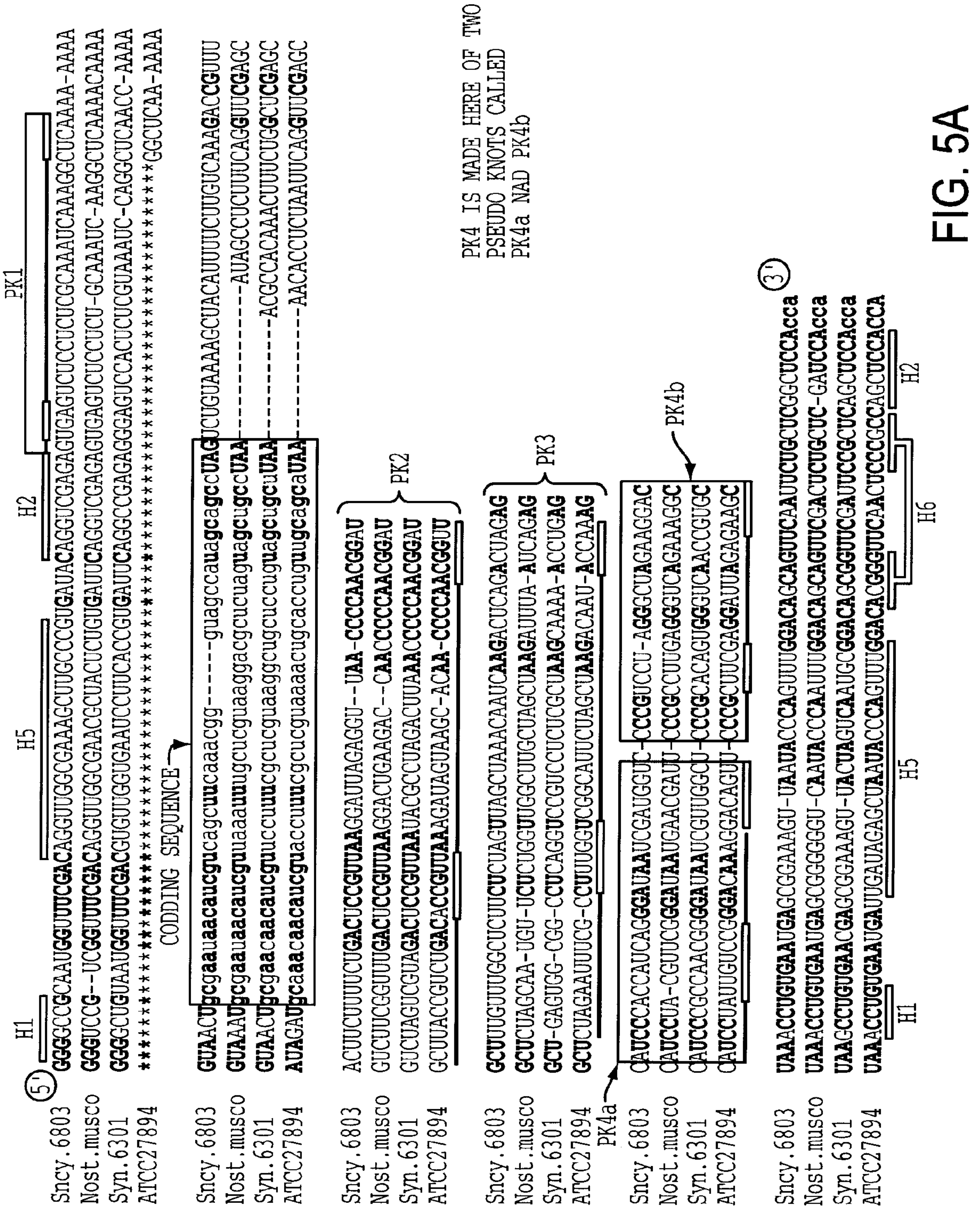
FIGS. 5A and 5B show the sequence alignment, structural domains and structural features for the tmRNA of several species of Cyanobacteries (5A) and chloroplasts (5B). The tmRNA sequences of the Cyanobacteries are set forth in SEQ ID NOs:100-103, and the tmRNA sequences of the chloroplasts are set forth in SEQ ID NOs:104-108.
Figure 5B:
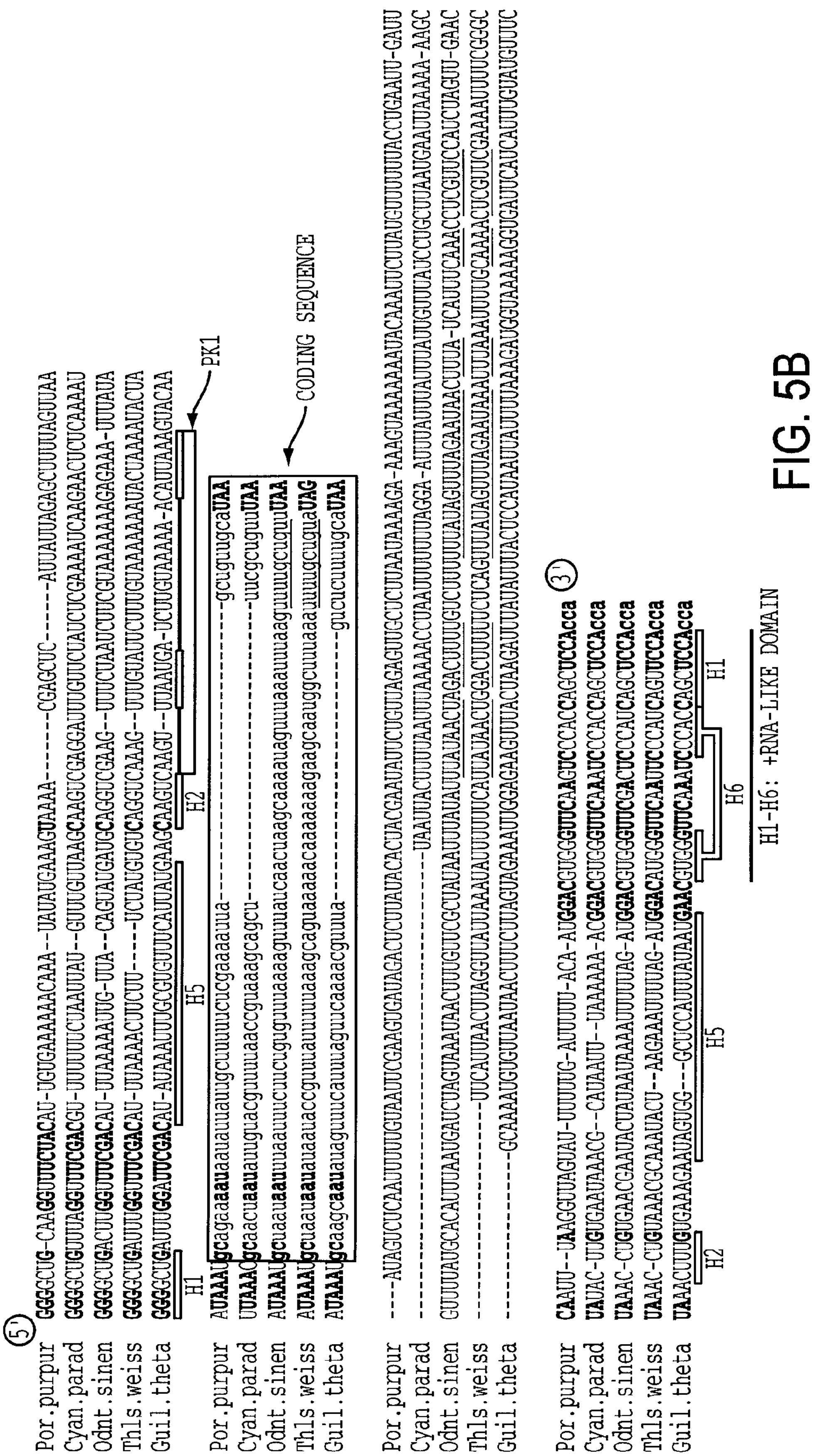
Figure 6A:
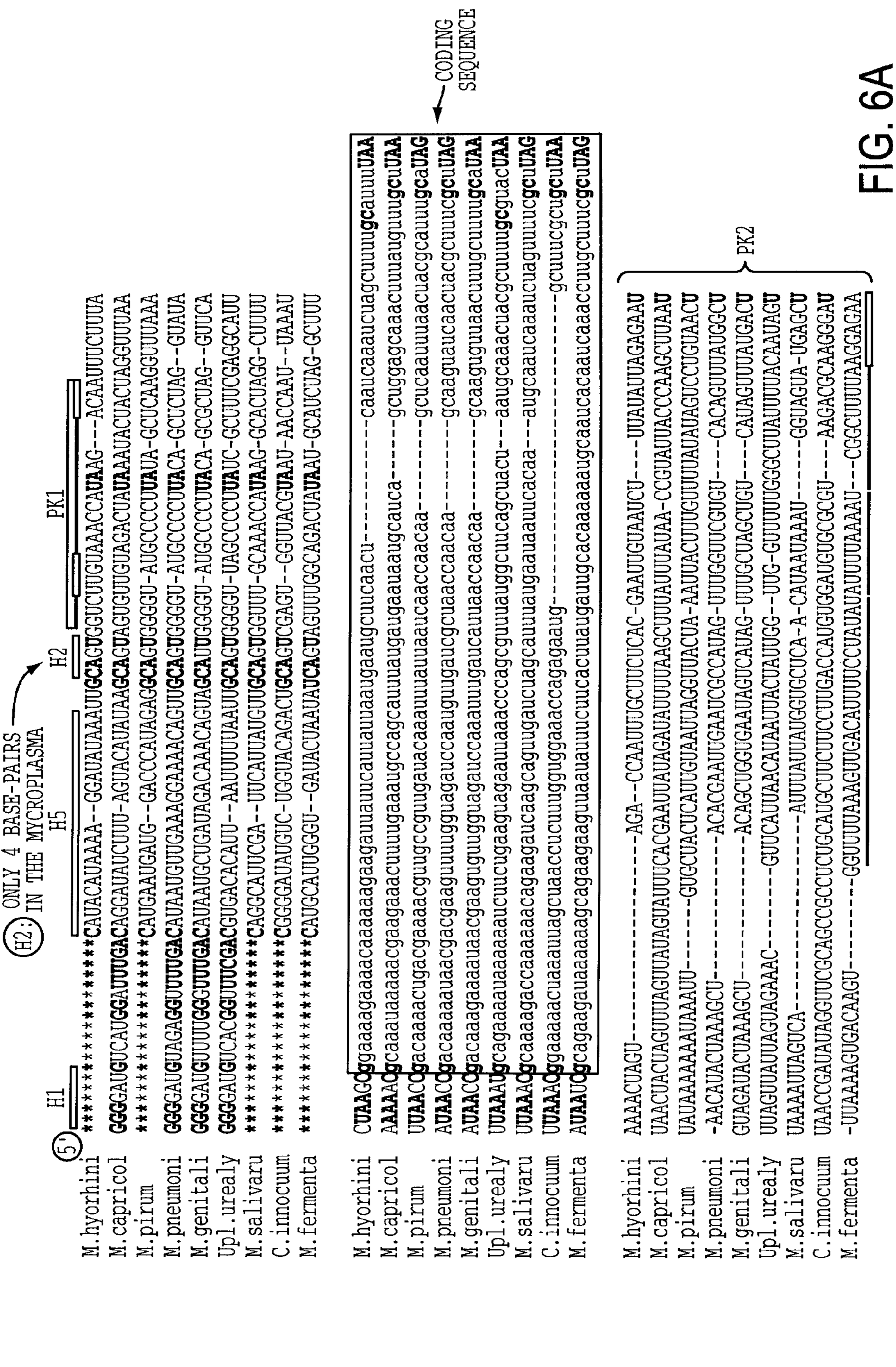
FIGS. 6A and 6B show the sequence alignment, structural domains and structural features for the tmRNA of several species of Mycoplasmes. The tmRNA sequences are set forth in SEQ ID NOs:109-117.
Figure 6B:
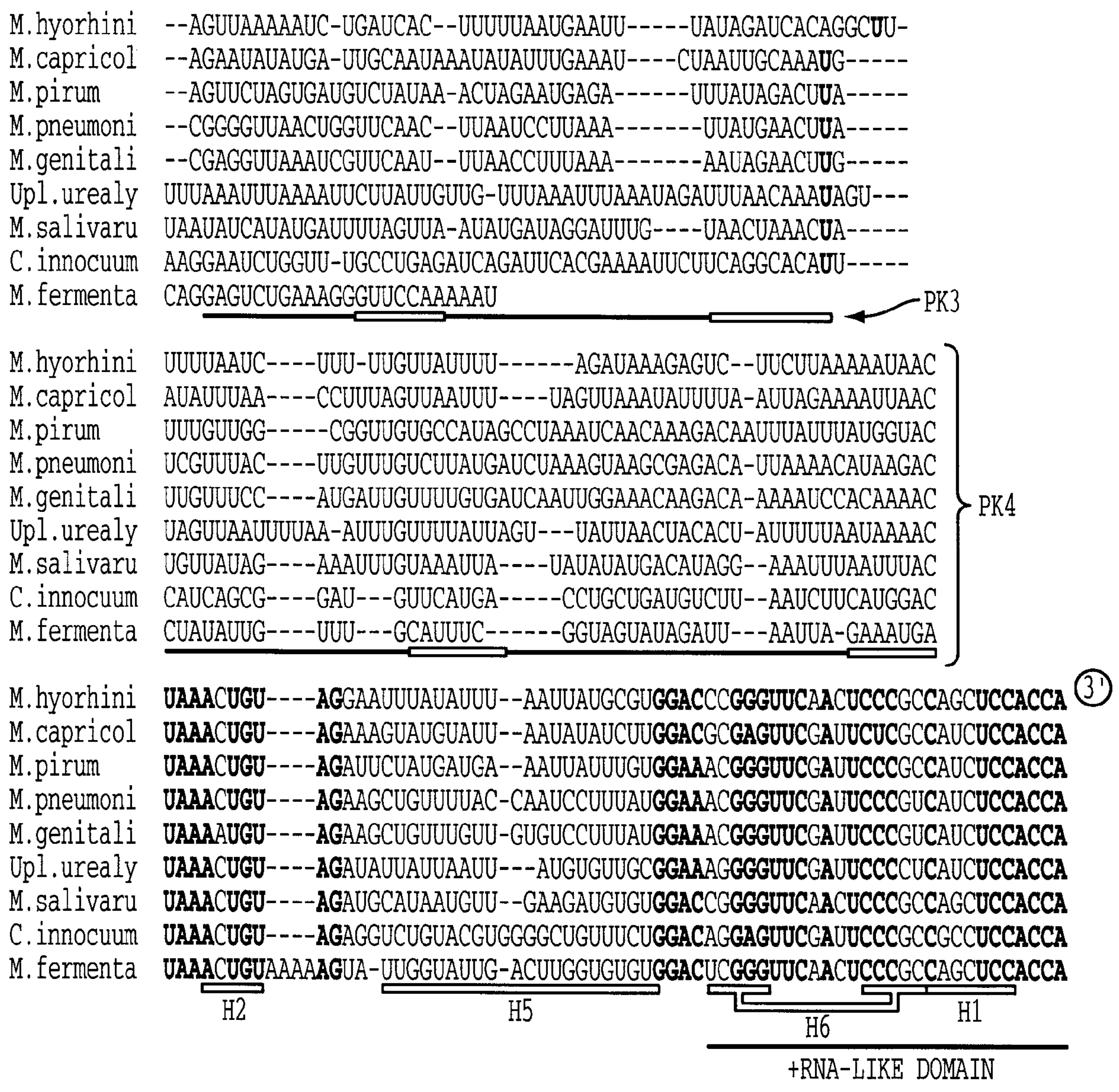
Figures 1, 7A:
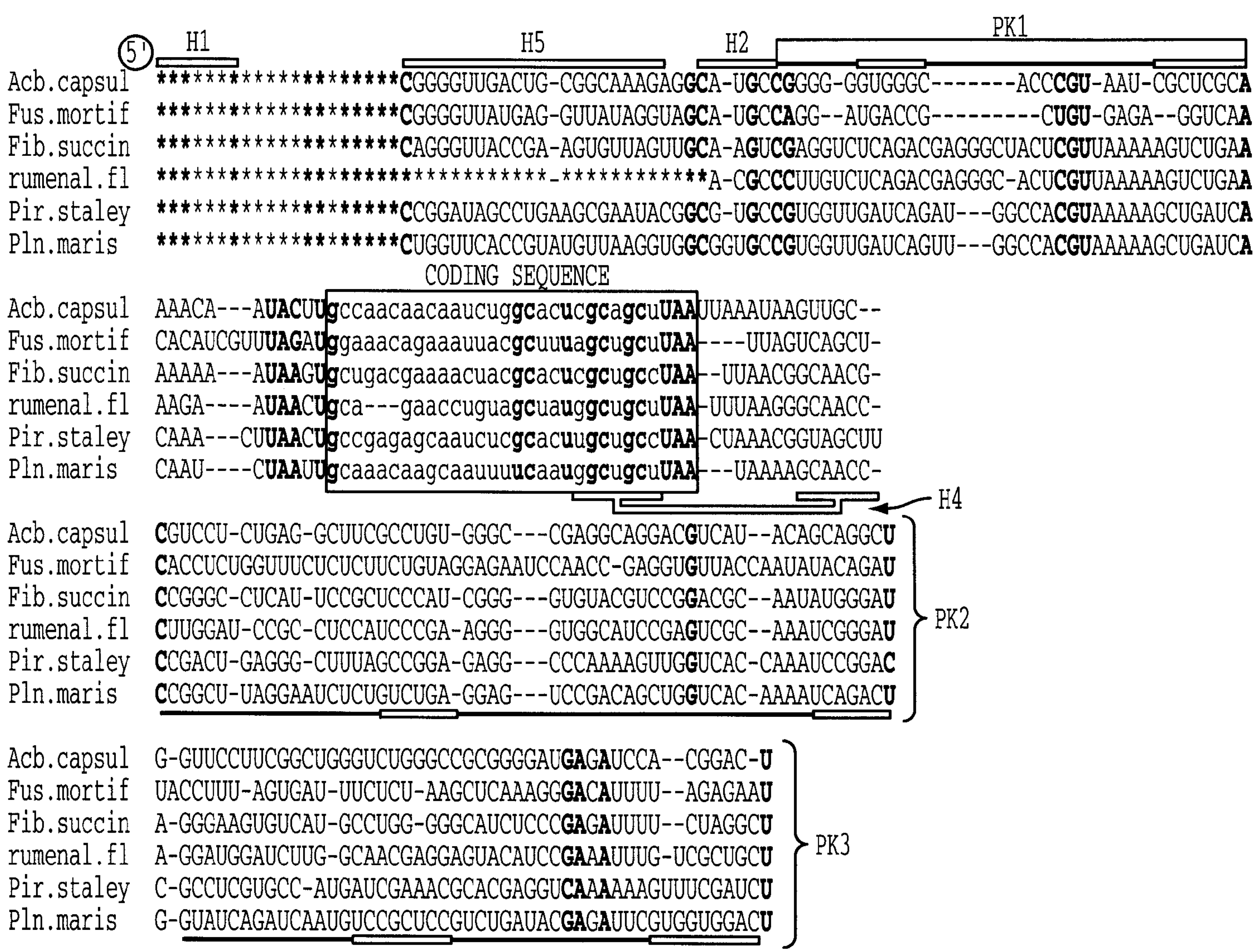
Figures 2, 7A:
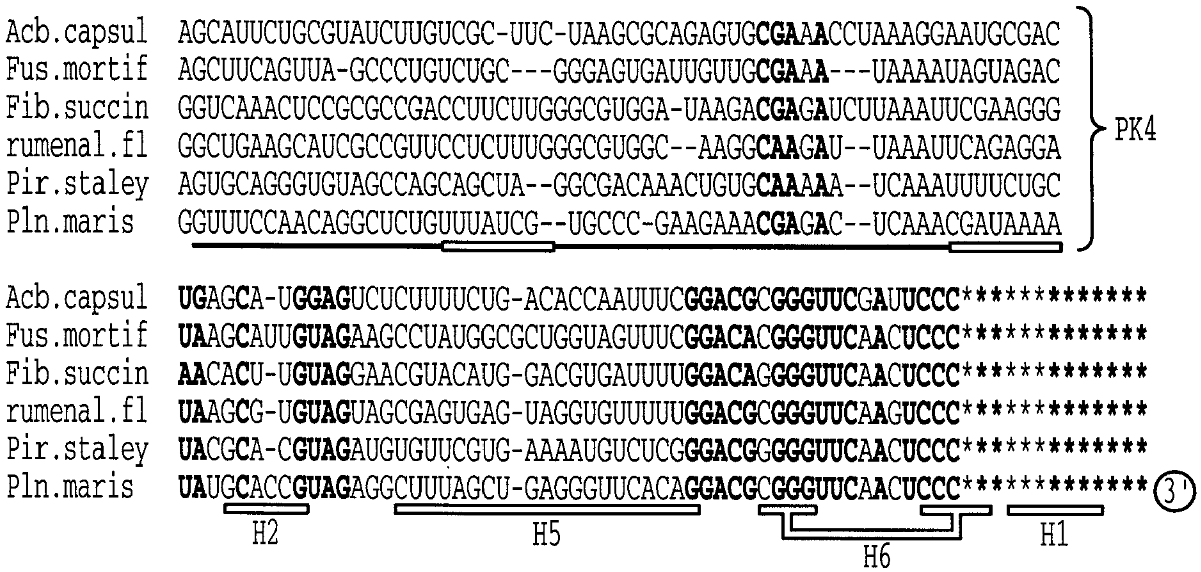
Figure 7B:
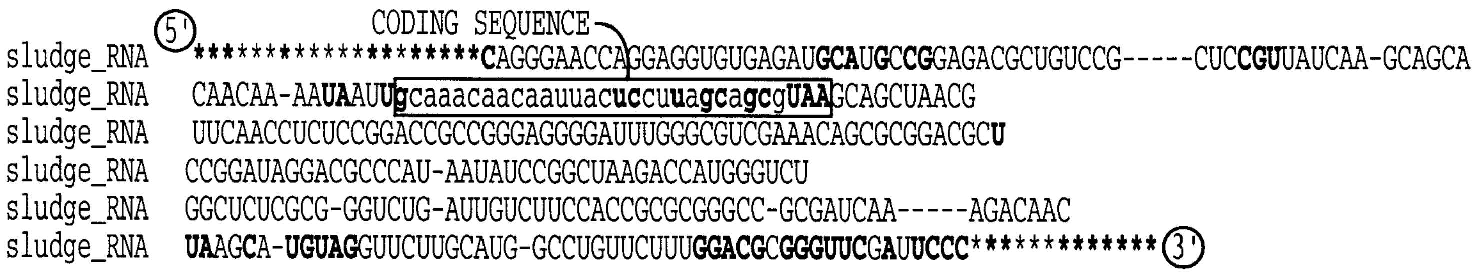
Figure 7C:
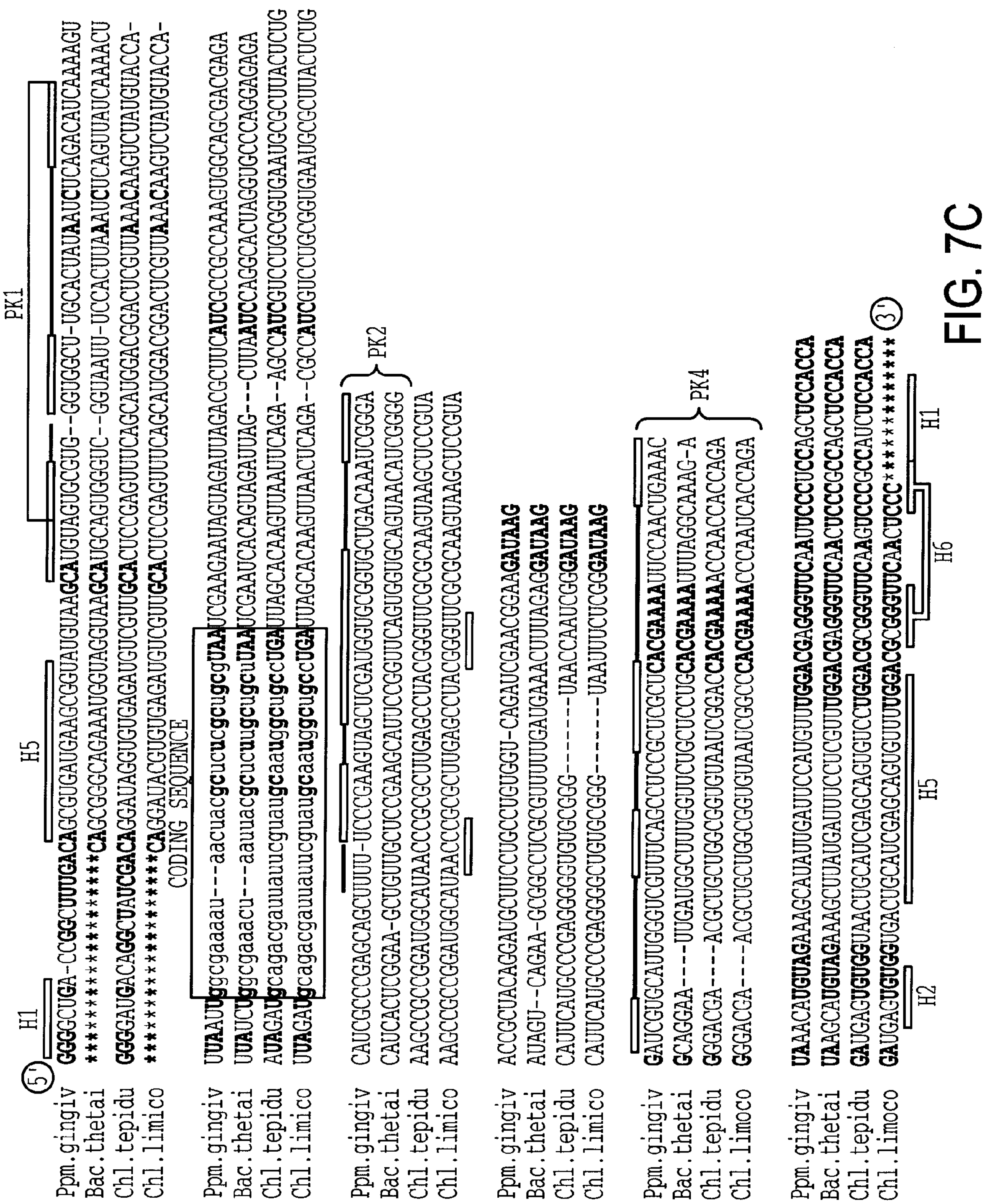
Figure 7D:
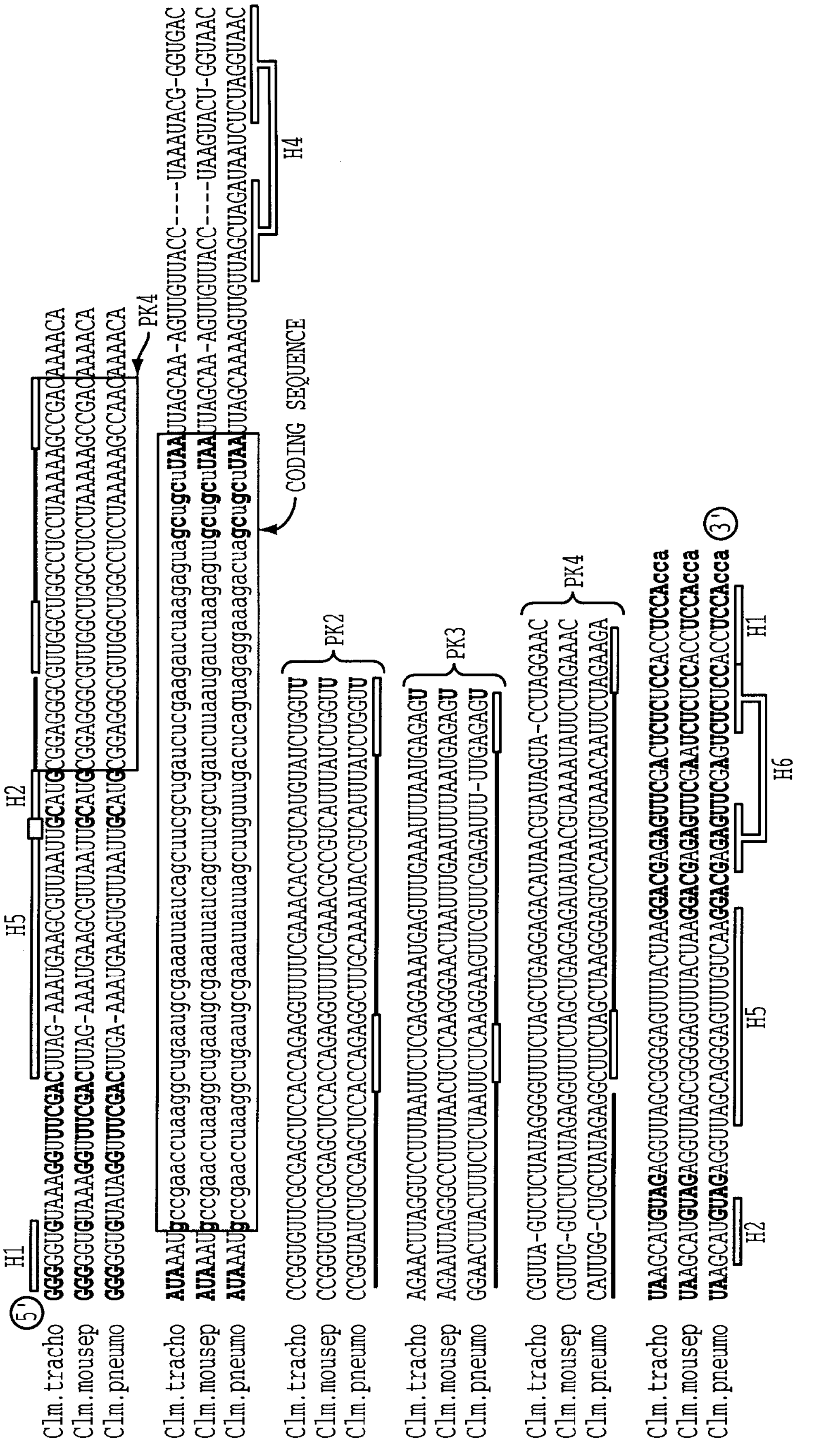
Figure 8A:
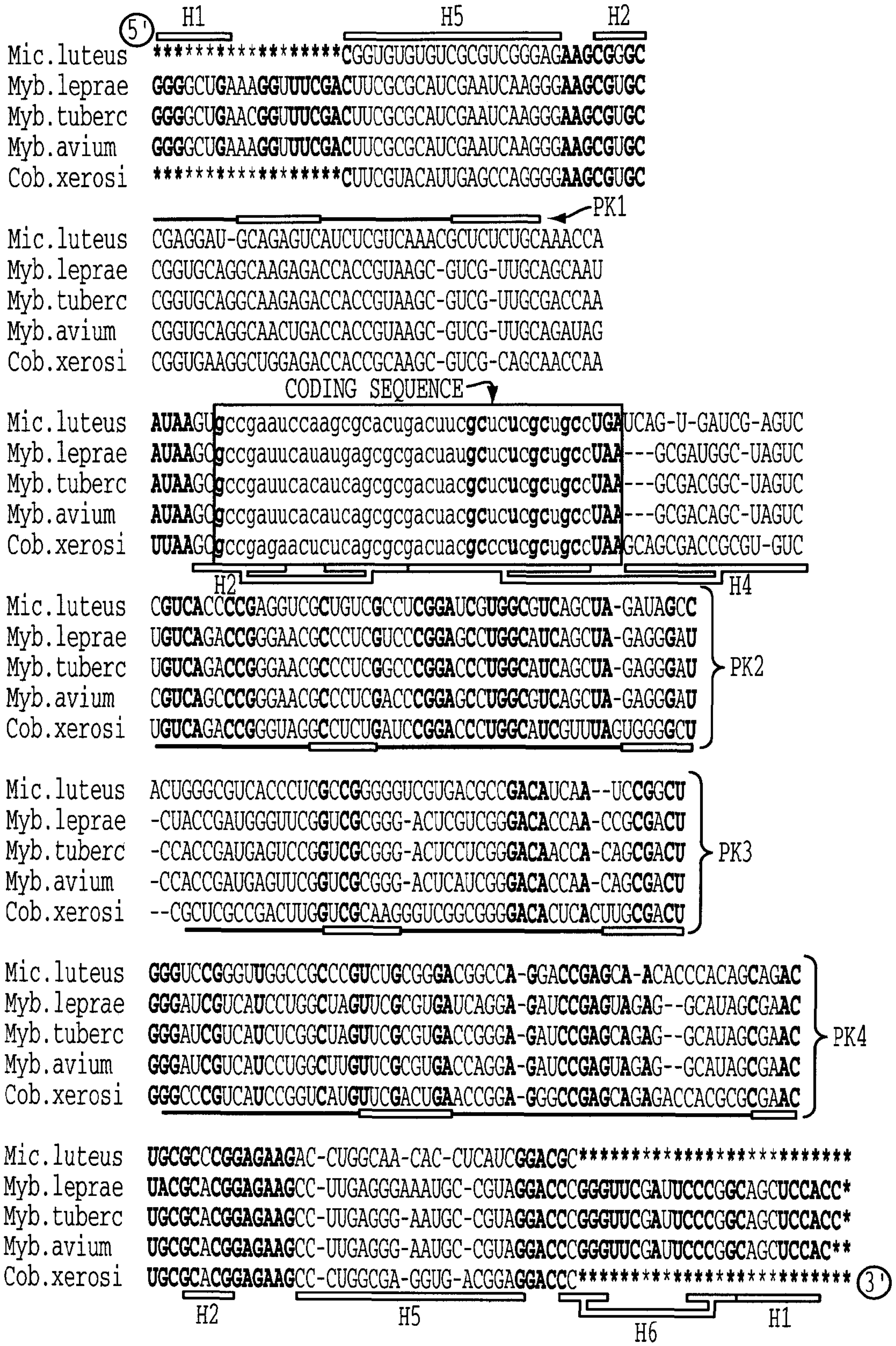
FIGS. 8A and 8B show the sequence alignment, structural domains and structural features for the tmRNA of several species of Actinobacteries (8A) and Spirochaetes (8B). The tmRNA sequences of the Actinobacteries are set forth in SEQ ID NOs:132-136, and the tmRNA sequences of the Spirochaetes are set forth in SEQ ID NOs:137-142.
Figure 8B:
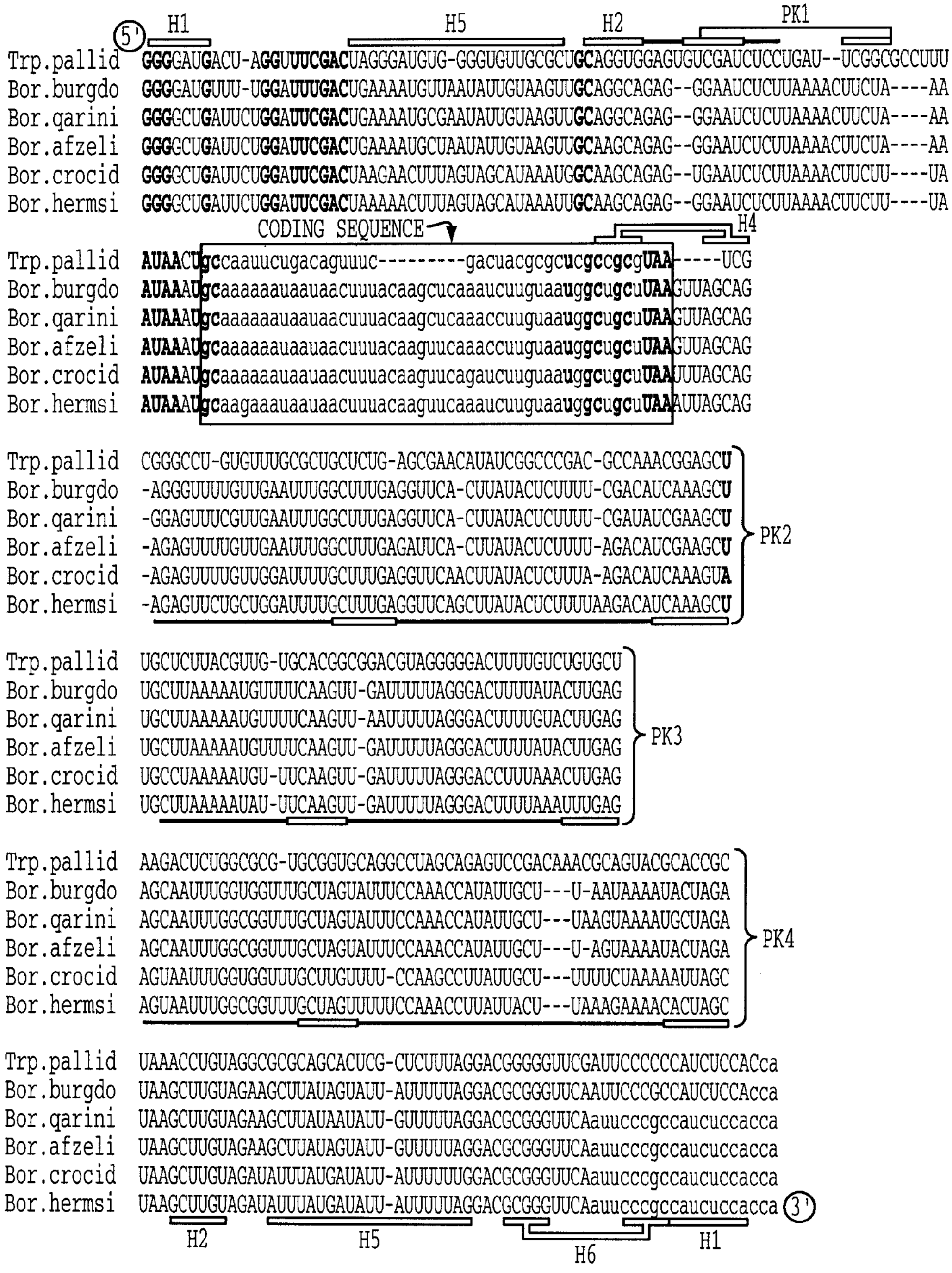
Figure 9A:
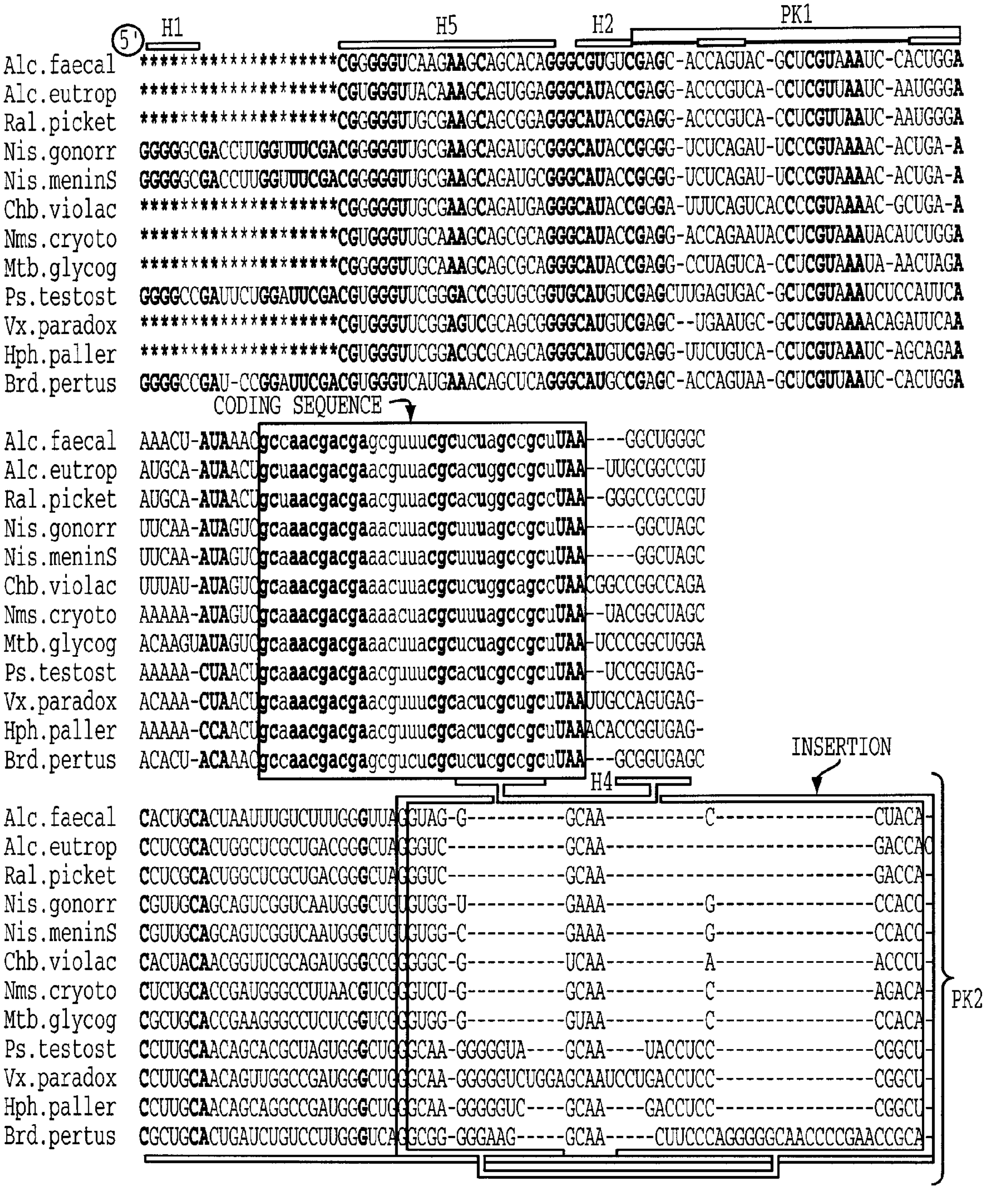
Figure 11A:
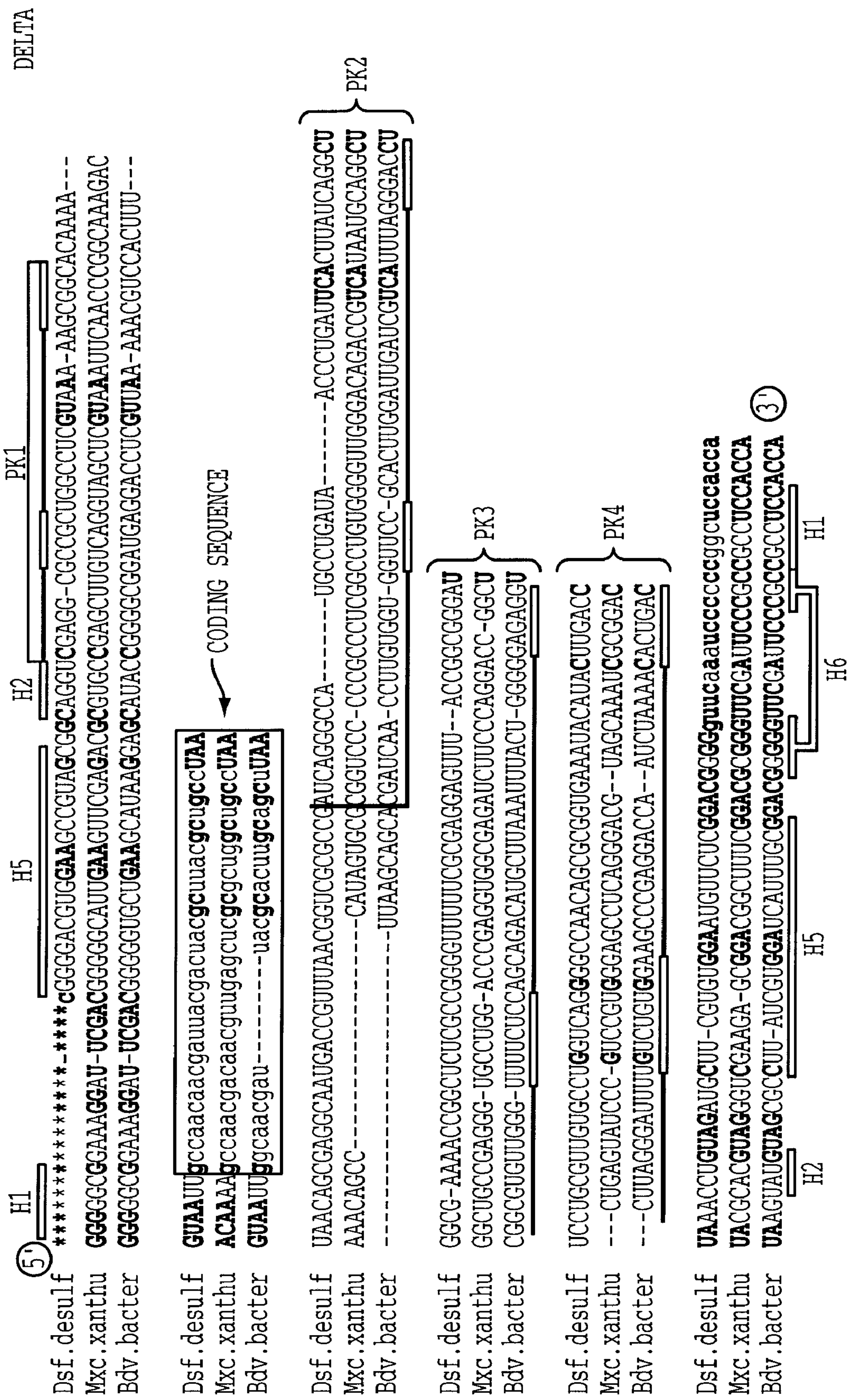
FIGS. 11A and 11B show the sequence alignment, structural domains and structural features for the tmRNA of several species of Pourpres delta (11A) and Pourpres epsilon (11B). The tmRNA sequences of the Pourpres delta are set forth in SEQ ID NOs:170-172, and the tmRNA sequences of the Pourpres epsilon are set forth in SEQ ID NOs:173-175.
Figure 11B:
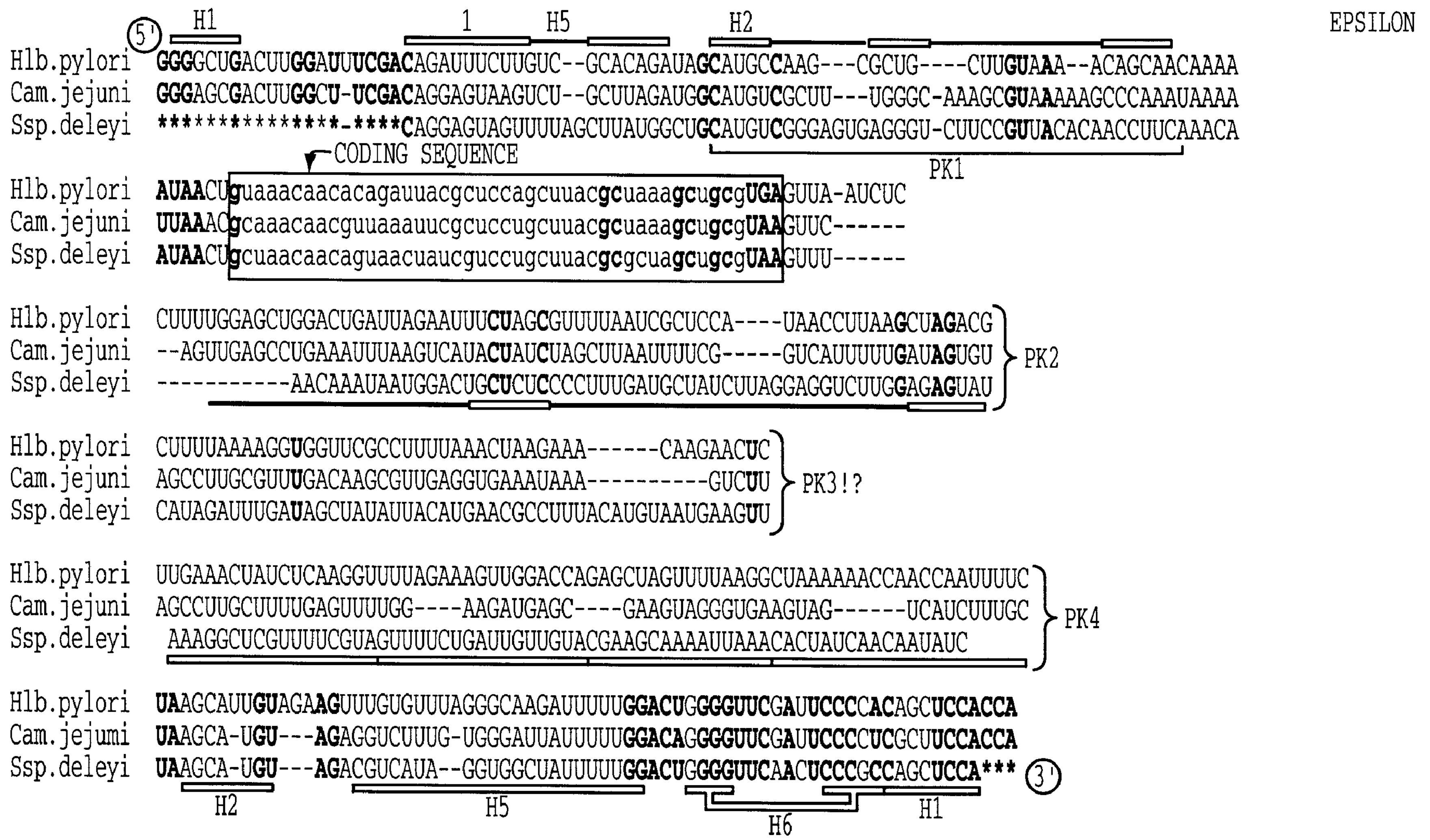

According to these procedures, tmRNA genes from many eubacteria including known human pathogens were amplified. The PCR was facilitated by sequence conservation at both 5' and 3' ends and was performed as described (Williams and Bartel, 1996), with modifications. This study was initiated to collect further sequences from eubacterial tmDNA genes, as well as to test experimentally whether tmDNA genes could be found in all bacterial phyla or subgroups. 51 new tmDNA sequences were determined (FIG. 2), including sequences from members of 8 additional phyla and 1 subgroup (shaded boxes in FIG. 2). The 58 new tmDNA sequences are set forth in Tables 1-58. This brings coverage to a total of 104 sequences in 19 bacterial phyla. Interestingly, tmDNA sequences could be amplified from all species tested apart from those in the alpha-Proteobacteria. Five genomic DNAs from alpha-Proteobacteria (*Agrobacterium tumefaciens, Bartonella henselae, Bartonella quintana, Rhodospirillum rubrum* and *Rickettsia prowazekii*) were extensively checked using various oligonucleotides, annealing temperatures and magnesium concentrations. No specific amplified tmDNA sequences were detected in this subgroup. Moreover, no putative tmDNA sequences could be identified (results herein and Williams, 1999) by Blast searches on the 1 fully sequenced (*Rickettsia prowazekii*) and 2 nearly completed (*Caulobacter crescentus* and *Rhodobacter capsulatus*) alpha-proteobacterial genomes (FIG. 2).

It cannot be ruled out that tmDNA sequences may have largely diverged in the alpha-proteobacterial sub-group compared to other bacterial phyla, and that both PCR methods and Blast searches are missing the relevant sequences. While tmRNA is dispensable in *E. coli* (Ando et al., 1996), it is striking that it has been found in all bacteria tested other than the alpha-Proteobacteria. The alpha-Proteobacteria have undergone reductive evolution. This has been more intensive in one of the two sub-classes than in the other (Gray and Spencer, 1996), but tmRNA sequences have not been found even in the sub-class with the larger genome. Based on sequence comparison, the alpha-Proteobacteria and mitochondria are evolutionary relatives (Yang et al., 1985; Andersson et al., 1998). The drastic downsizing in what has become mitochondrial genomes means that it is not reasonable to draw inferences on the relationship between alpha-Proteobacteria and mitochondria based on their mutual apparent absence of tmRNA. It is nevertheless, of interest, that at least some chloroplasts and cyanelle genomes have tmDNA sequences, and the cyanobacteria, with which they are evolutionary related, also have tmRNA.

TABLE 1

| tmDNA Sequence for *Acidobacterium capsulatum* (*Acidobacterium*) |
|---|
| (SEQ ID NO: 9) |
| GGGGGCGGAAAGGATTCGACGGGGTTGACTGCGGCAAAGAGGCATGCCGG |
| GGGGTGGGCACCCGTAATCGCTCGCAAAACAATACTTGCCAACAACAATC |
| TGGCACTCGCAGCTTAATTAAATAAGTTGCCGTCCTCTGAGGCTTCGCCT |
| GTGGGCCGAGGCAGGACGTCATACAGCAGGCTGGTTCCTTCGGCTGGGTC |
| TGGGCCGCGGGGATGAGATCCACGGACTAGCATTCTGCGTATCTTGTCGC |
| TTCTAAGCGCAGAGTGCGAAACCTAAAGGAATGCGACTGAGCATGGAGTC |
| TCTTTTCTGACACCAATTTCGGACGCGGGTTCGATTCCCGCCGCCTCCAC |
| CA |

TABLE 2

| tmDNA Sequence for *Coprothermobacter proteolyticus* (60 degrees) |
|---|
| (SEQ ID NO: 10) |
| GGGGGCGGAAAGGATTCGACGGGGAGTCGGAGCCTTGAGCTGCAGGCAGG |
| GTTGGCTGCCACACCTTAAAAAGGGTAGCAAGGCAAAAATAAATGCCGAA |
| CCAGAATTTGCACTAGCTGCTTAATGTAAGCAGCCGCTCTCCAAACTGAG |
| GCTGCATAAGTTTGGAAGAGCGTCAACCCATGCAGCGGCTCTTAAGCAGT |
| GGCACCAGCTGTTTAAGGGTGAAAAGAGTGGTGCTGGGCAGTGCGGTTGG |
| GCTTCCTGGGCTGCACTGTCGAGACTTCACAGGAGGGCTAAGCCTGTAGA |
| CGCGAAAGGTGGCGGCTCGTCGGACGCGGGTTCGATTCCCGCCGCCTCCA |
| CCA |

TABLE 3

| tmDNA Sequence for *Bacteroides thetaiotaomicron* (*bacteroides/flavobacterium*) |
|---|
| (SEQ ID NO: 11) |
| GGGGCTGATTCTGGATTCGACAGCGGGCAGAAATGGTAGGTAAGCATGCA |
| GTGGGTCGGTAATTTCCACTTAAATCTCAGTTATCAAAACTTTATCTGGC |
| GAAACTAATTACGCTCTTGCTGCTTAATCGAATCACAGTAGATTAGCTTA |
| ATCCAGGCACTAGGTGCCAGGACGAGACATCACTCGGAAGCTGTTGCTCC |
| GAAGCATTCCGGTTCAGTGGTGCAGTAACATCGGGGATAGTCAGAAGCGG |
| CCTCGCGTTTTTGATGAAACTTTAGAGGATAAGGCAGGAATTGATGGCTT |
| TGGTTCTGCTCCTGCACGAAAATTTAGGCAAAGATAAGCATGTAGAAAGC |
| TTATGATTTCCTCGTTTGGACGAGGGTTCAACTCCCGCCAGCTCCACCA |

TABLE 4 tmDNA Sequence for *Dictyoglomus thermophilum* (70 degrees)

(SEQ ID NO: 12)
GGGGCTGATTCTGGATTCGACAGGGAGTACAAGGATCAAAAGCTGCAAGC
CGAGGTGCCGTTACCTCGTAAAACAACGGCAAAAAAGAAGTGCCAACACA
AATTTAGCATTAGCTGCTTAATTTAGCAGCTACGCTCTTCTAACCCGGGC
TGGCAGGGTTAGAAGGGTGTCATAATGAGCCAGCTGCCCCTTCCGACTCC
CCTAAGGAAGGGAAAGATGTAGGGGATAGGTGCTTACAGAATCCTGCGGG
AGGGAGTCTGTAAGTGCCGAAAAGTTAAAACTCCCGCTAAGCTTGTAGAG
GCTTTTGATTCTTGCTCTCTGGACGCGGGTTCAACTCCCGCCAGCTCCAC
CA

TABLE 5 tmDNA Sequence for Environmental Sample from Rumenal Fluid (SEQ ID NO: 13)
ACGCCCTTGTCTCAGACGAGGGCACTCGTTAAAAAGTCTGAAAAGAATAA
CTGCAGAACCTGTAGCTATGGCTGCTTAATTTAAGGGCAACCCTTGGATC
CGCCTCCATCCCGAAGGGGTGGCATCCGAGTCGCAAATCGGGATAGGATG
GATCTTGGCAACGAGGAGTACATCCGAAATTTGTCGCTGCTGGCTGAAGC
ATCGCCGTTCCTCTTTGGGCGTGGCAAGGCAAGATTAAATTCAGAGGATA
AGCGTGTAGTAGCGAGTGAGTAGGTGTTTTTGGACGCGGGTTCAAGTCCC
GCCATCTCCACCA

TABLE 6 tmDNA Sequence for Environmental Sample from Sludge (SEQ ID NO: 14)
GGGGATGTCATGGTTTTGACAGGGAACCAGGAGGTGTGAGATGCATGCCG
GAGACGCTGTCCGCTCCGTTATCAAGCAGCAAACAAAACTAATTGCAAAC
AACAATTACTCCTTAGCAGCGTAAGCAGCTAACGTTCAACCTCTCCGGAC
CGCCGGGAGGGGATTTGGGCGTCGAAACAGCGCGGACGCTCCGGATAGGA
CGCCCATAATATCCGGCTAAGACCATGGGTCTGGCTCTCGCGGGTCTGAT
TGTCTTCCACCGCGCGGGCCGCGATCAAAGACAACTAAGCATGTAGGTTC
TTGCATGGCCTGTTCTTTGGACGCGGGTTCGATTCCCGCCATCTCCACCA

TABLE 7 tmDNA Sequence for *Fibrobacter succinogenes* (*Fibrobacter*)

(SEQ ID NO: 15)
GGGGCTGATTCTGGATTCGACAGGGTTACCGAAGTGTTAGTTGCAAGTCG
AGGTCTCAGACGAGGGCTACTCGTTAAAAAGTCTGAAAAAAAATAAGTGC
TGACGAAAACTACGCACTCGCTGCCTAATTAACGGCAACGCCGGGCCTCA
TTCCGCTCCCATCGGGGTGTACGTCCGGACGCAATATGGGATAGGGAAGT
GTCATGCCTGGGGGCATCTCCCGAGATTTTCTAGGCTGGTCAAACTCCGC
GCCGACCTTCTTGGGCGTGGATAAGACGAGATCTTAAATTCGAAGGGAAC
ACTTGTAGGAACGTACATGGACGTGATTTTGGACAGGGGTTCAACTCCCG
CCAGCTCCA

TABLE 8 tmDNA Sequence for *Fusobacterium mortiferum*

(SEQ ID NO: 16)
GGGGCTGATTCTGGATTCGACGGGGTTATGAGGTTATAGGTAGCATGCCA
GGATGACCGCTGTGAGAGGTCAACACATCGTTTAGATGGAAACAGAAATT
ACGCTTTAGCTGCTTAATTAGTCAGCTCACCTCTGGTTTCTCTCTTCTGT
AGGAGAATCCAACCGAGGTGTTACCAATATACAGATTACCTTTAGTGATT
TCTCTAAGCTCAAAGGGACATTTTAGAGAATAGCTTCAGTTAGCCCTGTC
TGCGGGAGTGATTGTTGCGAAATAAAATAGTAGACTAAGCATTGTAGAAG
CCTATGGCGCTGGTAGTTTCGGACACGGGTTCAACTCCCGCCAGCTCCAA

TABLE 9 tmDNA Sequence for *Corynebacterium xerosis* (gram +, high G-C content)

(SEQ ID NO: 17)
GGGGCTGATTCTGGATTCGACTTCGTACATTGAGCCAGGGGAAGCGTGCC
GGTGAAGGCTGGAGACCACCGCAAGCGTCGCAGCAACCAATTAAGCGCCG
AGAACTCTCAGCGCGACTACGCCCTCGCTGCCTAAGCAGCGACCGCGTGT
CTGTCAGACCGGGTAGGCCTCTGATCCGGACCCTGGCATCGTTTAGTGGG
GCTCGCTCGCCGACTTGGTCGCAAGGGTCGGCGGGGACACTCACTTGCGA
CTGGGCCCGTCATCCGGTCATGTTCGACTGAACCGGAGGGCCGAGCAGAG
ACCACGCGCGAACTGCGCACGGAGAAGCCCTGGCGAGGTGACGGAGGACC
CGGGTTCAACTCCCGCCAGCTCCACCA

TABLE 10 tmDNA Sequence for *Micrococcus luteus* (parfait)

(SEQ ID NO: 18)
GGGGCTATTCTGGATTCGACGGTGTGTGTCGCGTCGGGAGAAGCGGGCCG
AGGATGCAGAGTCATCTCGTCAAACGCTCTCTGCAAACCAATAAGTGCCG
AATCCAAGCGCACTGACTTCGCTCTCGCTGCCTGATCAGTGATCGAGTCC
GTCACCCCGAGGTCGCTGTCGCCTCGGATCGTGGCGTCAGCTAGATAGCC
ACTGGGCGTCACCCTCGCCGGGGGTCGTGACGCCGACATCAATCCGGCTG
GGTCCGGGTTGGCCGCCCGTCTGCGGGACGGCCAGGACCGAGCAACACCC
ACAGCAGACTGCGCCCGGAGAAGACCTGGCAACACCTCATCGGACGCGGG
TTCAACTCCCGCANTCCCACCA

TABLE 11 tmDNA Sequence for *Mycobacterium smegmatis*

(SEQ ID NO: 19)
TCATCTCGGCTTGTTCGCGTGACCGGGAGATCCGAGTAGAGACATAGCGA
ACTGCGCACGGAGAGGGGCTGATTCCTGGATTCGACTTCGAGCATCGAAT
CCAGGGAAGCGTGCCGGTGCAGGCAAGAGACCACCGTAAGCGTCGTTGCA
ACCAATTAAGCGCCGATTCCAATCAGCGCGACTACGCCCTCGCTGCCTAA
GCGACGGCTGGTCTGTCAGACCGGGAGTGCCCTCGGCCCGGATCCTGGCA
TCAGCTAGAGGGACCCACCCACGGGTTCGGTCGCGGGACCTGTGGGGACA
TCAAACAGCGACTGGGATCGAGCCTCGAGGACATGCCGTAGGACCCGGGT
TCAACTCCCGCCAGCTCCACCA

TABLE 12 tmDNA Sequence for *Bacillus badius*

(SEQ ID NO: 20)
GGGGGTGATTCTGGATTCGACAGGGATAGTTCGAGCTTGGGCTGCGAGCC
GGAGGGCCGTCTTCGTACCAACGCAAACGCCTAAATATAACTGGCAAAAA
AGATTTAGCTTTAGCTGCCTAATATAGGTTCAGCTGCTCCTCCCGCTATC
GTCCATGTAGTCGGGTAAGGGGTCCAAACTTAGTGGACTACGCCGGAGTT
CTCCGCCTGGGGACAAAGGAAGAGATCAATCAGGCTAGCTGCCCGGACGC
CCGTCGATAGGCAAAAGGAACAGTGAACCCCAAATATATCGACTACGCTC
GTAGACGTTCAAGTGGCGTTATCTTTGGACGTGGGTTCAACTCCCGCCAG
CTCCA

TABLE 13 tmDNA Sequence for *Bacillus brevis*

(SEQ ID NO: 21)
GGGGGCGGAAAGGATTCGACGGGGATGGTAGAGCATGAGAAGCGAGCCGG
GGGGTTGCGGACCTCGTCACCAACGCAAACGCCATTAACTGGCAACAAAC
AACTTTCTCTCGCTGCTTAATAACCAGTGAGGCTCTCCCACTGCATCGGC
CCGTGTGCCGTGGATAGGGCTCAACTTTAACGGGCTACGCCGGAGGCTTC
CGCCTGGAGCCAAAGGAAGAAGACCAATCAGGCTAGGTGCCAGGTCAGCG
CGTCACTCCGCGAATCTGTCACCGAAACTCTAAACGAGTGACTGCGCTCG
GAGATGCTCATGTATCGCTGTTTTCGGACGGGGGTTCGATTCCCGCCGCC
TCACCCA

TABLE 14

| tmDNA Sequence for *Bacillus thermoleovorans* (50-60 degres) |
|---|
| (SEQ ID NO: 22) |
| GGGGGCGGAAAGGATTCGACGGGGGTAGGTCGAGCTTAAGCGGCGAGCCG |
| AGGGGGACGTCCTCGTAAAAACGTCACCTAAAGATAACTGGCAAACAAAA |
| CTACGCTTTAGCTGCCTAATTGCTGCAGCTAGCTCCTCCCGCCATCGCCC |
| GCGTGGCGTTCGAGGGGCTCATATGGAGCGGGCTACGCCCAAATCCGCCG |
| CCTGAGGATGAGGGAAGAGACGAATCAGGCTAGCCGCCGGGAGGCCTGTC |
| GGTAGGCGGAACGGACGGCGAAGCGAAATATACCGACTACGCTCGTAGAT |
| GCTTAAGTGGCGATGCCTCTGGACGTGGGTTCGATTCCCGCCGCCTCCCC |
| ACCA |

TABLE 15

| tmDNA Sequence for *Clostridium innocuum* |
|---|
| (SEQ ID NO: 23) |
| GGGGGCGGAAAGGATTCGACGGGGATATGTCTGGTACAGACTGCAGTCGA |
| GTGGTTACGTAATAACCAATTAAATTTAAACGGAAAAACTAAATTAGCTA |
| ACCTCTTTGGTGGAAACCAGAGAATGGCTTTCGCTGCTTAATAACCGATA |
| TAGGTTCGCAGCCGCCTCTGCATGCTTCTTCCTTGACCATGTGGATGTGC |
| GCGTAAGACGCAAGGGATAAGGAATCTGGTTTGCCTGAGATCAGATTCAC |
| GAAAATTCTTCAGGCACATTCATCAGCGGATGTTCATGACCTGCTGATGT |
| CTTAATCTTCATGGACTAAACTGTAGAGGTCTGTACGTGGGGCTGTTTCT |
| GGACAGGAGTTCGATTCCCGCCGCCTCACCACCA |

TABLE 16

| tmDNA Sequence for *Clostridium lentocellum* |
|---|
| (SEQ ID NO: 24) |
| GGGGGCGGAAAGGATTCGACGGGGGTCACATCTACTGGGGCAGCCATCCG |
| TAGAACGCCGGAGTCTACGTTAAAAGCTGGCACTTAAAGTAAACGCTGAA |
| GATAATTTAGCAATCGCTGCCTAATTAAGGCGCAGTCCTCCTAGGTCTTC |
| CGCAGCCTAGATCAGGGCTTCGACTCGCGGATCCTTCACCTGGCAAAGCT |
| TTGAGCCAACGTGAACACTATGAAGCTACTAAAATCTAGAGCCTGTCTTT |
| GGGCGCTAGATGGAGGGAATGTCAAAACAAAGAATATGATGGTAGAGACC |
| ACGCTATATGGGCTTTCGGACAGGGGTTCGATTCCCGCCGCCTTCACCA |

TABLE 17

| tmDNA Sequence for *Clostridium perfringens* |
|---|
| (SEQ ID NO: 25) |
| GGGGCTGATTCTGGATTCGACGGGGGTAAGATGGGTTTGATAAGCGAGTC |
| GAGGGAAGCATGGTGCCTCGATAATAAAGTATGCATTAAAGATAAACGCA |
| GAAGATAATTTTGCATTAGCAGCTTAATTTAGCGCTGCTCATCCTTCCTC |
| AATTGCCCACGGTTGAGAGTAAGGGTGTCATTTAAAAGTGGGGAACCGAG |
| CCTAGCAAAGCTTTGAGCTAGGAACGGAATTTATGAAGCTTACCAAAGAG |
| GAAGTTTGTCTGTGGACGTTCTCTGAGGGAATTTTAAAACACAAGACTAC |
| ACTCGTAGAAAGTCTTACTGGTCTGCTTTCGGACACGGGTTCAACTCCCG |
| CCACTCCA |

TABLE 18

| tmDNA Sequence for *Clostridium stercorarium* |
|---|
| (SEQ ID NO: 26) |
| GGGGGCGGAAAGGATTCGACGGGGTTATTGAAGCAAGAGTAGCGGGTAGA |
| GGATTCTCGTTGGCCTCTTTAAAAAACGAGAGCTAAAAATAAACGCAAAC |
| AACGATAACTACGCTTTAGCTGCTGCGTAAGTAACACGCAGCCCGTCGGC |
| CCCGGGGTTCCTGCGCCTCGGGATACCGGCGTCATCAAGGCAGGGAACCA |
| GCCGGATCAGGCTTCAGGTCCGGTGGGATTTAATGAAGCTACCGACTTAT |
| AAAGCCTGTCTCTGGGCGTTATAAGAAGGGAATGTCAAAACAGAGACTGC |
| ACCCGGAGAAGCTCTTGTGGATATGGTTCCGGACACGAGTTCGATTCCCG |
| CCGCCTCCACCA |

TABLE 19

| tmDNA Sequence for *Enterococcus faecium* (sp.) |
|---|
| (SEQ ID NO: 27) |
| GGGGCTGATTATGGATTCGACAGGATNGTTGAGCTTGAATTGCGTTTCGT |
| AGGTTACGGCTACGTTAAAACGTTACAGTTAAATATAACTGCTAAAAACG |
| AAAACAATTCTTTCGCTTTAGCTGCCTAAAAACCAGCTAGCGAAGATCCT |
| CCCGGCATCGCCCATGTGCTCGGGTCAGGGTCCTAATCGAAGTGGGATAC |
| GCTAAATTTTTCCGTCTGTAAAATTTAGAGGAGCTTACCAGACTAGCAAT |
| ACAAGAATGCCTGTCACTCGGCACGCTGTAAAGCGAACCTTTAAATGAGT |
| GTCTATGAACGTAGAGATTTAAGTGGGAATATGTTTTGGACGCGGGTTCA |
| ACTCCCGCCAGCTCCACCA |

TABLE 20

| tmDNA Sequence for *Heliobacillus mobilis* (photosyn/gram +) |
|---|
| (SEQ ID NO: 28) |
| GGGGCTGATTCTGGATTCGACGGGGAACGTGTTTGCTTGGGATGCGAGCC |
| GGGTTGCCGCCAGGACCGTAAAAAGGGCGGAAGGCTTTAATTGCCGAAGA |
| TAACTACGCTTTAGCTGCTTAATTGCAGTCTAACCTCTTCTCCTCTGTGC |
| TCTCGGTGAGGATGTAAGGGGTCATTTAAGAGAGCTGGCTTCGACCAATT |
| CTCGGAGGTCCAAGCGAGATTTATCGAGATAGCCTGACCAACGCTCTGTC |
| TGCCGTGCGGAAGGAAGGCGAAATCTAAAACGACAGACTACGCTCGTAGT |
| GTCCTTTGTGGGCATTTCTTCGGACGCGGGTTCAACTCCCGCCAGCTCCA |
| CCA |

TABLE 21

| tmDNA Sequence for *Heliospirillum gestii* |
|---|
| (SEQ ID NO: 29) |
| GGGGCTGATTCTGGATTCGACGGGGAACGTGTTTGCTTAGGACGCGAGCC |
| GGGTTGCCGCCAGGACCGTAAAAAGGGCGGAAGGCTTTAATTGCCGAAGA |
| TAACTACGCTTTAGCTGCTTAATTGCAGTCTAACCTCTTCTCCTCTGTGC |
| TCTCGGTGAGGATGTAAGGGGTCATTTAAGAGAGCTGGCTCGAACCAATT |
| CTCGGAGGTTCGGGTAAGACTTATCGAGATAGCCTGACCAACGCTCTGTC |
| TGCCGTGCGGAAGGATGGCGAAATCTAAAACGACAGAATACGCTCGTAGT |
| GTCCTTTGTGGGCATTTCTTCGGACGCGGGTTCAACTCCCGCCAGCTCCA |
| CCA |

TABLE 22

| tmDNA Sequence for *Lactobacillus acidophilus* |
|---|
| (SEQ ID NO: 30) |
| GGGGCTGATTCTGGATTCGACAGGCGTAGACCCGCATTGACTGCGGTTCG |
| TAGGTTACGTCTACGTAAAAACGTTACAGTTAAATATAACTGCAAATAAC |
| AAAAATTCTTACGCATTAGCTGCTTAATTTAGCGCATGCGTTGCTCTTTG |
| TCGGTTTACTCGTGGCTGACACTGAGTATCAACTTAGCGAGTTACGTTTA |
| ACTACCTCACCTGAATAGTTGAAAAGAGTCTTAGCAGGTTAGCTAGTCCA |
| TACTAGCCCTGTTATATGGCGTTTTGGACTAGTGAAGTTCAAGTAATATA |
| ACTATGATCGTAGAGGTCAGTGACGAGATGCGTTTGGACAGCGGGTTCAA |
| CTCCCGCCAGCTCCACCA |

TABLE 23

| tmDNA Sequence for *Staphylococcus epidermidis* |
|---|
| (SEQ ID NO: 31) |
| GGGGCTGATTCTGCATTCGACAGGGGTCCCCGAGCTTATTAAGCGTGTGG |
| AGGGTTGGCTCCGTCATCAACACATTTCGGTTAAATATAACTGACAAATC |
| AAACAATAATTTCGCAGTAGCTGCGTAATAGCCACTGCATCGCCTAACAG |
| CATCTCCTACGTGCTGTTAACGCGATTCAACCCTAGTAGGATATGCTAAA |
| CACTGCCGCTTGAAGTCTGTTTAGATGAAATATAATCAAGCTAGTATCAT |
| GTTGGTTGTTTATTGCTTAGCATGATGCGAAAATTATCAATAAACTACAC |
| ACGTAGAAAGATTTGTATCAGGACCTCTGGACGCGGGTTCAACTCCCGCC |
| AGCTCCACCA |

TABLE 24

| tmDNA Sequence for *Streptococcus faecium* |
|---|
| (SEQ ID NO: 32) |
| GGGGCTGATTCTGGATTCGACAGGCACAGTTTGAGCTTGAATTGCGTTTC |
| GTAGGTTACGTCTACGTTAAAACGTTACAGTTAAATATAACTGCTAAAAA |
| CGAAAACAACTCTTACGCTTTAGCTGCCTAAAAACAGTTAGCGTAGATCC |
| TCTCGGCATCGCCCATGTGCTCGAGTAAGGGTCTCAAATTTAGTGGGATA |
| CGTGACAACTTTCCGTCTGTAAGTTGTTAAAGAGATCATCAGACTAGCGA |
| TACAGAATGCCTGTCACTCGGCAAGCTGTAAAGCGAAACCACAAATGAGT |
| TGACTATGAACGTAGATTTTTAAGTGGCGATGTGTTTGGACGCGGGTTCA |
| ACTCCCGCCGTTCCACCA |

TABLE 25

| tmDNA Sequence for *Thermoanaerobacterium saccharolyticum* (*Bacillus/clostridium*) |
|---|
| (SEQ ID NO: 33) |
| GGGGTAGTAGAGGTAAAAGTAGCGAGCCGAGGTTCCATCTGCTCGTAAAA |
| CGGTGGACTTAAATATAAACGCAAACGATAATTTAGCTTACGCTGCTTAA |
| TTACAAGCAGCCGTTCAACCTTTGATTCCCACATCAAAGGATTGGGCGTC |
| GATTTAGTGGGGAACTGATTTATCAAAGCTTTGAGATAAATCGGATTTTA |
| TGAAGCTACCAAAGCAGTTATCCTGTCACTGGGAGAACTGCAGAGGGAAT |
| GTCAAAACAGTGACTGCGCTCGGAGAAGCTTTTACTGTGACACCTTCGGA |
| CCGGGGTTCAACTCCCGCCAGCTCCACCA |

TABLE 26

| tmDNA Sequence for *Mycoplasma fermentans* |
|---|
| (SEQ ID NO: 34) |
| GGGGCTGATTCTGGATTCGACATGCATTGGGTGATACTAATATCAGTAGT |
| TTGGCAGACTATAATGCATCTAGGCTTTATAATCGCAGAAGATAAAAAAG |
| CAGAAGAAGTTAATATTTCTTCACTTATGATTGCACAAAAAATGCAATCA |
| CAATCAAACCTTGCTTTCGCTTAGTTAAAAGTGACAAGTGGTTTTAAAGT |
| TGACATTTTCCTATATATTTTAAAATCGGCTTTTAAGGAGAACAGGAGTC |
| TGAAAGGGTTCCAAAAATCTATATTGTTTGCATTTCGGTAGTATAGATTA |
| ATTAGAAATGATAAACTGTAAAAAGTATTGGTATTGACTTGGTGTGTGGA |
| CTCGGGTTCAACTCCCGCCAGCTCCACCA |

TABLE 27

| tmDNA Sequence for *Mycoplasma hyorhinis* |
|---|
| (SEQ ID NO: 35) |
| GGGGCTGATTCTGGATTCGACATACATAAAAGGATATAAATTGCAGTGGT |
| CTTGTAAACCATAAGACAATTTCTTTACTAAGCGGAAAAGAAAACAAAAA |
| AGAAGATTATTCATTATTAATGAATGCTTCAACTCAATCAAATCTAGCTT |
| TTGCATTTTAAAAAACTAGTAGACCAATTTGCTTCTCACGAATTGTAATC |
| TTTATATTAGAGAATAGTTAAAAATCTGATCACTTTTTAATGAATTTATA |
| GATCACAGGCTTTTTTAATCTTTTTGTTATTTTAGATAAAGAGTCTTCTT |
| AAAAATAACTAAACTGTAGGAATTTATATTTAATTATGCGTGGACCCGGG |
| TTCAACTCCCGCCAGCTCCACCA |

TABLE 28

| tmDNA Sequence for *Mycoplasma pirum* |
|---|
| (SEQ ID NO: 36) |
| GGGGAGTCATGGTTTTGACATGAATGATGGACCCATAGAGGCAGTGGGGT |
| ATGCCCCTTATAGCTCAAGGTTTAAATTAACCGACAAAACTGACGAAAAC |
| GTTGCCGTTGATACAAATTTATTAATCAACCAACAAGCTCAATTTAACTA |
| CGCATTTGCATAGTATAAAAAAATAAATTGTGCTACTCATTGTAATTAGG |
| TTACTAAATTACTTTGTTTTATATAGTCCTGTAACTAGTTCTAGTGATGT |
| CTATAAACTAGAATGAGATTTATAGACTTATTTGTTGGCGGTTGTGCCAT |
| AGCCTAAATCAACAAAGACAATTTATTTATGGTACTAAACTGTAGATTCT |
| ATGATGAAATTATTTGTGGAAACGGGTTCGATTCCCGCCATCTCCACCA |

TABLE 29

| tmDNA Sequence for *Mycoplasma salivarium* |
|---|
| (SEQ ID NO: 37) |
| GGGGCTGATTCTGGATTCGACAGGCATTCGATTCATTATGTTGCAGTGGT |
| TTGCAAACCATAAGGCACTAGGCTTTTTAAACGCAAAAGACCAAAAAAC |
| AGAAGATCAAGCAGTTGATCTAGCATTTATGAATAATTCACAAATGCAAT |
| CAAATCTAGTTTTCGCTTAGTAAAATTAGTCAATTTATTATGGTGCTCAA |
| CATAATAAATGGTAGTATGAGCTTAATATCATATGATTTTAGTTAATATG |
| ATAGGATTTGTAACTAAACTATGTTATAGAAATTTGTAAATTATATATAT |
| GACATAGGAAATTTAATTTACTAAACTGTAGATGCATAATGTTGAAGATG |
| TGTGGACCGGGGTTCAACTCCCGCCAGCTCCACCA |

TABLE 30

| tmDNA Sequence for *Herpetosiphon aurantiacus* |
|---|
| (SEQ ID NO: 38) |
| GGGGGCGGAAAGGATTCGACGGGGAGGGCCAATCGTAAGTGGCAAGCCGA |
| GACGCTGAGCCTCGTTAAATCGGCAACGCCATTAACTGGCAAAAACACTT |
| TCCGCGCTCCTGTAGCGCTTGCTGCCTAATTAAGGCAACACGTCTCTACT |
| AGCCTCAGCCCGATGGGCTTGTAGCGGCGACACTTAGTCGGGTCGCTCCC |
| CTAGTTATGTCTGTGGGCTAGGGGCTAAGATTAACAGGCTGGTCGTGGCC |
| CGCTTTGTCTATCGGGTGGTGCACCGATAAGATTTAATCAATAGACTACG |
| CTTGTAGATGCTTGCGGTTTAACTTTTTGGACGCGGGTTCGATTCCCGCC |
| GCCTCACCACCA |

TABLE 31

| tmDNA Sequence for *Thermomicrobium roseum* (352 nts, temp. 70 degrees, green non sulfur) |
|---|
| (SEQ ID NO: 39) |
| GGGGCTGATTCTGGATTCGACAGGGCCGTAGGTGCGAGGATTGCAGGTCG |
| AGGTCGCCCACGGACTCGTAAAAAGGGGCAGCCAAGTAACTGGCGAGCGC |
| GAACTCGCTCTGGCTGCGTAATTCACGCAGCCACGTCTGCCCGGACCCTT |
| CCCTGGTGGGTTCGGAGCGGGCGCCGCAAGACCGGGGTGCCCCTGGCCCA |
| AGCGCCGGTGCGGGCCAGGTCAAGCGTGATCCGGCTCGGCTGACCGGGAT |
| CCTGTCGGTGGGAGCCTGGCAGCGACAGTAGAACACCGACTAAGCCTGTA |
| GCATATCCTCGGCTGAACGCTCTGGACGCGGGTTCAACTCCCGCCAGCTC |
| CACCA |

TABLE 32

| tmDNA Sequence for *Chlorobium limicola* |
|---|
| (SEQ ID NO: 40) |
| GGGGCTGATTCTGGATTCGACAGGATACGTGTGAGATGTCGTTGCACTCC |
| GAGTTTCAGCATGGACGGACTCGTTAAACAAGTCTATGTACCATTAGATG |
| CAGACGATTATTCGTATGCAATGGCTGCCTGATTAGCACAAGTTAACTCA |
| GACGCCATCGTCCTGCGGTGAATGCGCTTACTCTGAAGCCGCCGGATGGC |
| ATAACCCGCGCTTGAGCCTACGGGTTCGCGCAAGTAAGCTCCGTACATTC |
| ATGCCCGAGGGGCTGTGCGGGTAATTTCTCGGGATAAGGGGACGAACGCT |
| GCTGGCGGTGTAATCGGCCCACGAAAACCCAATCACCAGAGATGAGTGTG |
| GTGACTGCATCGAGCAGTGTTTTGGACGCGGGTTCAACTCCCGCCAGCTC |
| CACCA |

TABLE 33

| tmDNA Sequence for *Pirellula staleyi* (*planctomyces*) |
|---|
| (SEQ ID NO: 41) |
| GGGGCTGATTCTGGATTCGACCGGATAGCCTGAAGCGAATACGGCGTGCC |
| GTGGTTGATCAGATGGCCACGTAAAAAGCTGATCACAAACTTAACTGCCG |
| AGAGCAATCTCGCACTTGCTGCCTAACTAAACGGTAGCTTCCGACTGAGG |
| GCTTTAGCCGGAGAGGCCCAAAAGTTGGTCACCAAATCCGGACCGCCTCG |
| TGCCATGATCGAAACGCACGAGGTCAAAAAAGTTTCGATCTAGTGCAGGG |
| TGTAGCCAGCAGCTAGGCGACAAACTGTGCAAAAATCAAATTTTCTGCTA |
| CGCACGTAGATGTGTTCGTGAAAATGTCTCGGGACGGGGGTTCAACTCCC |
| GCCACTCCACCA |

TABLE 34 tmDNA Sequence for *Planctomyces limnophilus*

(SEQ ID NO: 42)
GGGGCTGATTCTGGATTCGACAACCTCTCAAGAGGAGCGTGGCCACTATG
GGACTCGATTATGTTGAATTCGTCATGGATCTTGAAGAGACCTTCGACAT
CAAACTGGATGACAAACATTTTTCAGCAGTCAAAACACCACGCGATTTGG
CAATCATTATTCGGGATCAATTAGCTGCTGAAGGCAGAATCTGGGATGAA
TCGAATGCTTTTCGCAAAATCTCGAATTTGAATTGGACGATGTTGCCCGA
GTTCCGGATGTGGACTCAAATCAAAAGCTCTCTACCAGTTTCTTTTCACC
GACTGCGTCCCAGCACCCGTCTCGTTCAACTCCCGCCANTCCACCA

TABLE 35 tmDNA Sequence for *Planctomyces maris*

(SEQ ID NO: 43)
GGGGCTGATTCTGGATTCGACTGGTTCACCGTATGTTAAGGTGGCGGTGC
CGTGGTTGATCAGTTGGCCACGTAAAAAGCTGATCACAATCTAATTGCAA
ACAAGCAATTTTCAATGGCTGCTTAATAAAAGCAACCCCGGCTTAGGAAT
CTCTGTCTGAGGAGTCCGACAGCTGGTCACAAAATCAGACTGGTATCAGA
TCAATGTCCGCTCCGTCTGATACGAGATTCGTGGTGGACTGGTTTCCAAC
AGGCTCTGTTTATCGTGCCCGAAGAAACGAGACTCAAACGATAAAATATG
CACCGTAGAGGCTTTAGCTGAGGGTTCACAGGACGCGGGTTCAACTCCCG
CCAGCTCCACCA

TABLE 36 tmDNA Sequence for *Alcaligenes eutrophus*

(SEQ ID NO: 44)
GGGGTTGATTCTGGATTCGACGTGGGTTACAAAGCAGTGGAGGGCATACC
GAGGACCCGTCACCTCGTTAATCAATGGGAATGCAATAACTGCTAACGAC
GAACGTTACGCACTGGCCGCTTAATTGCGGCCGTCCTCGCACTGGCTCGC
TGACGGGCTAGGGTCGCAAGACCACGCGAGGTCATTTACGTCAGATAAGC
TCCGGAAGGGTCACGAAGCCGGGGACGAAAACCTAGTGACTCGCCGTCGT
AGAGCGTGTTCGTCCGCGATGCGCCGGTTAAATCAAATGACAGAACTAAG
TATGTAGAACTCTCTGTGGAGGGCTTACGGACGCGGGTTCAACTCCCGCC
AGCTCCACCA

TABLE 37 tmDNA Sequence for *Alcaligenes faecalis* (beta proteobacteria)

(SEQ ID NO: 45)
GGGGGCGGAAAGGATTCGACGGGGGTCAAGAAGCAGCACAGGGCGTGTCG
AGCACCAGTACGCTCGTAAATCCACTGGAAAACTATAAACGCCAACGACG
AGCGTTTCGCTCTAGCCGCTTAAGGCTGGGCCACTGCACTAATTTGTCTT
TGGGTTAGGTAGGGCAACCTACAGCAGTGTTATTTACAAAGAATCGAATC
GGTCTGCGCCACGAAGTCCGGTTCTAAAACTTAGTGGATCGCCAAGGAAA
GGCCTGTCAATTGGCATAGTCCAAGGTTAAAACTTAAAATTAATTGACTA
CACATGTAGAACTGTCTGTGGACGGCTTGCGGACGGGGGTTCGATTCCCG
CCGCCTCCACCA

TABLE 38 tmDNA Sequence for *Chromobacterium violaceum* (beta-purple)

(SEQ ID NO: 46)
GGGGCTGATTCTGGATTCGACGGGGGTTGCGAAGCAGATGAGGGCATACC
GGGATTTCAGTCACCCCGTAAAACGCTGAATTTATATAGTCGCAAACGAC
GAAACTTACGCTCTGGCAGCCTAACGGCCGGCCAGACACTACAACGGTTC
GCAGATGGGCCGGGGGCGTCAAAACCCTGTAGTGTCACTCTACATCTGCT
AGTGCTGTTCCGGGTTACTTGGTTCAGTGCGAAATAATAGGTAACTCGCC
AAAGTCCAGCCTGTCCGTCGGCGTGGCAGAGGTTAAATCCAAATGACACG
ACTAAGTATGTAGAACTCACTGTAGAGGACTTTCGGACGCGGGTTCAACT
CCCGCCAGCTCCACCA

TABLE 39 tmDNA Sequence for *Hydrogenophaga palleroni* (beta-purple)

(SEQ ID NO: 47)
GGGGCTGATTCTGGATTCGACGTGGGTTCGGACGCGCAGCAGGGCATGTC
GAGGTTCTGTCACCTCGTAAATCAGCAGAAAAAAACCAACTGCAAACGAC
GAACGTTTCGCACTCGCCGCTTAAACACCGGTGAGCCTTGCAACAGCAGG
CCGATGGGCTGGGCAAGGGGGTCGCAAGACCTCCCGGCTGCAAGGTAATT
TACATCGGCTGGTTCTGCGTCGGGCACCTTGGCGCAGGATGAGATTCAAG
GATGCTGGCTTCCCGTTTAGCGTGCCACTGCGCGACTCGGGCGGCGAGAC
CCAAATCAGACGGCTACACATGTAGAACTGCTCGAAAAAGGCTTGCGGAC
GGGGGTTCAACTCCCGCCAGCTCCACCA

TABLE 40 tmDNA Sequence for *Methylobacillus glycogenes* (beta-purple)

(SEQ ID NO: 48)
GGGGGCGGAAAGGATTCGACGGGGGTTGCAAAGCAGCGCAGGGCATACCG
AGGCCTAGTCACCTCGTAAATAAACTAGAACAAGTATAGTCGCAAACGAC
GAAACTTACGCTCTAGCCGCTTAATCCCGGCTGGACGCTGCACCGAAGGG
CCTCTCGGTCGGGTGGGGTAACCCACAGCAGCGTCATTAAGAGAGGATCG
TGCGATATTGGGTTACTTAATATCGTATTAAATCCAAGGTAACTCGCCTG
CTGTTTGCTTGCTCGTTGGTGAGCATCAGGTTAAATCAAACAACACAGCT
AAGTATGTAGAACTGTCTGTGGAGGGCTTGCGGACGGGGGTTCGATTCCC
GCCGCCTCACCACCA

TABLE 41 tmDNA Sequence for *Nitrosomonas cryotolerans* (beta-purple)

(SEQ ID NO: 49)
GGGGCTGATTCTGGATTCGACGTGGGTTGCAAAGCAGCGCAGGGCATACC
GAGGACCAGAATACCTCGTAAATACATCTGGAAAAAAATAGTCGCAAACG
ACGAAAACTACGCTTTAGCCGCTTAATACGGCTAGCCTCTGCACCGATGG
GCCTTAACGTCGGGTCTGGCAACAGACAGCAGAGTCATTAGCAAGGATCG
CGTTCTGTAGGGTCACTTTACAGAACGTTAAACAATAGGTGACTCGCCTG
CCATCAGCCCGCCAGCTGGCGGTTGTCAGGTTAAATTAAAGAGCATGGCT
AAGTATGTAGAACTGTCTGTAGAGGACTTGCGGACGCGGGTTCAACTCCC
GCCAGTCCACCA

TABLE 42 tmDNA Sequence for *Pseudomonas testosteroni*

(SEQ ID NO: 50)
GGGGCTGATTCTGGATTCGACGTGGGTTCGGGACCGGTGCGGTGCATGTC
GAGCTTGAGTGACGCTCGTAAATCTCCATTCAAAAAACTAACTGCAAACG
ACGAACGTTTCGCACTCGCCGCTTAATCCGGTGAGCCTTGCAACAGCACG
CTAGTGGGCTGGGCAAGGGGGTAGCAATACCTCCCGGCTGCAAGGGAATT
TTCATTAGCTGGCTGGATACCGGGCTTCTTGGTATTTGGCGAGATTTTAG
GAAGCTGGCTACCCAAGCAGCGTGTGCCTGCGGGGTTTGGGTGGCGAGAT
TTAAAACAGAGCACTAAACATGTAGATCTGTCCGGCGAAGGCTTACGGAC
GCGGGTTCAACTCCCGCCAGCTCCACCA

TABLE 43 tmDNA Sequence for *Ralstonia pickettii* (*Burkholderia*)

(SEQ ID NO: 51)
GGGGGCGGAAAGGATTCGACGGGGGTTGCGAAGCAGCGGAGGGCATACCG
AGGACCCGTCACCTCGTTAATCAATGGGAATGCAATAACTGCTAACGACG
AACGTTACGCACTGGCAGCCTAAGGGCCGCCGTCCTCGCACTGGCTCGCT
GACGGGCTAGGGTCGCAAGACCAGCGAGGTCATTTACGTCAGATAAGCTT
TAGGTGAGTCACGGGCCTAGAGACGAAAACTTAGTGAATCGCCGTCGTAG
AGCGTGTTCGTCCGCGATGCGGCGGTTAAATCAAATGACAGAACTAAGTA
TGTAGAACTCTCTGTGGAGGGCTTGCGGACGCGGGTTCGATTCCCGCCGC
CTCACCACCA

TABLE 44

| tmDNA Sequence for *Variovax paradoxus* (*pseudomonas* sp.) |
|---|
| (SEQ ID NO: 52) |
| GGGGCTGATTCTGGATTCGACGTGGGTTCGGAGTCGCAGCGGGGCATGTC |
| GAGCTGAATGCGCTCGTAAAACAGATTCAAACAAACTAACTGCAAACGAC |
| GAACGTTTCGCACTCGCTGCTTAATTGCCAGTGAGCCTTGCAACAGTTGG |
| CCGATGGGCTGGGCAAGGGGGTCTGGAGCAATCCTGACCTCCCGGCTGCA |
| AGGATAACTACATGGGCTGGCTCCGATCCGGGTACCTTGGGTCGGGGCGA |
| GAAAATAGGGTACTGGCGTCCGGTTTAGCGTGTGACTGCGCGACTCCGGA |
| AGCGAGACTCAAAACAGATCACTAAACATGTAGAACTGCGCGATGAAGGC |
| TTGCGGACGGGGGTTCAACTCCCGCCAGCTCCACCA |

TABLE 45

| tmDNA Sequence for *Bdellovibrio bacteriovorus* (delta proteobacterie) |
|---|
| (SEQ ID NO: 53) |
| GGGGGCGGAAAGGATTCGACGGGGGTGCTGAAGCATAAGGAGCATACCGG |
| GGCGGATGAGGACCTCGTTAAAAACGTCCACTTTGTAATTGGCAACGATT |
| ACGCACTTGCAGCTTAATTAAGCAGCACGATCAACCTTGTGGTGGTTCCG |
| CACTTGGATTGATCGTCATTTAGGGACCTCGGCGTGTTGGGTTTTCTCCA |
| GCAGACATGCTTAAATTTACTGGGGGAGAGGTCTTAGGGATTTTGTCTGT |
| GGAAGCCCGAGGACCAATCTAAAACACTGACTAAGTATGTAGCGCCTTAT |
| CGTGGATCATTTGCGGACGGGGGTTCGATTCCCGCCGCCTCCACCA |

TABLE 46

| tmDNA Sequence for *Myxococcus xanthus* (delta proteobacterie) |
|---|
| (SEQ ID NO: 54) |
| GGGGGCGGAAAGGATTCGACGGGGGCATTGAAGTTCGAGACGCGTGCCGA |
| GCTTGTCAGGTAGCTCGTAAATTCAACCCGGCAAAGACACAAAAGCCAAC |
| GACAACGTTGAGCTCGCGCTGGCTGCCTAAAAACAGCCCATAGTGCGCGG |
| TCCCCCCGCCCTCGGCCTGTGGGGTTGGGACAGACCGTCATAATGCAGGC |
| TGGCTGCCGAGGGTGCCTGGACCCGAGGTGGCGAGATCTTCCCAGGACCG |
| GCTCTGAGTATCCCGTCCGTGGGAGCCTCAGGGACGTAGCAAATCGCGGA |
| CTACGCACGTAGGGTCGAAGAGCGGACGGCTTTCGGACGCGGGTTCGATT |
| CCCGCCGCCTCCACCA |

TABLE 47

| tmDNA Sequence for *Sulfurospirillum Deleyianum* |
|---|
| (SEQ ID NO: 55) |
| GGGGCTGATTCTGGATTCGACAGGAGTAGTTTTAGCTTATGGCTGCATGT |
| CGGGAGTGAGGGTCTTCCGTTACACAACCTTCAAACAATAACTGCTAACA |
| ACAGTAACTATCGTCCTGCTTACGCGCTAGCTGCGTAAGTTTAACAAATA |
| ATGGACTGCTCTCCCCTTTGATGCTATCTTAGGAGGTCTTGGAGAGTATC |
| ATAGATTTGATAGCTATATTACATGAACGCCTTTACATGTAATGAAGTTA |
| AAGGCTCGTTTTGCGTAGTTTTCTGATTGTTGTACGAAGCAAAATTAAAC |
| ACTATCAACAATATCTAAGCATGTAGACGTCATAGGTGGCTATTTTTGGA |
| CTGCGGGTTCAACTCCCGCCAGCTCCACCA |

TABLE 48

| tmDNA Sequence for *Chromatium vinosum* |
|---|
| (SEQ ID NO: 56) |
| GGGGCTGATTCTGGATTCGACGTGGGTCGCGAAACCTAAGGTGCATGCCG |
| AGGTGCGGTTGACCTCGTAAAACCCTCCGCAAACTTATAGTTGCCAACGA |
| CGACAACTACGCTCTCGCTGCTTAATCCCAGCGGGCCTCTGACCGTCACT |
| TGCCTGTGGGCGGCGGATTCCAGGGGTAACCTCACACAGGATCGTGGTGA |
| CGGGAGTCCGGACCTGATCCACTAAAACCTAACGGAATCGCCGACTGATC |
| GCCCTGCCCTTCGGGCGGCAGAAGGCTAAAAACAATAGAGTGGGCTAAGC |
| ATGTAGGACCGAGGGCAGAGGGCTTGCGGACGCGGGTTCAACTCCCGCCA |
| GCTCCACCA |

TABLE 49

| tmDNA Sequence for *Pseudomonas fluorescens* (gamma proteobacteria) |
|---|
| (SEQ ID NO: 57) |
| GGGGCTGATTCTGGATTCGACGCCGGTTGCGAACCTTTAGGTGCATGCCG |
| AGTTGGTAACAGAACTCGTAAATCCACTGTTGCAACTTTCTATAGTTGCC |
| AATGACGAAACCTACGGGGAATACGCTCTCGCTGCGTAAGCAGCCTTAGC |
| CCTTCCCTCCTGGTACCTTCGGGTCCAGCAATCATCAGGGGATGTCTGTA |
| AACCCAAAGTGATTGTCATATAGAACAGAATCGCCGTGCAGTACGTTGTG |
| GACGAAGCGGCTAAAACTTACACAACTCGCCCAAAGCACCCTGCCCGTCG |
| GGTCGCTGAGGGTTAACTTAATAGACACGGCTACGCATGTAGTACCGACA |
| GCAGAGTACTGGCGGACGCGGGTTCAACTCCCGCCAGCTCCACCA |

TABLE 50

| tmDNA Sequence for *Borrelia afzeli* |
|---|
| (SEQ ID NO: 58) |
| GGGGCTGATTCTGGATTCGACTGAAAATGCTAATATTGTAAGTTGCAAGC |
| AGAGGGAATCTCTTAAAACTTCTAAAATAAATGCAAAAAATAATAACTTT |
| ACAAGTTCAAACCTTGTAATGGCTGCTTAAGTTAGCAGAGAGTTTTGTTG |
| AATTTGGCTTTGAGATTCACTTATACTCTTTTAGACATCGAAGCTTGCTT |
| AAAAATGTTTTCAAGTTGATTTTTAGGGACTTTTATACTTGAGAGCAATT |
| TGGCGGTTTGCTAGTATTTCCAAACCATATTGCTTAGTAAAATACTAGAT |
| AAGCTTGTAGAAGCTTATAGTATTGTTTTTAGGACGCGGGTTCAACTCCC |
| GCCAGTCCACCA |

TABLE 51

| tmDNA Sequence for *Borrelia crociduarae* |
|---|
| (SEQ ID NO: 59) |
| GGGGCTGATTCTGGATTCGACTAAGAACTTTAGTAGCATAAATGGCAAGC |
| AGAGTGAATCTCTTAAAACTTCTTTAATAAATGCAAAAAATAATAACTTT |
| ACAAGTTCAGATCTTGTAATGGCTGCTTAATTTAGCAGAGAGTTTTGTTG |
| GATTTTGCTTTGAGGTTCAACTTATACTCTTTAAGACATCAAAGTATGCC |
| TAAAAATGTTTCAAGTTGATTTTTAGGGACCTTTAAACTTGAGAGTAATT |
| TGGTGGTTTGCTTGTTTTCCAAGCCTTATTGCTTTTTCTAAAAATTAGCT |
| AAGCTTGTAGATATTTATGATATTATTTTTAGGACGCGGGTTCAACTCCC |
| GCCAGTTCCACCA |

TABLE 52

| tmDNA Sequence for *Borrelia hermsii* |
|---|
| (SEQ ID NO: 60) |
| GGGGCTGATTCTGGATTCGACTAAAAACTTTAGTAGCATAAATTGCAAGC |
| AGAGGGAATCTCTTAAAACTTCTTTAATAAATGCAAGAAATAATAACTTT |
| ACAAGTTCAAATCTTGTAATGGCTGCTTAAATTAGCAGAGAGTTCTGCTG |
| GATTTTGCTTTGAGGTTCAGCTTATACTCTTTTAAGACATCAAAGCTTGC |
| TTAAAAATATTTCAAGTTGATTTTTAGGGACTTTTAAATTTGAGAGTAAT |
| TTGGCGGTTTGCTAGTTTTTCCAAACCTTATTACTTAAAGAAAACACTAG |
| CTAAGCTTGTAGATATTTATGATATTATTTTTAGGACGCGGGTTCAACTC |
| CCGCCAGCTCCACCA |

TABLE 53

| tmDNA Sequence for *Borrelia garinii* |
|---|
| (SEQ ID NO: 61) |
| GGGGCTGATTCTGGATTCGACTGAAAATGCGAATATTGTAAGTTGCAGGC |
| AGAGGGAATCTCTTAAAACTTCTAAAATAAATGCAAAAAATAATAACTTT |
| ACAAGCTCAAACCTTGTAATGGCTGCTTAAGTTAGCAGGGAGTTTCGTTG |
| AATTTGGCTTTGAGGTTCACTTATACTCTTTTCGATATCGAAGCTTGCTT |
| AAAAATGTTTTCAAGTTAATTTTTAGGGACTTTTGTACTTGAGAGCAATT |
| TGGCGGTTTGCTAGTATTTCCAAACCATATTGCTTAAGTAAAATGCTAGA |
| TAAGCTTGTAGAAGCTTATAATATTGTTTTTAGGACGCGGGTTCAACTCC |
| CGCCAGTCCACCA |

TABLE 54

| tmDNA Sequence for *Thermodesulfobacterium commune* (70 degrees) |
|---|
| (SEQ ID NO: 62)<br>GGGGGCGGAAAGGATTCGACGGGGATAGGTAGGATTAAACAGCAGGCCGT<br>GGTCGCACCCAACCACGTTAAATAGGGTGCAAAAACACAACTGCCAACGA<br>ATACGCCTACGCTTTGGCAGCCTAAGCGTGCTGCCACGCACCTTTAGACC<br>TTGCCTGTGGGTCTAAAGGTGTGTGACCTAACAGGCTTTGGGAGGCTTAA<br>TCGGTGGGGTTAAGCCTCCCGAGATTACATCCCACCTGGTAGGGTTGCTT<br>GGTGCCTGTGACAAGCACCCTACGAGATTTTCCCACAGGCTAAGCCTGTA<br>GCGGTTTAATCTGAACTATCTCCGGACGCGGGTTCGATTCCCGCCGCCTC<br>CCCACCA |

TABLE 55

| tmDNA Sequence for *Thermotoga neapolitana* (*Thermotogales*) |
|---|
| (SEQ ID NO: 63)<br>GGGGGCGGAAAGGATTCGACGGGGATGGAGTCCCCTGGGAAGCGAGCCGA<br>GGTCCCCACCTCCTCGTAAAAAAGGTGGGAACACGAATAAGTGCCAACGA<br>ACCTGTTGCTGTTGCCGCCTAATAGATAGGCGGCCGTCCTCTCCGGAGTT<br>GGCTGGGCTCCGGAAGAGGGCGTGAGGGATCCAGCCTACCGATCTGGGCT<br>CCGCCTTCCGGCCCGGATCGGGAAGGTTCAGGAAGGCTGTGGGAAGCGAC<br>ACCCTGCCCGTGGGGGGTCCTTCCCGAGACACGAAACACGGGCTGCGCTC<br>GGAGAAGCCCAGGGGCCTCCATCTTCNGACGCGGGTTCGATTCCCGCCAC<br>CTCCACCA |

TABLE 56

| tmDNA Sequence for *Deinococcus proteolyticus* |
|---|
| (SEQ ID NO: 64)<br>GGGGGCGGAAAGGATTCGACGGGGGAACGGAAAGCGCTGCTGCGTGCCGA<br>GGAGCCGTTGGCCTCGTAAACAAACGGCAAAGCCATTAACTGGCGAAAAT<br>AACTACGCTCTCGCTGCTTAAGTGAGACAGTGACCACGTAGCCCCGCCTT<br>TGGCGACGTGTGAACTGAGACAAAAGAAGGCTAGCTTAGGTGAGGTTCCA<br>TAGCCAAAAGTGAAACCAAATGGAAATAAGGCGGACGGCAGCCTGTTTGC<br>TGGCAGCCCAGGCCCGACAATTTAAGAGCAGACTACGCACGTAGATGCAC<br>GCTGGATGGACCTTTGGACGCGGGTTCGATTCCCGCCAGCTCCACCA |

TABLE 57

| tmDNA Sequence for *Prosthecobacter fusiformis* (*verrucomicrobia*) |
|---|
| (SEQ ID NO: 65)<br>GGGGCTGATTCTGGATTCGACGGGGAGTACAAGGATCAAAAGCTGCAAGC<br>CGAGGTGCCGTTACCTCGTAAAACAACGGCAAAAAAGAAGTGCCAACACA<br>AATTTAGCATTAGCTGCTTAATTTAGCAGCTACGCTCTTCTAACCCGGGC<br>TGGCAGGGTTAGAAGGGTGTCATAATGAGCCAGCTGCCCCTTCCGACTCC<br>CCTAAGGAAGGGAAAGATGTAGGGGATAGGTGCTTACAGAATCCTGCGGG<br>AGGGAGTCTGTAAGTGCCGAAAAGTTAAAACTCCCGCTAAGCTTGTAGAG<br>GCTTTTGATTCTTGCTCTCTGGACGCGGGTTCAACTCCCGCCAGCTCCAC<br>CA |

TABLE 58

| tmDNA Sequence for *Verrucomicrobium spinosum* (*verrucomicrobium*) |
|---|
| (SEQ ID NO: 66)<br>GGGNNNNATTTGGAATTCGCCGAATGCTAGAAGTGGAGGCTGCATGCCGC<br>GGATGATTCGTTGGCCGCTTTACCAATTCGGATCAAACAACTAAATGCGG<br>ACTCTAACGAGCTTGCCCTCGCCGCTTAATTGACGGTGACGTTCCTCCAG<br>TGAAGTCTGTGAATTGGAGGAGCGACTACTTACAGGCTGGCCAAAAGAGC<br>GGGCGACCGGCCCCAAGGCGAGATCTACAGGCCGCTGGATGGACGGCATC<br>CTGGCAGTAGGAGGCTGGACATCGAGATCAAATNATTGCCTGAGCATGGA<br>GACGCTTTCATAAAGGNGTTCGGACAGGG |

Example 4

Alignment of tmRNA Sequences

The newly discovered tmRNA sequences and several known tmRNA sequences were aligned to identify target sites for drug development. The alignments of the sequences are shown in FIGS. 3A-11B. The nucleotides in the tmRNA sequences of these figures exist in several motifs (Felden et al., 1999). These motifs include nucleotides considered to be in RNA helices (Watson-Crick base-pairs GC or AU, or GU Wobble base-pairs). Nucleotides that are in single stranded RNA domains, hence not base-paired. Some nucleotides in the single stranded domains are universally conserved nucleotides. Other nucleotides are the exceptions to a quasi-sequence conservation in the sequences alignment. Several nucleotides exist in well established non-canonical structural motifs in RNA structures; for example AG-GA pairs, AA pairs, etc. Some nucleotides are universally conserved Wobble GU base-pairs.

All the gene sequences have been decomposed in several structural domains that have been indicated with names at the top of each block of sequences. These domains are respectively from the 5'-end to the 3'-end of the sequences: H1, H5, H2, PK1, H4, PK2, PK3, PK4, H5 and H6. The bars delineate all the structural domains. H means helices and PK means pseudoknot. A pseudoknot is made of the pairing of parts of an RNA-loop with an upstream sequence. Consequently, two helices are made (shown in Felden et al., 1999) for all the 4 pseudoknots PK1 to PK4 for each sequence. Moreover, the tRNA-like domain as well as the coding sequence, namely the two functional units of the molecule, have also been indicated for each sequence.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria.

Common Structural Features for Drug Targeting:

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. The PK1 structural domain is strictly conserved in the tmRNAs and is located upstream of the coding sequence. Since these pseudoknots are not found in all canonial transfer RNAs, they can also be targeted with specific drugs. Disruption of either PK1 or PK2 or PK3 with a specific drug would lead to inactive tmRNA molecules in vivo.

Specific Structural Features in Each Phylum that could be Targeted by Drugs:

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding, which has been shown for *Escherichia coli*, and thus, is also available for interaction with other drugs. Moreover, this is a critical functional domain of the molecule in its quality-control mechanism in cells. In addition, this coding sequence would be the ideal target to use for designing specific PCR-based diagnostic assays for infection diseases.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future anti-bacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Andersson, S. G. et al. (1998). *Nature* 396:133-140.
Ando, H. et al. (1996). *Genes & Genet. Syst.* 71:47-50.
Breithaupt, H. (1999). *Nature Biotechnol.* 17:1165-1169.
Felden, B. et al. (1996). *Biochimie* 78:979-983.
Felden, B. et al. (1997). *RNA* 3:89-103.
Felden, B. et al. (1998). *EMBO J.* 17:3188-3196.
Felden et al. (1999). *Biochim. Biophys. Acta* 1446:145-148.
Gray, M. W. and Spencer, D. F.(1996). In *Evolution of Microbial Life*, Cambridge University Press, pp. 109-126.
Hickerson, R. P. et al. (1998). *J. Mol. Biol.* 279:577-587.
Himeno, H. et al. (1997). *J. Mol. Biol.* 268:803-808.
Huang, C. et al. (2000). *EMBO J.* 19:1098-1107.
Julio, S. M et al. (2000). *J. Bacteriol.* 182:1558-1563.
Keiler, K. C. et al. (1996). *Science* 271:990-993.
Komine, Y. et al. (1994). *Proc. Natl. Acad. Sci. USA* 20:9223-9227.
Mateeva, O. et al. (1997). *Nucleic Acids Res.* 25:5010-5016.
Muto, A. et al. (1998). *Trends Biochem. Sci.* 1:25-29.
Nameki, N. et al. (1999). *J. Mol. Biol.* 286:733-744.
Nakemi, N. et al. (2000). *FEBS Lett.* 470:345-349.
*Remington's Pharmaceutical Sciences,* 18th Ed., Mack Publishing Co., Easton, Pa., 1990.
Tu, G. F. et al. (1995). *J. Biol. Chem.* 270:9322-9326.
Ushida, C. et al. (1994). *Nucleic Acids Res.* 16:3392-3396.
Williams, K. P. (1999). *Nucleic Acids Res.* 27:165-166.
Williams, K. P. and Bartel, D. P. (1996). *RNA* 2:1306-1310.
Wower, J. and Zwieb, C. (1999). *Nucleic Acids Res.* 27:167.
Yang, D. et al. (1985). *Proc. Natl. Acad. Sci. USA* 82:4443-4447.

What is claimed is:

1. An isolated nucleic acid sequence selected from the group consisting of a tmRNA sequence for *Chlamydia trachomatis* a DNA sequence consisting of a tmDNA sequence encoding said tmRNA sequence, and a DNA sequence consisting of a full-length complement of said tmDNA sequence, wherein the tmRNA sequence for *Chlamydia trachomatis* is the sequence set forth in SEQ ID NO: 129.

2. A method for diagnosing a bacterial infection associated with *Chlamydia trachomatis* comprising determining the presence of a bacterial nucleic acid sequence selected from the group consisting a tmRNA sequence for *Chlamydia trachomatis* a DNA sequence consisting of a tmDNA sequence encoding said tmRNA sequence, and a DNA sequence consisting of a full-length complement of said tmDNA sequence, wherein the tmRNA sequence for *Chlamydia trachomatis* is the sequence set forth in SEQ ID NO: 129.

3. The method of claim 2, wherein the determination is made by performing an amplification-based assay.

4. The isolated nucleic acid sequence of claim 1, wherein the nucleic acid sequence is the DNA sequence consisting of the tmDNA sequence encoding the tmRNA sequence for *Chlamydia trachomatis.*

5. The method of claim 2, wherein the bacterial nucleic acid sequence is the DNA sequence consisting of the tmDNA sequence encoding the tmRNA sequence for *Chlamydia trachomatis.*

6. The method of claim 3, wherein the bacterial nucleic acid sequence is the DNA sequence consisting of the tmDNA sequence encoding the tmRNA sequence for *Chlamydia trachomatis.*

* * * * *

SEQUENCE LISTING

```
<160> NUMBER OF SEQ ID NOS: 175

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1

ggggctgatt ctggattcga c                                                21


<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2

tggagctggc gggagttgaa c                                                21
```

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
gggggcggaa aggattcgac g 21

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
tggaggcggc gggaatcgaa c 21

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
ggggatgtca tggttttgac a 21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tggagatggc gggaatcgaa c 21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ggggatgaca ggctatcgac a 21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagatggc gggacttgaa c 21

<210> SEQ ID NO 9
<211> LENGTH: 352
<212> TYPE: DNA
<213> ORGANISM: Acidobacterium capsulatum

<400> SEQUENCE: 9

-continued

```
gggggcggaa aggattcgac ggggttgact gcggcaaaga ggcatgccgg ggggtgggca     60

cccgtaatcg ctcgcaaaac aatacttgcc aacaacaatc tggcactcgc agcttaatta    120

aataagttgc cgtcctctga ggcttcgcct gtgggccgag gcaggacgtc atacagcagg    180

ctggttcctt cggctgggtc tgggccgcgg ggatgagatc cacggactag cattctgcgt    240

atcttgtcgc ttctaagcgc agagtgcgaa acctaaagga atgcgactga gcatggagtc    300

tcttttctga caccaatttc ggacgcgggt tcgattcccg ccgcctccac ca            352
```

<210> SEQ ID NO 10
<211> LENGTH: 353
<212> TYPE: DNA
<213> ORGANISM: Coprothermobacter proteolyticus

<400> SEQUENCE: 10

```
gggggcggaa aggattcgac ggggagtcgg agccttgagc tgcaggcagg gttggctgcc     60

acaccttaaa aagggtagca aggcaaaaat aaatgccgaa ccagaatttg cactagctgc    120

ttaatgtaag cagccgctct ccaaactgag gctgcataag tttggaagag cgtcaaccca    180

tgcagcggct cttaagcagt ggcaccagct gtttaagggt gaaaagagtg gtgctgggca    240

gtgcggttgg gcttcctggg ctgcactgtc gagacttcac aggagggcta agcctgtaga    300

cgcgaaaggt ggcggctcgt cggacgcggg ttcgattccc gccgcctcca cca           353
```

<210> SEQ ID NO 11
<211> LENGTH: 399
<212> TYPE: DNA
<213> ORGANISM: Bacteroides thetaiotaomicron

<400> SEQUENCE: 11

```
ggggctgatt ctggattcga cagcgggcag aaatggtagg taagcatgca gtgggtcggt     60

aatttccact taaatctcag ttatcaaaac tttatctggc gaaactaatt acgctcttgc    120

tgcttaatcg aatcacagta gattagctta atccaggcac taggtgccag gacgagacat    180

cactcggaag ctgttgctcc gaagcattcc ggttcagtgg tgcagtaaca tcggggatag    240

tcagaagcgg cctcgcgttt ttgatgaaac tttagaggat aaggcaggaa ttgatggctt    300

tggttctgct cctgcacgaa aatttaggca aagataagca tgtagaaagc ttatgatttc    360

ctcgtttgga cgagggttca actcccgcca gctccacca                           399
```

<210> SEQ ID NO 12
<211> LENGTH: 352
<212> TYPE: DNA
<213> ORGANISM: Dictyoglomus thermophilum

<400> SEQUENCE: 12

```
ggggctgatt ctggattcga cagggagtac aaggatcaaa agctgcaagc cgaggtgccg     60

ttacctcgta aaacaacggc aaaaaagaag tgccaacaca aatttagcat tagctgctta    120

atttagcagc tacgctcttc taacccgggc tggcagggtt agaagggtgt cataatgagc    180

cagctgcccc ttccgactcc cctaaggaag ggaaagatgt aggggatagg tgcttacaga    240

atcctgcggg agggagtctg taagtgccga aaagttaaaa ctcccgctaa gcttgtagag    300

gcttttgatt cttgctctct ggacgcgggt tcaactcccg ccagctccac ca            352
```

<210> SEQ ID NO 13
<211> LENGTH: 313
<212> TYPE: DNA
<213> ORGANISM: Artificial
<220> FEATURE:

<223> OTHER INFORMATION: sequence isolated from rumenal fluid

<400> SEQUENCE: 13

| acgcccttgt | ctcagacgag | ggcactcgtt | aaaaagtctg | aaaagaataa | ctgcagaacc | 60 |
| tgtagctatg | gctgcttaat | ttaagggcaa | cccttggatc | cgcctccatc | ccgaaggggt | 120 |
| ggcatccgag | tcgcaaatcg | ggataggatg | gatcttggca | acgaggagta | catccgaaat | 180 |
| ttgtcgctgc | tggctgaagc | atcgccgttc | ctctttgggc | gtggcaaggc | aagattaaat | 240 |
| tcagaggata | agcgtgtagt | agcgagtgag | taggtgtttt | tggacgcggg | ttcaagtccc | 300 |
| gccatctcca | cca | | | | | 313 |

<210> SEQ ID NO 14
<211> LENGTH: 350
<212> TYPE: DNA
<213> ORGANISM: Artificial
<220> FEATURE:
<223> OTHER INFORMATION: sequence isolated from sludge

<400> SEQUENCE: 14

| ggggatgtca | tggttttgac | agggaaccag | gaggtgtgag | atgcatgccg | gagacgctgt | 60 |
| ccgctccgtt | atcaagcagc | aaacaaaact | aattgcaaac | aacaattact | ccttagcagc | 120 |
| gtaagcagct | aacgttcaac | ctctccggac | cgccgggagg | ggatttgggc | gtcgaaacag | 180 |
| cgcggacgct | ccggatagga | cgcccataat | atccggctaa | gaccatgggt | ctggctctcg | 240 |
| cgggtctgat | tgtcttccac | cgcgcgggcc | gcgatcaaag | acaactaagc | atgtaggttc | 300 |
| ttgcatggcc | tgttctttgg | acgcgggttc | gattcccgcc | atctccacca | | 350 |

<210> SEQ ID NO 15
<211> LENGTH: 359
<212> TYPE: DNA
<213> ORGANISM: Fibrobacter succinogenes

<400> SEQUENCE: 15

| ggggctgatt | ctggattcga | cagggttacc | gaagtgttag | ttgcaagtcg | aggtctcaga | 60 |
| cgagggctac | tcgttaaaaa | gtctgaaaaa | aaataagtgc | tgacgaaaac | tacgcactcg | 120 |
| ctgcctaatt | aacggcaacg | ccgggcctca | ttccgctccc | atcggggtgt | acgtccggac | 180 |
| gcaatatggg | atagggaagt | gtcatgcctg | ggggcatctc | ccgagatttt | ctaggctggt | 240 |
| caaactccgc | gccgaccttc | ttgggcgtgg | ataagacgag | atcttaaatt | cgaagggaac | 300 |
| acttgtagga | acgtacatgg | acgtgatttt | ggacaggggt | tcaactcccg | ccagctcca | 359 |

<210> SEQ ID NO 16
<211> LENGTH: 350
<212> TYPE: DNA
<213> ORGANISM: Fusobacterium mortiferum

<400> SEQUENCE: 16

| ggggctgatt | ctggattcga | cggggttatg | aggttatagg | tagcatgcca | ggatgaccgc | 60 |
| tgtgagaggt | caacacatcg | tttagatgga | aacagaaatt | acgctttagc | tgcttaatta | 120 |
| gtcagctcac | ctctggtttc | tctcttctgt | aggagaatcc | aaccgaggtg | ttaccaatat | 180 |
| acagattacc | tttagtgatt | tctctaagct | caaagggaca | ttttagagaa | tagcttcagt | 240 |
| tagccctgtc | tgcgggagtg | attgttgcga | aataaaatag | tagactaagc | attgtagaag | 300 |
| cctatggcgc | tggtagtttc | ggacacgggt | tcaactcccg | ccagctccaa | | 350 |

<210> SEQ ID NO 17

<211> LENGTH: 377
<212> TYPE: DNA
<213> ORGANISM: Corynebacterium xerosis

<400> SEQUENCE: 17

```
ggggctgatt ctggattcga cttcgtacat tgagccaggg gaagcgtgcc ggtgaaggct     60

ggagaccacc gcaagcgtcg cagcaaccaa ttaagcgccg agaactctca gcgcgactac    120

gccctcgctg cctaagcagc gaccgcgtgt ctgtcagacc gggtaggcct ctgatccgga    180

ccctggcatc gtttagtggg gctcgctcgc cgacttggtc gcaagggtcg gcggggacac    240

tcacttgcga ctgggcccgt catccggtca tgttcgactg aaccggaggg ccgagcagag    300

accacgcgcg aactgcgcac ggagaagccc tggcgaggtg acggaggacc cgggttcaac    360

tcccgccagc tccacca                                                   377
```

<210> SEQ ID NO 18
<211> LENGTH: 372
<212> TYPE: DNA
<213> ORGANISM: Micrococcus luteus
<220> FEATURE:
<221> NAME/KEY: misc_feature
<222> LOCATION: (1)..(372)
<223> OTHER INFORMATION: n is an unknown base

<400> SEQUENCE: 18

```
ggggctattc tggattcgac ggtgtgtgtc gcgtcgggag aagcgggccg aggatgcaga     60

gtcatctcgt caaacgctct ctgcaaacca ataagtgccg aatccaagcg cactgacttc    120

gctctcgctg cctgatcagt gatcgagtcc gtcaccccga ggtcgctgtc gcctcggatc    180

gtggcgtcag ctagatagcc actgggcgtc accctcgccg gggtcgtga cgccgacatc     240

aatccggctg ggtccgggtt ggccgcccgt ctgcgggacg gccaggaccg agcaacaccc    300

acagcagact gcgcccggag aagacctggc aacacctcat cggacgcggg ttcaactccc    360

gcantcccac ca                                                        372
```

<210> SEQ ID NO 19
<211> LENGTH: 372
<212> TYPE: DNA
<213> ORGANISM: Mycobacterium smegmatis

<400> SEQUENCE: 19

```
tcatctcggc ttgttcgcgt gaccgggaga tccgagtaga gacatagcga actgcgcacg     60

gagaggggct gattcctgga ttcgacttcg agcatcgaat ccagggaagc gtgccggtgc    120

aggcaagaga ccaccgtaag cgtcgttgca accaattaag cgccgattcc aatcagcgcg    180

actacgccct cgctgcctaa gcgacggctg gtctgtcaga ccgggagtgc cctcggcccg    240

gatcctggca tcagctagag ggacccaccc acgggttcgg tcgcgggacc tgtggggaca    300

tcaaacagcg actgggatcg agcctcgagg acatgccgta ggacccgggt tcaactcccg    360

ccagctccac ca                                                        372
```

<210> SEQ ID NO 20
<211> LENGTH: 355
<212> TYPE: DNA
<213> ORGANISM: Bacillus badius

<400> SEQUENCE: 20

```
gggggtgatt ctggattcga cagggatagt tcgagcttgg gctgcgagcc ggagggccgt     60

cttcgtacca acgcaaacgc ctaaatataa ctggcaaaaa agatttagct ttagctgcct    120
```

-continued

```
aatataggtt cagctgctcc tcccgctatc gtccatgtag tcgggtaagg ggtccaaact    180

tagtggacta cgccggagtt ctccgcctgg ggacaaagga agagatcaat caggctagct    240

gcccggacgc ccgtcgatag gcaaaaggaa cagtgaaccc caaatatatc gactacgctc    300

gtagacgttc aagtggcgtt atctttggac gtgggttcaa ctcccgccag ctcca         355


<210> SEQ ID NO 21
<211> LENGTH: 357
<212> TYPE: DNA
<213> ORGANISM: Bacillus brevis

<400> SEQUENCE: 21

gggggcggaa aggattcgac ggggatggta gagcatgaga agcgagccgg ggggttgcgg     60

acctcgtcac caacgcaaac gccattaact ggcaacaaac aactttctct cgctgcttaa    120

taaccagtga ggctctccca ctgcatcggc ccgtgtgccg tggatagggc tcaactttaa    180

cgggctacgc cggaggcttc cgcctggagc caaaggaaga agaccaatca ggctaggtgc    240

caggtcagcg cgtcactccg cgaatctgtc accgaaactc taaacgagtg actgcgctcg    300

gagatgctca tgtatcgctg ttttcggacg gggttcgat tcccgccgcc tcaccca       357


<210> SEQ ID NO 22
<211> LENGTH: 354
<212> TYPE: DNA
<213> ORGANISM: Bacillus thermoleovorans

<400> SEQUENCE: 22

gggggcggaa aggattcgac gggggtaggt cgagcttaag cggcgagccg agggggacgt     60

cctcgtaaaa acgtcaccta aagataactg gcaaacaaaa ctacgcttta gctgcctaat    120

tgctgcagct agctcctccc gccatcgccc gcgtggcgtt cgaggggctc atatggagcg    180

ggctacgccc aaatccgccg cctgaggatg agggaagaga cgaatcaggc tagccgccgg    240

gaggcctgtc ggtaggcgga acggacggcg aagcgaaata taccgactac gctcgtagat    300

gcttaagtgg cgatgcctct ggacgtgggt tcgattcccg ccgcctcccc acca          354


<210> SEQ ID NO 23
<211> LENGTH: 384
<212> TYPE: DNA
<213> ORGANISM: Clostridium innocuum

<400> SEQUENCE: 23

gggggcggaa aggattcgac ggggatatgt ctggtacaga ctgcagtcga gtggttacgt     60

aataaccaat taaatttaaa cggaaaaact aaattagcta acctctttgg tggaaaccag    120

agaatggctt tcgctgctta ataaccgata taggttcgca gccgcctctg catgcttctt    180

ccttgaccat gtggatgtgc gcgtaagacg caagggataa ggaatctggt ttgcctgaga    240

tcagattcac gaaaattctt caggcacatt catcagcgga tgttcatgac ctgctgatgt    300

cttaatcttc atggactaaa ctgtagaggt ctgtacgtgg ggctgtttct ggacaggagt    360

tcgattcccg ccgcctcacc acca                                           384


<210> SEQ ID NO 24
<211> LENGTH: 349
<212> TYPE: DNA
<213> ORGANISM: Clostridium lentocellum

<400> SEQUENCE: 24

gggggcggaa aggattcgac gggggtcaca tctactgggg cagccatccg tagaacgccg     60
```

-continued gagtctacgt taaaagctgg cacttaaagt aaacgctgaa gataatttag caatcgctgc 120
ctaattaagg cgcagtcctc ctaggtcttc cgcagcctag atcagggctt cgactcgcgg 180
atccttcacc tggcaaagct ttgagccaac gtgaacacta tgaagctact aaaatctaga 240
gcctgtcttt gggcgctaga tggagggaat gtcaaaacaa agaatatgat ggtagagacc 300
acgctatatg ggctttcgga caggggttcg attcccgccg ccttcacca 349

<210> SEQ ID NO 25
<211> LENGTH: 358
<212> TYPE: DNA
<213> ORGANISM: Clostridium perfringens

<400> SEQUENCE: 25
ggggctgatt ctggattcga cgggggtaag atgggtttga taagcgagtc gagggaagca 60
tggtgcctcg ataataaagt atgcattaaa gataaacgca gaagataatt ttgcattagc 120
agcttaattt agcgctgctc atccttcctc aattgcccac ggttgagagt aagggtgtca 180
tttaaaagtg gggaaccgag cctagcaaag ctttgagcta ggaacggaat ttatgaagct 240
taccaaagag gaagtttgtc tgtggacgtt ctctgaggga attttaaaac acaagactac 300
actcgtagaa agtcttactg gtctgctttc ggacacgggt tcaactcccg ccactcca 358

<210> SEQ ID NO 26
<211> LENGTH: 362
<212> TYPE: DNA
<213> ORGANISM: Clostridium stercorarium

<400> SEQUENCE: 26
gggggcggaa aggattcgac ggggttattg aagcaagagt agcgggtaga ggattctcgt 60
tggcctcttt aaaaaacgag agctaaaaat aaacgcaaac aacgataact acgctttagc 120
tgctgcgtaa gtaacacgca gcccgtcggc cccggggttc ctgcgcctcg ggataccggc 180
gtcatcaagg cagggaacca gccggatcag gcttcaggtc cggtgggatt taatgaagct 240
accgacttat aaagcctgtc tctgggcgtt ataagaaggg aatgtcaaaa cagagactgc 300
acccggagaa gctcttgtgg atatggttcc ggacacgagt tcgattcccg ccgcctccac 360
ca 362

<210> SEQ ID NO 27
<211> LENGTH: 369
<212> TYPE: DNA
<213> ORGANISM: Enterococcus faecium
<220> FEATURE:
<221> NAME/KEY: misc_feature
<222> LOCATION: (1)..(369)
<223> OTHER INFORMATION: n is an unknown base

<400> SEQUENCE: 27
ggggctgatt atggattcga caggatngtt gagcttgaat tgcgtttcgt aggttacggc 60
tacgttaaaa cgttacagtt aaatataact gctaaaaacg aaaacaattc tttcgcttta 120
gctgcctaaa aaccagctag cgaagatcct cccggcatcg cccatgtgct cgggtcaggg 180
tcctaatcga agtgggatac gctaaatttt tccgtctgta aaatttagag gagcttacca 240
gactagcaat acaagaatgc ctgtcactcg gcacgctgta aagcgaacct ttaaatgagt 300
gtctatgaac gtagagattt aagtgggaat atgttttgga cgcgggttca actcccgcca 360
gctccacca 369

<210> SEQ ID NO 28

-continued

<211> LENGTH: 353
<212> TYPE: DNA
<213> ORGANISM: Heliobacillus mobilis

<400> SEQUENCE: 28
ggggctgatt ctggattcga cggggaacgt gtttgcttgg gatgcgagcc gggttgccgc 60
caggaccgta aaaagggcgg aaggctttaa ttgccgaaga taactacgct ttagctgctt 120
aattgcagtc taacctcttc tcctctgtgc tctcggtgag gatgtaaggg gtcatttaag 180
agagctggct tcgaccaatt ctcggaggtc caagcgagat ttatcgagat agcctgacca 240
acgctctgtc tgccgtgcgg aaggaaggcg aaatctaaaa cgacagacta cgctcgtagt 300
gtcctttgtg ggcatttctt cggacgcggg ttcaactccc gccagctcca cca 353

<210> SEQ ID NO 29
<211> LENGTH: 353
<212> TYPE: DNA
<213> ORGANISM: Heliospirillum gestii

<400> SEQUENCE: 29
ggggctgatt ctggattcga cggggaacgt gtttgcttag gacgcgagcc gggttgccgc 60
caggaccgta aaaagggcgg aaggctttaa ttgccgaaga taactacgct ttagctgctt 120
aattgcagtc taacctcttc tcctctgtgc tctcggtgag gatgtaaggg gtcatttaag 180
agagctggct cgaaccaatt ctcggaggtt cgggtaagac ttatcgagat agcctgacca 240
acgctctgtc tgccgtgcgg aaggatggcg aaatctaaaa cgacagaata cgctcgtagt 300
gtcctttgtg ggcatttctt cggacgcggg ttcaactccc gccagctcca cca 353

<210> SEQ ID NO 30
<211> LENGTH: 368
<212> TYPE: DNA
<213> ORGANISM: Lactobacillus acidophilus

<400> SEQUENCE: 30
ggggctgatt ctggattcga caggcgtaga cccgcattga ctgcggttcg taggttacgt 60
ctacgtaaaa acgttacagt taaatataac tgcaaataac aaaaattctt acgcattagc 120
tgcttaattt agcgcatgcg ttgctctttg tcggtttact cgtggctgac actgagtatc 180
aacttagcga gttacgttta actacctcac ctgaatagtt gaaaagagtc ttagcaggtt 240
agctagtcca tactagccct gttatatggc gttttggact agtgaagttc aagtaatata 300
actatgatcg tagaggtcag tgacgagatg cgtttggaca gcgggttcaa ctcccgccag 360
ctccacca 368

<210> SEQ ID NO 31
<211> LENGTH: 360
<212> TYPE: DNA
<213> ORGANISM: Staphylococcus epidermidis

<400> SEQUENCE: 31
ggggctgatt ctgcattcga caggggtccc cgagcttatt aagcgtgtgg agggttggct 60
ccgtcatcaa cacatttcgg ttaaatataa ctgacaaatc aaacaataat ttcgcagtag 120
ctgcgtaata gccactgcat cgcctaacag catctcctac gtgctgttaa cgcgattcaa 180
ccctagtagg atatgctaaa cactgccgct tgaagtctgt ttagatgaaa tataatcaag 240
ctagtatcat gttggttgtt tattgcttag catgatgcga aaattatcaa taaactacac 300
acgtagaaag atttgtatca ggacctctgg acgcgggttc aactcccgcc agctccacca 360

<210> SEQ ID NO 32
<211> LENGTH: 368
<212> TYPE: DNA
<213> ORGANISM: Streptococcus faecium

<400> SEQUENCE: 32
ggggctgatt ctggattcga caggcacagt ttgagcttga attgcgtttc gtaggttacg 60
tctacgttaa aacgttacag ttaaatataa ctgctaaaaa cgaaaacaac tcttacgctt 120
tagctgccta aaaacagtta gcgtagatcc tctcggcatc gcccatgtgc tcgagtaagg 180
gtctcaaatt tagtgggata cgtgacaact ttccgtctgt aagttgttaa agagatcatc 240
agactagcga tacagaatgc ctgtcactcg gcaagctgta aagcgaaacc acaaatgagt 300
tgactatgaa cgtagatttt taagtggcga tgtgtttgga cgcgggttca actcccgccg 360
ttccacca 368

<210> SEQ ID NO 33
<211> LENGTH: 328
<212> TYPE: DNA
<213> ORGANISM: Thermoanaerobacterium saccharolyticum

<400> SEQUENCE: 33
ggggtagtag aggtaaaagt agcgagccga ggttccatct gctcgtaaaa cggtggactt 60
aaatataaac gcaaacgata atttagctta cgctgcttaa ttacaagcag ccgttcaacc 120
tttgattccc acatcaaagg attgggcgtc gatttagtgg ggaactgatt tatcaaagct 180
ttgagataaa tcggatttta tgaagctacc aaagcagtta tcctgtcact gggagaactg 240
cagagggaat gtcaaaacag tgactgcgct cggagaagct tttactgtga caccttcgga 300
ccggggttca actcccgcca gcccacca 328

<210> SEQ ID NO 34
<211> LENGTH: 379
<212> TYPE: DNA
<213> ORGANISM: Mycoplasma fermentans

<400> SEQUENCE: 34
ggggctgatt ctggattcga catgcattgg gtgatactaa tatcagtagt ttggcagact 60
ataatgcatc taggctttat aatcgcagaa gataaaaaag cagaagaagt taatatttct 120
tcacttatga ttgcacaaaa aatgcaatca caatcaaacc ttgctttcgc ttagttaaaa 180
gtgacaagtg gttttaaagt tgacattttc ctatatattt taaaatcggc ttttaaggag 240
aacaggagtc tgaaagggtt ccaaaaatct atattgtttg catttcggta gtatagatta 300
attagaaatg ataaactgta aaaagtattg gtattgactt ggtgtgtgga ctcgggttca 360
actcccgcca gctccacca 379

<210> SEQ ID NO 35
<211> LENGTH: 373
<212> TYPE: DNA
<213> ORGANISM: Mycoplasma hyorhinis

<400> SEQUENCE: 35
ggggctgatt ctggattcga catacataaa aggatataaa ttgcagtggt cttgtaaacc 60
ataagacaat ttctttacta agcggaaaag aaaacaaaaa agaagattat tcattattaa 120
tgaatgcttc aactcaatca aatctagctt ttgcatttta aaaaactagt agaccaattt 180
gcttctcacg aattgtaatc tttatattag agaatagtta aaaatctgat cactttttaa 240
tgaatttata gatcacaggc ttttttaatc tttttgttat tttagataaa gagtcttctt 300
aaaaataact aaactgtagg aatttatatt taattatgcg tggacccggg ttcaactccc 360
gccagctcca cca 373

<210> SEQ ID NO 36
<211> LENGTH: 399
<212> TYPE: DNA
<213> ORGANISM: Mycoplasma pirum

<400> SEQUENCE: 36
ggggagtcat ggttttgaca tgaatgatgg acccatagag gcagtggggt atgcccctta 60
tagctcaagg tttaaattaa ccgacaaaac tgacgaaaac gttgccgttg atacaaattt 120
attaatcaac caacaagctc aatttaacta cgcatttgca tagtataaaa aaataaattg 180
tgctactcat tgtaattagg ttactaaatt actttgtttt atatagtcct gtaactagtt 240
ctagtgatgt ctataaacta gaatgagatt tatagactta tttgttggcg gttgtgccat 300
agcctaaatc aacaaagaca atttatttat ggtactaaac tgtagattct atgatgaaat 360
tatttgtgga aacgggttcg attcccgcca tctccacca 399

<210> SEQ ID NO 37
<211> LENGTH: 385
<212> TYPE: DNA
<213> ORGANISM: Mycoplasma salivarium

<400> SEQUENCE: 37
ggggctgatt ctggattcga caggcattcg attcattatg ttgcagtggt ttgcaaacca 60
taaggcacta ggctttttta aacgcaaaag accaaaaaac agaagatcaa gcagttgatc 120
tagcatttat gaataattca caaatgcaat caaatctagt tttcgcttag taaaattagt 180
caatttatta tggtgctcaa cataataaat ggtagtatga gcttaatatc atatgatttt 240
agttaatatg ataggatttg taactaaact atgttataga aatttgtaaa ttatatatat 300
gacataggaa atttaattta ctaaactgta gatgcataat gttgaagatg tgtggaccgg 360
ggttcaactc ccgccagctc cacca 385

<210> SEQ ID NO 38
<211> LENGTH: 362
<212> TYPE: DNA
<213> ORGANISM: Herpetosiphon aurantiacus

<400> SEQUENCE: 38
gggggcggaa aggattcgac ggggagggcc aatcgtaagt ggcaagccga gacgctgagc 60
ctcgttaaat cggcaacgcc attaactggc aaaaacactt tccgcgctcc tgtagcgctt 120
gctgcctaat taaggcaaca cgtctctact agcctcagcc cgatgggctt gtagcggcga 180
cacttagtcg ggtcgctccc ctagttatgt ctgtgggcta ggggctaaga ttaacaggct 240
ggtcgtggcc cgctttgtct atcgggtggt gcaccgataa gatttaatca atagactacg 300
cttgtagatg cttgcggttt aactttttgg acgcgggttc gattcccgcc gcctcaccac 360
ca 362

<210> SEQ ID NO 39
<211> LENGTH: 355
<212> TYPE: DNA
<213> ORGANISM: Thermomicrobium roseum

<400> SEQUENCE: 39

-continued

```
ggggctgatt ctggattcga cagggccgta ggtgcgagga ttgcaggtcg aggtcgccca     60

cgaactcgta aaaaggggca gccaagtaac tggcgagcgc gaactcgctc tggctgcgta    120

attcacgcag ccacgtctgc ccggaccctt ccctggtggg ttcggagcgg gcgccgcaag    180

accggggtgc ccctggccca agcgccggtg cgggccaggt caagcgtgat ccggctcggc    240

tgaccgggat cctgtcggtg ggagcctggc agcgacagta gaacaccgac taagcctgta    300

gcatatcctc ggctgaacgc tctggacgcg ggttcaactc ccgccagctc cacca         355


<210> SEQ ID NO 40
<211> LENGTH: 405
<212> TYPE: DNA
<213> ORGANISM: Chlorobium limicola

<400> SEQUENCE: 40

ggggctgatt ctggattcga caggatacgt gtgagatgtc gttgcactcc gagtttcagc     60

atggacggac tcgttaaaca agtctatgta ccattagatg cagacgatta ttcgtatgca    120

atggctgcct gattagcaca agttaactca gacgccatcg tcctgcggtg aatgcgctta    180

ctctgaagcc gccggatggc ataacccgcg cttgagccta cgggttcgcg caagtaagct    240

ccgtacattc atgcccgagg ggctgtgcgg gtaatttctc gggataaggg gacgaacgct    300

gctggcggtg taatcggccc acgaaaaccc aatcaccaga gatgagtgtg gtgactgcat    360

cgagcagtgt tttggacgcg ggttcaactc ccgccagctc cacca                    405


<210> SEQ ID NO 41
<211> LENGTH: 362
<212> TYPE: DNA
<213> ORGANISM: Pirellula staleyi

<400> SEQUENCE: 41

ggggctgatt ctggattcga ccggatagcc tgaagcgaat acggcgtgcc gtggttgatc     60

agatggccac gtaaaaagct gatcacaaac ttaactgccg agagcaatct cgcacttgct    120

gcctaactaa acggtagctt ccgactgagg gctttagccg gagaggccca aaagttggtc    180

accaaatccg gaccgcctcg tgccatgatc gaaacgcacg aggtcaaaaa agtttcgatc    240

tagtgcaggg tgtagccagc agctaggcga caaactgtgc aaaaatcaaa ttttctgcta    300

cgcacgtaga tgtgttcgtg aaaatgtctc gggacggggg ttcaactccc gccactccac    360

ca                                                                   362


<210> SEQ ID NO 42
<211> LENGTH: 346
<212> TYPE: DNA
<213> ORGANISM: Planctomyces limnophilus
<220> FEATURE:
<221> NAME/KEY: misc_feature
<222> LOCATION: (1)..(346)
<223> OTHER INFORMATION: n is an unknown base

<400> SEQUENCE: 42

ggggctgatt ctggattcga caacctctca agaggagcgt ggccactatg ggactcgatt     60

atgttgaatt cgtcatggat cttgaagaga ccttcgacat caaactggat gacaaacatt    120

tttcagcagt caaaacacca cgcgatttgg caatcattat tcgggatcaa ttagctgctg    180

aaggcagaat ctgggatgaa tcgaatgctt ttcgcaaaat ctcgaatttg aattggacga    240

tgttgcccga gttccggatg tggactcaaa tcaaaagctc tctaccagtt tcttttcacc    300

gactgcgtcc cagcacccgt ctcgttcaac tcccgccant ccacca                   346
```

<210> SEQ ID NO 43
<211> LENGTH: 362
<212> TYPE: DNA
<213> ORGANISM: Planctomyces maris

<400> SEQUENCE: 43
ggggctgatt ctggattcga ctggttcacc gtatgttaag gtggcggtgc cgtggttgat 60
cagttggcca cgtaaaaagc tgatcacaat ctaattgcaa acaagcaatt ttcaatggct 120
gcttaataaa agcaaccccg gcttaggaat ctctgtctga ggagtccgac agctggtcac 180
aaaatcagac tggtatcaga tcaatgtccg ctccgtctga tacgagattc gtggtggact 240
ggtttccaac aggctctgtt tatcgtgccc gaagaaacga gactcaaacg ataaaatatg 300
caccgtagag gctttagctg agggttcaca ggacgcgggt tcaactcccg ccagctccac 360
ca 362

<210> SEQ ID NO 44
<211> LENGTH: 360
<212> TYPE: DNA
<213> ORGANISM: Alcaligenes eutrophus

<400> SEQUENCE: 44
ggggttgatt ctggattcga cgtgggttac aaagcagtgg agggcatacc gaggacccgt 60
cacctcgtta atcaatggga atgcaataac tgctaacgac gaacgttacg cactggccgc 120
ttaattgcgg ccgtcctcgc actggctcgc tgacgggcta gggtcgcaag accacgcgag 180
gtcatttacg tcagataagc tccggaaggg tcacgaagcc ggggacgaaa acctagtgac 240
tcgccgtcgt agagcgtgtt cgtccgcgat gcgccggtta aatcaaatga cagaactaag 300
tatgtagaac tctctgtgga gggcttacgg acgcgggttc aactcccgcc agctccacca 360

<210> SEQ ID NO 45
<211> LENGTH: 362
<212> TYPE: DNA
<213> ORGANISM: Alcaligenes faecalis

<400> SEQUENCE: 45
gggggcggaa aggattcgac gggggtcaag aagcagcaca gggcgtgtcg agcaccagta 60
cgctcgtaaa tccactggaa aactataaac gccaacgacg agcgtttcgc tctagccgct 120
taaggctggg ccactgcact aatttgtctt tgggttaggt agggcaacct acagcagtgt 180
tatttacaaa gaatcgaatc ggtctgcgcc acgaagtccg gttctaaaac ttagtggatc 240
gccaaggaaa ggcctgtcaa ttggcatagt ccaaggttaa aacttaaaat taattgacta 300
cacatgtaga actgtctgtg gacggcttgc ggacgggggt tcgattcccg ccgcctccac 360
ca 362

<210> SEQ ID NO 46
<211> LENGTH: 366
<212> TYPE: DNA
<213> ORGANISM: Chromobacterium violaceum

<400> SEQUENCE: 46
ggggctgatt ctggattcga cgggggttgc gaagcagatg agggcatacc gggatttcag 60
tcaccccgta aaacgctgaa tttatatagt cgcaaacgac gaaacttacg ctctggcagc 120
ctaacggccg gccagacact acaacggttc gcagatgggc cgggggcgtc aaaaccctgt 180
agtgtcactc tacatctgct agtgctgttc cgggttactt ggttcagtgc gaaataatag 240
gtaactcgcc aaagtccagc ctgtccgtcg gcgtggcaga ggttaaatcc aaatgacacg 300
actaagtatg tagaactcac tgtagaggac tttcggacgc gggttcaact cccgccagct 360
ccacca 366

<210> SEQ ID NO 47
<211> LENGTH: 378
<212> TYPE: DNA
<213> ORGANISM: Hydrogenophaga palleroni

<400> SEQUENCE: 47
ggggctgatt ctggattcga cgtgggttcg gacgcgcagc agggcatgtc gaggttctgt 60
cacctcgtaa atcagcagaa aaaaaccaac tgcaaacgac gaacgtttcg cactcgccgc 120
ttaaacaccg gtgagccttg caacagcagg ccgatgggct gggcaagggg gtcgcaagac 180
ctcccggctg caaggtaatt tacatcggct ggttctgcgt cgggcacctt ggcgcaggat 240
gagattcaag gatgctggct tcccgtttag cgtgccactg cgcgactcgg gcggcgagac 300
ccaaatcaga cggctacaca tgtagaactg ctcgaaaaag gcttgcggac gggggttcaa 360
ctcccgccag ctccacca 378

<210> SEQ ID NO 48
<211> LENGTH: 365
<212> TYPE: DNA
<213> ORGANISM: Methylobacillus glycogenes

<400> SEQUENCE: 48
gggggcggaa aggattcgac gggggttgca aagcagcgca gggcataccg aggcctagtc 60
acctcgtaaa taaactagaa caagtatagt cgcaaacgac gaaacttacg ctctagccgc 120
ttaatcccgg ctggacgctg caccgaaggg cctctcggtc gggtggggta acccacagca 180
gcgtcattaa gagaggatcg tgcgatattg ggttacttaa tatcgtatta aatccaaggt 240
aactcgcctg ctgtttgctt gctcgttggt gagcatcagg ttaaatcaaa caacacagct 300
aagtatgtag aactgtctgt ggagggcttg cggacggggg ttcgattccc gccgcctcac 360
cacca 365

<210> SEQ ID NO 49
<211> LENGTH: 362
<212> TYPE: DNA
<213> ORGANISM: Nitrosomonas cryotolerans

<400> SEQUENCE: 49
ggggctgatt ctggattcga cgtgggttgc aaagcagcgc agggcatacc gaggaccaga 60
atacctcgta aatacatctg gaaaaaaata gtcgcaaacg acgaaaacta cgctttagcc 120
gcttaatacg gctagcctct gcaccgatgg gccttaacgt cgggtctggc aacagacagc 180
agagtcatta gcaaggatcg cgttctgtag ggtcacttta cagaacgtta aacaataggt 240
gactcgcctg ccatcagccc gccagctggc ggttgtcagg ttaaattaaa gagcatggct 300
aagtatgtag aactgtctgt agaggacttg cggacgcggg ttcaactccc gccagtccac 360
ca 362

<210> SEQ ID NO 50
<211> LENGTH: 378
<212> TYPE: DNA
<213> ORGANISM: Pseudomonas testosteroni

<400> SEQUENCE: 50

-continued

```
ggggctgatt ctggattcga cgtgggttcg ggaccggtgc ggtgcatgtc gagcttgagt     60

gacgctcgta aatctccatt caaaaaacta actgcaaacg acgaacgttt cgcactcgcc    120

gcttaatccg gtgagccttg caacagcacg ctagtgggct gggcaagggg gtagcaatac    180

ctcccggctg caagggaatt ttcattagct ggctggatac cgggcttctt ggtatttggc    240

gagattttag gaagctggct acccaagcag cgtgtgcctg cggggtttgg gtggcgagat    300

ttaaaacaga gcactaaaca tgtagatctg tccggcgaag gcttacggac gcgggttcaa    360

ctcccgccag ctccacca                                                  378
```

<210> SEQ ID NO 51
<211> LENGTH: 360
<212> TYPE: DNA
<213> ORGANISM: Ralstonia pickettii

<400> SEQUENCE: 51

```
gggggcggaa aggattcgac gggggttgcg aagcagcgga gggcataccg aggacccgtc     60

acctcgttaa tcaatgggaa tgcaataact gctaacgacg aacgttacgc actggcagcc    120

taagggccgc cgtcctcgca ctggctcgct gacgggctag ggtcgcaaga ccagcgaggt    180

catttacgtc agataagctt taggtgagtc acgggcctag agacgaaaac ttagtgaatc    240

gccgtcgtag agcgtgttcg tccgcgatgc ggcggttaaa tcaaatgaca gaactaagta    300

tgtagaactc tctgtggagg gcttgcggac gcgggttcga ttcccgccgc ctcaccacca    360
```

<210> SEQ ID NO 52
<211> LENGTH: 386
<212> TYPE: DNA
<213> ORGANISM: Variovorax paradoxus

<400> SEQUENCE: 52

```
ggggctgatt ctggattcga cgtgggttcg gagtcgcagc ggggcatgtc gagctgaatg     60

cgctcgtaaa acagattcaa acaaactaac tgcaaacgac gaacgtttcg cactcgctgc    120

ttaattgcca gtgagccttg caacagttgg ccgatgggct gggcaagggg gtctggagca    180

atcctgacct cccggctgca aggataacta catgggctgg ctccgatccg ggtaccttgg    240

gtcggggcga gaaaataggg tactggcgtc cggtttagcg tgtgactgcg cgactccgga    300

agcgagactc aaaacagatc actaaacatg tagaactgcg cgatgaaggc ttgcggacgg    360

gggttcaact cccgccagct ccacca                                         386
```

<210> SEQ ID NO 53
<211> LENGTH: 346
<212> TYPE: DNA
<213> ORGANISM: Bdellovibrio bacteriovirus

<400> SEQUENCE: 53

```
gggggcggaa aggattcgac gggggtgctg aagcataagg agcataccgg ggcggatgag     60

gacctcgtta aaaacgtcca ctttgtaatt ggcaacgatt acgcacttgc agcttaatta    120

agcagcacga tcaaccttgt ggtggttccg cacttggatt gatcgtcatt tagggacctc    180

ggcgtgttgg gttttctcca gcagacatgc ttaaatttac tgggggagag gtcttaggga    240

ttttgtctgt ggaagcccga ggaccaatct aaaacactga ctaagtatgt agcgccttat    300

cgtggatcat ttgcggacgg gggttcgatt cccgccgcct ccacca                   346
```

<210> SEQ ID NO 54
<211> LENGTH: 366
<212> TYPE: DNA

<213> ORGANISM: Myxococcus xanthus

<400> SEQUENCE: 54
gggggcggaa aggattcgac gggggcattg aagttcgaga cgcgtgccga gcttgtcagg 60
tagctcgtaa attcaacccg gcaaagacac aaaagccaac gacaacgttg agctcgcgct 120
ggctgcctaa aaacagccca tagtgcgcgg tccccccgcc ctcggcctgt ggggttggga 180
cagaccgtca taatgcaggc tggctgccga gggtgcctgg acccgaggtg gcgagatctt 240
cccaggaccg gctctgagta tcccgtccgt gggagcctca gggacgtagc aaatcgcgga 300
ctacgcacgt agggtcgaag agcggacggc tttcggacgc gggttcgatt cccgccgcct 360
ccacca 366

<210> SEQ ID NO 55
<211> LENGTH: 380
<212> TYPE: DNA
<213> ORGANISM: Sulfurospirillum deleyianum

<400> SEQUENCE: 55
ggggctgatt ctggattcga caggagtagt tttagcttat ggctgcatgt cgggagtgag 60
ggtcttccgt tacacaacct tcaaacaata actgctaaca acagtaacta tcgtcctgct 120
tacgcgctag ctgcgtaagt ttaacaaata atggactgct ctcccctttg atgctatctt 180
aggaggtctt ggagagtatc atagatttga tagctatatt acatgaacgc ctttacatgt 240
aatgaagtta aaggctcgtt ttgcgtagtt ttctgattgt tgtacgaagc aaaattaaac 300
actatcaaca atatctaagc atgtagacgt cataggtggc tatttttgga ctgcgggttc 360
aactcccgcc agctccacca 380

<210> SEQ ID NO 56
<211> LENGTH: 359
<212> TYPE: DNA
<213> ORGANISM: Chromatium vinosum

<400> SEQUENCE: 56
ggggctgatt ctggattcga cgtgggtcgc gaaacctaag gtgcatgccg aggtgcggtt 60
gacctcgtaa aaccctccgc aaacttatag ttgccaacga cgacaactac gctctcgctg 120
cttaatccca gcgggcctct gaccgtcact tgcctgtggg cggcggattc caggggtaac 180
ctcacacagg atcgtggtga cgggagtccg gacctgatcc actaaaacct aacggaatcg 240
ccgactgatc gccctgccct tcgggcggca gaaggctaaa aacaatagag tgggctaagc 300
atgtaggacc gagggcagag ggcttgcgga cgcgggttca actcccgcca gctccacca 359

<210> SEQ ID NO 57
<211> LENGTH: 395
<212> TYPE: DNA
<213> ORGANISM: Pseudomonas fluorescens

<400> SEQUENCE: 57
ggggctgatt ctggattcga cgccggttgc gaacctttag gtgcatgccg agttggtaac 60
agaactcgta aatccactgt tgcaactttc tatagttgcc aatgacgaaa cctacgggga 120
atacgctctc gctgcgtaag cagccttagc ccttccctcc tggtaccttc gggtccagca 180
atcatcaggg gatgtctgta aacccaaagt gattgtcata tagaacagaa tcgccgtgca 240
gtacgttgtg gacgaagcgg ctaaaactta cacaactcgc ccaaagcacc ctgcccgtcg 300
ggtcgctgag ggttaactta atagacacgg ctacgcatgt agtaccgaca gcagagtact 360

-continued

```
ggcggacgcg ggttcaactc ccgccagctc cacca                            395


<210> SEQ ID NO 58
<211> LENGTH: 362
<212> TYPE: DNA
<213> ORGANISM: Borrelia afzelii

<400> SEQUENCE: 58

ggggctgatt ctggattcga ctgaaaatgc taatattgta agttgcaagc agagggaatc     60

tcttaaaact tctaaaataa atgcaaaaaa taataacttt acaagttcaa accttgtaat    120

ggctgcttaa gttagcagag agttttgttg aatttggctt tgagattcac ttatactctt    180

ttagacatcg aagcttgctt aaaaatgttt tcaagttgat ttttagggac ttttatactt    240

gagagcaatt tggcggtttg ctagtatttc caaaccatat tgcttagtaa aatactagat    300

aagcttgtag aagcttatag tattgttttt aggacgcggg ttcaactccc gccagtccac    360

ca                                                                   362


<210> SEQ ID NO 59
<211> LENGTH: 363
<212> TYPE: DNA
<213> ORGANISM: Borrelia crocidurae

<400> SEQUENCE: 59

ggggctgatt ctggattcga ctaagaactt tagtagcata aatggcaagc agagtgaatc     60

tcttaaaact tctttaataa atgcaaaaaa taataacttt acaagttcag atcttgtaat    120

ggctgcttaa tttagcagag agttttgttg gattttgctt tgaggttcaa cttatactct    180

ttaagacatc aaagtatgcc taaaaatgtt tcaagttgat ttttagggac ctttaaactt    240

gagagtaatt tggtggtttg cttgttttcc aagccttatt gctttttcta aaaattagct    300

aagcttgtag atatttatga tattattttt aggacgcggg ttcaactccc gccagttcca    360

cca                                                                  363


<210> SEQ ID NO 60
<211> LENGTH: 365
<212> TYPE: DNA
<213> ORGANISM: Borrelia hermsii

<400> SEQUENCE: 60

ggggctgatt ctggattcga ctaaaaactt tagtagcata aattgcaagc agagggaatc     60

tcttaaaact tctttaataa atgcaagaaa taataacttt acaagttcaa atcttgtaat    120

ggctgcttaa attagcagag agttctgctg gattttgctt tgaggttcag cttatactct    180

tttaagacat caaagcttgc ttaaaaatat ttcaagttga tttttaggga cttttaaatt    240

tgagagtaat ttggcggttt gctagttttt ccaaacctta ttacttaaag aaaacactag    300

ctaagcttgt agatatttat gatattattt ttaggacgcg ggttcaactc ccgccagctc    360

cacca                                                                365


<210> SEQ ID NO 61
<211> LENGTH: 363
<212> TYPE: DNA
<213> ORGANISM: Borrelia garinii

<400> SEQUENCE: 61

ggggctgatt ctggattcga ctgaaaatgc gaatattgta agttgcaggc agagggaatc     60

tcttaaaact tctaaaataa atgcaaaaaa taataacttt acaagctcaa accttgtaat    120
```

-continued

```
ggctgcttaa gttagcaggg agtttcgttg aatttggctt tgaggttcac ttatactctt    180

ttcgatatcg aagcttgctt aaaaatgttt tcaagttaat ttttagggac ttttgtactt    240

gagagcaatt tggcggtttg ctagtatttc caaaccatat tgcttaagta aaatgctaga    300

taagcttgta gaagcttata atattgtttt taggacgcgg gttcaactcc cgccagtcca    360

cca                                                                  363


<210> SEQ ID NO 62
<211> LENGTH: 357
<212> TYPE: DNA
<213> ORGANISM: Thermodesulfobacterium commune

<400> SEQUENCE: 62

gggggcggaa aggattcgac ggggataggt aggattaaac agcaggccgt ggtcgcaccc     60

aaccacgtta aatagggtgc aaaaacacaa ctgccaacga atacgcctac gctttggcag    120

cctaagcgtg ctgccacgca cctttagacc ttgcctgtgg gtctaaaggt gtgtgaccta    180

acaggctttg ggaggcttaa tcggtggggt taagcctccc gagattacat cccacctggt    240

agggttgctt ggtgcctgtg acaagcaccc tacgagattt tcccacaggc taagcctgta    300

gcggtttaat ctgaactatc tccggacgcg ggttcgattc ccgccgcctc cccacca       357


<210> SEQ ID NO 63
<211> LENGTH: 358
<212> TYPE: DNA
<213> ORGANISM: Thermotoga neapolitana
<220> FEATURE:
<221> NAME/KEY: misc_feature
<222> LOCATION: (1)..(358)
<223> OTHER INFORMATION: n is an unknown base

<400> SEQUENCE: 63

gggggcggaa aggattcgac ggggatggag tcccctggga agcgagccga ggtccccacc     60

tcctcgtaaa aaaggtggga acacgaataa gtgccaacga acctgttgct gttgccgcct    120

aatagatagg cggccgtcct ctccggagtt ggctgggctc cggaagaggg cgtgagggat    180

ccagcctacc gatctgggct ccgccttccg gcccggatcg ggaaggttca ggaaggctgt    240

gggaagcgac accctgcccg tggggggtcc ttcccgagac acgaaacacg ggctgcgctc    300

ggagaagccc aggggcctcc atcttcngac gcgggttcga ttcccgccac ctccacca      358


<210> SEQ ID NO 64
<211> LENGTH: 347
<212> TYPE: DNA
<213> ORGANISM: Deinococcus proteolyticus

<400> SEQUENCE: 64

gggggcggaa aggattcgac gggggaacgg aaagcgctgc tgcgtgccga ggagccgttg     60

gcctcgtaaa caaacggcaa agccattaac tggcgaaaat aactacgctc tcgctgctta    120

agtgagacag tgaccacgta gccccgcctt tggcgacgtg tgaactgaga caaaagaagg    180

ctagcttagg tgaggttcca tagccaaaag tgaaaccaaa tggaaataag gcggacggca    240

gcctgtttgc tggcagccca ggcccgacaa tttaagagca gactacgcac gtagatgcac    300

gctggatgga cctttggacg cgggttcgat tcccgccagc tccacca                  347


<210> SEQ ID NO 65
<211> LENGTH: 352
<212> TYPE: DNA
<213> ORGANISM: Prosthecobacter fusiformis
```

<400> SEQUENCE: 65
ggggctgatt ctggattcga cggggagtac aaggatcaaa agctgcaagc cgaggtgccg 60
ttacctcgta aaacaacggc aaaaaagaag tgccaacaca aatttagcat tagctgctta 120
atttagcagc tacgctcttc taacccgggc tggcagggtt agaagggtgt cataatgagc 180
cagctgcccc ttccgactcc cctaaggaag ggaaagatgt aggggatagg tgcttacaga 240
atcctgcggg agggagtctg taagtgccga aaagttaaaa ctcccgctaa gcttgtagag 300
gcttttgatt cttgctctct ggacgcgggt tcaactcccg ccagctccac ca 352

<210> SEQ ID NO 66
<211> LENGTH: 329
<212> TYPE: DNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 66
gggnnnnatt tggaattcgc cgaatgctag aagtggaggc tgcatgccgc ggatgattcg 60
ttggccgctt taccaattcg gatcaaacaa ctaaatgcgg actctaacga gcttgccctc 120
gccgcttaat tgacggtgac gttcctccag tgaagtctgt gaattggagg agcgactact 180
tacaggctgg ccaaaagagc gggcgaccgg ccccaaggcg agatctacag gccgctggat 240
ggacggcatc ctggcagtag gaggctggac atcgagatca aatnattgcc tgagcatgga 300
gacgctttca taaaggngtt cggacaggg 329

<210> SEQ ID NO 67
<211> LENGTH: 318
<212> TYPE: RNA
<213> ORGANISM: Thermoanaerobacterium saccharolyticum

<400> SEQUENCE: 67
cgggggtagu agagguaaaa guagcgagcc gagguuccau cugcucguaa aacgguggac 60
uuaaauauaa acgcaaacga uaauuuagcu uacgcugcuu aauuacaagc agccguucaa 120
ccuuugauuc ccacaucaaa ggauugggcg ucgauuuagu ggggaacuga uuuaucaaag 180
cuuugagaua aaucggauuu uaugaagcua ccaaagcagu uauccuguca cugggagaac 240
ugcagaggga augucaaaac agugacugcg cucggagaag cuuuuacugu gacaccuucg 300 gaccggggguu caacuccc 318

<210> SEQ ID NO 68
<211> LENGTH: 187
<212> TYPE: RNA
<213> ORGANISM: Clostridium acetobutylicum

<400> SEQUENCE: 68
aaucuggcgu cgagagcggg gaaacgagcc uuacaaagcu uugaguaagg aacggaauuu 60
augaagcuac ugaagugaaa agcuuguuug uaggcguuuc auggagggaa uguuaaaaua 120
caaacugcac ucggagaugc uuaaaugaaa ccauuuucgg acaggggguuc gauuccccuc 180 gccucca 187

<210> SEQ ID NO 69
<211> LENGTH: 335
<212> TYPE: RNA
<213> ORGANISM: Clostridium stercorarium

<400> SEQUENCE: 69 cggggguuauu gaagcaagag uagcggguag aggauucucg uuggccucuu uaaaaaacga 60
gagcuaaaaa uaaacgcaaa caacgauaac uacgcuuuag cugcugcgua aguaacacgc 120
agcccgucgg ccccggggguu ccugcgccuc gggauaccgg cgucaucaag gcagggaacc 180
agccggauca ggcuucaggu ccggugggau uuaaugaagc uaccgacuua uaaagccugu 240
cucugggcgu uauaagaagg gaaugucaaa acagagacac caaugcaccc ggagaagcuc 300
uuguggauau gguuccggac acgaguucga uuccc 335

<210> SEQ ID NO 70
<211> LENGTH: 336
<212> TYPE: RNA
<213> ORGANISM: Clostridium perfringens

<400> SEQUENCE: 70
cggggguaag auggguuuga uaagcgaguc gagggaagca uggugccucg auaauaaagu 60
augcauuaaa gauaaacgca gaagauaauu uugcauuagc agcuuaauuu agcgcugcuc 120
auccuuccuc aauugcccac gguugagagu aaggguguca uuuaaaagug gggaaccgag 180
ccuagcaaag cuuugagcua ggaacggaau uuaugaagcu uagaggaagu uugucugugg 240
acguucucug agggaauuuu aaaacacaag acacuaaaau cuaguacacu cguagaaagu 300
cuuacugguc ugcuuucgga cacggguuca acuccc 336

<210> SEQ ID NO 71
<211> LENGTH: 305
<212> TYPE: RNA
<213> ORGANISM: Clostridium lentocellum

<400> SEQUENCE: 71
cgggggucac aucuacuggg gcagccaucc guagaacgcc ggagucuacg uuaaaagcug 60
gcacuuaaag uaaacgcuga agauaauuua gcaaucgcug ccuaauuaag gcgcaguccu 120
ccuaggucuu ccgcagccua gaucagggcu ucgacucgcg gauccuucac cuggcaaagc 180
uuugagccaa cgugaacacu augaagcuag ccugucuuug ggcgcuagau ggagggaaug 240
ucaaaacaaa gaauaugaug guagagacca cgcuauaugg gcuuucggac aggggguucga 300 uuccc 305

<210> SEQ ID NO 72
<211> LENGTH: 319
<212> TYPE: RNA
<213> ORGANISM: Heliobacillus mobilis

<400> SEQUENCE: 72
cggggaacgu guuugcuugg gaugcgagcc ggguugccgc caggaccgua aaaagggcgg 60
aaggcuuuaa uugccgaaga uaacuacgcu uuagcugcuu uauugcaguc uaaccucuuc 120
uccucugugc ucucggugag gauguaaggg gucauuuaag agagcuggcu ucgaccaauu 180
cucggagguc caagcgagau uuaucgagau agccugacca acgcucuguc ugccgugcgg 240
aaggaaggcg aaaucuaaaa cgacagauac gcucguagug uccuuugugg gcauuucuuc 300
ggacgcgggu ucaacuccc 319

<210> SEQ ID NO 73
<211> LENGTH: 321
<212> TYPE: RNA
<213> ORGANISM: Heliospirillum gestii

<400> SEQUENCE: 73
cggggaacgu guuugcuuag gacgcgagcc ggguugccgc caggaccgua aaaagggcgg 60
aaggcuuuaa uugccgaaga uaacuacgcu uuagcugcuu aauugcaguc uaaccucuuc 120
uccucugugc ucucggugag gauguaaggg gucauuuaag agagcuggcu cgaaccaauu 180
cucggagguu cggguaagac uuaucgagau cagccugacc aacgcucugu cugccgugcg 240
gaaggauggc gaaaucuaaa acgacagaau acgcucguag uguccuuugu gggcauuucu 300
ucggacgcgg guucaacucc c 321

<210> SEQ ID NO 74
<211> LENGTH: 325
<212> TYPE: RNA
<213> ORGANISM: Brevibacillus brevis

<400> SEQUENCE: 74
cggggauggu agagcaugag aagcgagccg gggguugcg gaccucguca ccaacgcaaa 60
cgccauuaac uggcaacaaa caacuuucuc ucgcugcuua auaaccagug aggcucuccc 120
acugcaucgg cccgugugcc guggauaggg cucaacuuua acgggcuacg ccggaggcuu 180
ccgccuggag ccaaaggaag aagaccaauc aggcuaggug ccaggucagc gcgucacucc 240
gcgaaucugu caccgaaacu cuaaacgagu gacugcgcuc ggagaugcuc auguaucgcu 300
guuuucggac ggggguucga uuccc 325

<210> SEQ ID NO 75
<211> LENGTH: 360
<212> TYPE: RNA
<213> ORGANISM: Bacillus subtilis

<400> SEQUENCE: 75
ggggacguua cggauucgac agggauggau cgagcuugag cugcgagccg agaggcgauc 60
ucguaaacac gcacuuaaau auaacuggca aaacuaacag uuuuaaccaa aacguagcau 120
uagcugccua auaagcgcag cgagcucuuc cugacauugc cuaugugucu gugaagagca 180
cauccaagua ggcuacgcuu gcguucccgu cugagaacgu aagaagagau gaacagacua 240
gcucucggaa ggcccgcccg caggcaagaa gaugagugaa accauaaaua ugcaggcuac 300
gcucguagac gcuuaaguaa ucgauguuuc uggacguggg uucgacuccc accgucucca 360

<210> SEQ ID NO 76
<211> LENGTH: 325
<212> TYPE: RNA
<213> ORGANISM: Bacillus badius

<400> SEQUENCE: 76
cagggauagu ucgagcuugg gcugcgagcc ggagggccgu cuucguacca acgcaaacgc 60
cuaaauauaa cuggcaaaaa agauuuagcu uuagcugccu aauauagguu cagcugcucc 120
ucccgcuauc guccauguag ucggguaagg gguccaaacu uaguggacua cgccggaguu 180
cuccgccugg ggacaaagga agagaucaau caggcuagcu gcccggacgc ccgucgauag 240
gcaaaaggaa cagugaaccc caaauauauc gacuacgcuc guagacguuc aaguggcguu 300
aucuuuggac gugggguucaa cuccc 325

<210> SEQ ID NO 77
<211> LENGTH: 341
<212> TYPE: RNA
<213> ORGANISM: Bacillus megaterium

<400> SEQUENCE: 77
ggggacguua cggauucgac aggguaguuc gagcuuaggu ugcgagucga ggagauggcc 60
ucguuaaaac aucaacgcca auaauaacug gcaaaucuaa caauaacuuc gcuuuagcug 120
cauaauagua gcuuagcguu ccucccucca ucgcccaugu gguaggguaa gggacucacu 180
uuaagugggc uacgccggag uucgccgucu gaggacgaag gaagagaaua aucagacuag 240
cgacugggac gccuguuggu aggcagaaca gcucgcgaau gaucaauaug ccaacagccg 300
uacacucgua gacgcuuaag uggccauauu ucuggacgug g 341

<210> SEQ ID NO 78
<211> LENGTH: 315
<212> TYPE: RNA
<213> ORGANISM: Bacillus thermoleovorans

<400> SEQUENCE: 78
cggggguagg ucgagcuuaa gcggcgagcc gaggggggacg uccucguaaa aacgucaccu 60
aaagauaacu ggcaaacaaa acuacgcuuu agcugccuaa uugcugcagc uagcuccucc 120
cgccaucgcc cgcguggcgu ucgaggggcu cauauggagc gggcuacgcc caaauccgcc 180
gccugaggau gagggaagag acgaaucagg cuccgggagg ccugucggua ggcggaacgg 240
acggcgaagc gaaauauacc gacuacgcuc guagaugcuu aaguggcgau gccucuggac 300 gugggguucga uuccc 315

<210> SEQ ID NO 79
<211> LENGTH: 335
<212> TYPE: RNA
<213> ORGANISM: Enterococcus faecium

<400> SEQUENCE: 79
caggcacagu uugagcuuga auugcguuuc guagguuacg ucuacguuaa aacguuacag 60
uuaaauauaa cugcuaaaaa cgaaaacaac ucuuacgcuu uagcugccua aaaacaguua 120
gcguagaucc ucucggcauc gcccaugugc ucgaguaagg gucucaaauu uagugggaua 180
cgugacaacu uuccgucugu aaguuguuaa agagaucauc agacuagcga uacagaaugc 240
cugucacucg gcaagcugua aagcgaaacc acaaaugagu ugauaugaac guagauuuuu 300
aaguggcgau guguuuggac gcggguucaa cuccc 335

<210> SEQ ID NO 80
<211> LENGTH: 364
<212> TYPE: RNA
<213> ORGANISM: Enterococcus faecalis

<400> SEQUENCE: 80
gggggcguua cggauucgac aggcauaguu gagcuugaau ugcguuucgu agguuacggc 60
uacguuaaaa cguuacaguu aaauauaacu gcuaaaaacg aaaacaauuc uuucgcuuua 120
gcugccuaaa aaccagcuag cgaagauccu cccggcaucg cccaugugcu cgggucaggg 180
uccuaaucga agugggauac gcuaaauuuu uccgucugua aaauuuagag gagcuuacca 240
gacucagcaa uacagaaugc cugucacucg gcacgcugua aagcgaaccu uuaaaugagu 300
guuaugaacg uagagauuua aguggcaaua uguuuggacg cggguucgac ucccgccguc 360
ucca 364

<210> SEQ ID NO 81
<211> LENGTH: 346
<212> TYPE: RNA

<213> ORGANISM: Streptococcus pyogenes

<400> SEQUENCE: 81

```
ggggguugua cggauucgac aggcauuaug aggcauguuu ugcgucccau cggcagaugu     60

aaauugccag uuaaauauaa cugcaaaaaa uacaaacucu uacgcuuuag cugccuaaaa    120

accagcuagc gugacuucua caagauugcu uguguccugu uagaagucuc aaaauagcaa    180

gcuacgguua cgaaauuguc uaguuucgug acaagagauu gauagacucc gcaaacuaau    240

ggcuugaguu augugucuuu aguuuguuaa augaagacau aaccuaugga cguagacaaa    300

uauguuggca gguguuugga cguggguucg acucccacca gcucca                   346
```

<210> SEQ ID NO 82
<211> LENGTH: 344
<212> TYPE: RNA
<213> ORGANISM: Streptococcus pneumoniae

<400> SEQUENCE: 82

```
ggggucguua cggauucgac aggcauuaug aggcauauuu ugcgacucgu guggcgacgu     60

aaacgcucag uuaaauauaa cugcaaaaaa uaacacuucu uacgcucuag cugccuaaaa    120

accagcaggc gugacccgau uuggauugcu cguguucaau gacaggucuu auuauuagcg    180

agauacgauu aagccuuguc uagcgguuug auaagagauu gauagacucg caguuucuag    240

acuugaguua ugugucgagg ggcuguuaaa auaauacaua acuaugguug uagacaaaua    300

uguuggcagg uguuuggacg uggguucgac ucccaccggc ucca                     344
```

<210> SEQ ID NO 83
<211> LENGTH: 364
<212> TYPE: RNA
<213> ORGANISM: Streptococcus gordonii

<400> SEQUENCE: 83

```
ggggucguua cggauucgac aggcauuaug aggcauauuu ugcgacucau cuagcggaug     60

uaaaacgcca guuaaauaua acugcaaaaa auaauacuuc uuacgcuuua gcugccuaaa    120

aaccagcggg cgugacccga uucggauugc uugugucuga ugacaggucu uauuauuagc    180

aagcuacggu agaaucuugu cuagugauuu uacaagagau ugauagacua cguuagaacu    240

gagucagccg cuugauuugg gcuugaguua ugugucaaaa ucaaguuaaa acaauacaua    300

gcuaugguug uagacaaaua uguuggcaga uguuuggacg uggguucgac ucccaccggc    360

ucca                                                                 364
```

<210> SEQ ID NO 84
<211> LENGTH: 329
<212> TYPE: RNA
<213> ORGANISM: Streptococcus mutans

<400> SEQUENCE: 84

```
ggggucguua cggauucgac aggcauuaug agaccuauuu ugcgacucau cuagcggaug     60

uaaaacgcca guuaaauaua acugcaaaaa auacaaauuc uuacgcagua gcugccuaaa    120

aaccagccug ugugaucaau aacaaauugc uuguguuugu ugauuggucu uauuguuaac    180

aagcugcugu ucuaaaagag uucuacugac uccgcaucgu uagaguuuga guuauguauu    240

guaacggugu uaaauaaaca cauaaccuau aguuguagac aaaugguua gcagauguuu    300

ggacgugggu ucgacuccca ccggcucca                                      329
```

<210> SEQ ID NO 85

-continued

<211> LENGTH: 328
<212> TYPE: RNA
<213> ORGANISM: Staphylococcus epidermidis

<400> SEQUENCE: 85
caggggUccc cgagcuuauu aagcgugucg gaggguuggc uccgucauca acacauuucg 60
guuaaauaua acugacaaau caaacaauaa uuucgcagua gcugcguaau agccacugca 120
ucgccuaaca gcaucuccua cgugcuguua acgcgauuca acccuaguag gauaugcuaa 180
acacugccgc uugaagucug uuuagaugaa auauaaucaa gcuaguauca uguugguugu 240
uuauugcuua gcaugaugcg aaaauuauca auaaacuaca cacguagaaa gauuuguauc 300
aggaccucug gacgcggguu caacuccc 328

<210> SEQ ID NO 86
<211> LENGTH: 359
<212> TYPE: RNA
<213> ORGANISM: Staphylococcus aureus

<400> SEQUENCE: 86
ggggacguuc auggauucga caggggUccc ccgagcucau uaagcguguc ggaggguugu 60
cuucgucauc aacacacaca guuuauaaua acuggcaaau caaacaauaa uuucgcagua 120
gcugccuaau cgcacucugc aucgccuaac agcauuuccu augugcuguu aacgcgauuc 180
aaccuuaaua ggauaugcua aacacugccg uuugaagucu guuuagaaga aacuuaauca 240
aacuagcauc auguugguug uuuaucacuu uucaugaugc gaaaccuauc gauaaacuac 300
acacguagaa agauguguau caggaccuuu ggacgcgggu ucaaaucccg ccgucucca 359

<210> SEQ ID NO 87
<211> LENGTH: 334
<212> TYPE: RNA
<213> ORGANISM: Lactobacillus acidophilus

<400> SEQUENCE: 87
caggcguaga cccgcauuga cugcgguucg uagguuacgu cuacguaaaa acguuacagu 60
uaaauauaac ugcaaauaac aaaaauucuu acgcauuagc ugcuuaauuu agcgcaugcg 120
uugcucuuug ucgguuuacu cguggcugac acugaguauc aacuuagcga guuacguuua 180
acuaccucac cugaauaguu gaaaagaguc uuagcagguu agcuagucca uacuagcccu 240
guuauauggc guuuuggacu agugaaguuc aaguaauaua acuaugaucg uagaggucag 300
ugacgagaug cguuuggaca gggguucaac uccc 334

<210> SEQ ID NO 88
<211> LENGTH: 347
<212> TYPE: RNA
<213> ORGANISM: Aquifex aeolicus

<400> SEQUENCE: 88
gggggcggaa aggauucgac ggggacaggc gguccccgag gagcaggccg gguggcuccc 60
guaacagccg cuaaaacagc ucccgaagcu gaacucgcuc ucgcugccua auuaaacggc 120
agcgcguccc cgguagguuu gcgggUggcc uaccggaggg cgucagagac acccgcucgg 180
gcuacucggu cgcacggggc ugaguagcug acaccuaacc cgugcuaccc ucggggagcu 240
ugcccguggg cgacccgagg ggaaauccug aacacgggcu aagccuguag agccucggau 300
guggccgccg uccucggacg cggguucgau ucccgccgcc uccacca 347

<210> SEQ ID NO 89

-continued

<211> LENGTH: 355
<212> TYPE: RNA
<213> ORGANISM: Thermotoga maritima

<400> SEQUENCE: 89
gggggcgaac gguuucgacg gggauggagu ccccugggaa gcgagccgag guccccaccu 60
ccucguaaaa aaggugggac aaagaauaag ugccaacgaa ccuguugcug uugccgcuua 120
auagauaagc ggccguccuc uccgaaguug gcugggcuuc ggaagagggc gugagagauc 180
cagccuaccg auucaguucg ccuuccggcc ugaaucggga aaacucagga aggcuguggg 240
agaggacacc cugcccgugg gagguccuc ccgagagcga aaacacgggc ugcgcucgga 300
gaagcccagg ggccuccauc uucggacggg gguucgaauc cccccgccuc cacca 355

<210> SEQ ID NO 90
<211> LENGTH: 355
<212> TYPE: RNA
<213> ORGANISM: Thermotoga neapolitana

<400> SEQUENCE: 90
gggggcggaa aggauucgac ggggauggag uccccuggga agcgagccga gguccccacc 60
uccucguaaa aaagguggga acacgaauaa gugccaacga accuguugcu guugccgccu 120
aauagauagg cggccguccu cuccggaguu ggcugggcuc cggaagaggg cgugagggau 180
ccagccuacc gaucugggcu ccgccuuccg gcccggaucg ggaagguuca ggaaggcugu 240
gggaagcgac acccugcccg ugggggguccuuuccc gagac acgaaacacg ggcugcgcuc 300
ggagaagccc aggggccucc aucuucggac gggggguucga uucccgccgc cucca 355

<210> SEQ ID NO 91
<211> LENGTH: 350
<212> TYPE: RNA
<213> ORGANISM: Thermus thermophilus

<400> SEQUENCE: 91
gggggugaaa cggucucgac gggggucgcc gagggcgugg cugcgcgccg aggugcgggu 60
ggccucguaa aaacccgcaa cggcauaacu gccaacacca acuacgcucu cgcggcuuaa 120
ugaccgcgac cucgcccggu agcccugccg ggggcucacc ggaagcgggg acacaaaccc 180
ggcuagcccg gggccacgcc cucuaacccc gggcgaagcu ugaagggggc ucgcuccugg 240
ccgcccgucc gcgggccaag ccaggaggac acgcgaaacg cggacuacgc gcguagaggc 300
cacgccccgg cgaccuucgg acggggguuc gauuccccc accuccacca 350

<210> SEQ ID NO 92
<211> LENGTH: 349
<212> TYPE: RNA
<213> ORGANISM: Deinococcus radiodurans

<400> SEQUENCE: 92
gggggugacc cgguuucgac aggggaacug aaggugaugu ugcgugucga ggugccguug 60
gccucguaaa caaacggcaa agccauuuaa cuggcaacca gaacuacgcu cucgcugcuu 120
aagugagaug acgaccgugc agcccggccu uuggcgucgc ggaagucacu aaaaaagaag 180
gcuagcccag gcgauucucc auagccgacg gcgaaacuuu auggagcuac ggccugcgag 240
aaccugccca cuggugagcg ccggcccgac aaucaaacag ugggauacac acguagacgc 300
acgcuggacg gaccuuugga cggcgguucg acuccgccca ccuccacca 349

<210> SEQ ID NO 93

-continued

<211> LENGTH: 347
<212> TYPE: RNA
<213> ORGANISM: Deinococcus proteolyticus

<400> SEQUENCE: 93
gggggcggaa aggauucgac gggggaacgg aaagcgcugc ugcgugccga ggagccguug 60
gccucguaaa caaacggcaa agccauuaac uggcgaaaau aacuacgcuc ucgcugcuua 120
agugagagca gugaccacgu agccccgccu uuggcgacgu gugaacugag acaaaagaag 180
gcuagcuuag gugagguucc auagccaaaa gugaaaccaa auggaaauaa ggcggacggc 240
agccuguuug cuggcagccc aggcccgaca auuuaagagc agacuacgca cguagaugca 300
cgcuggaugg accuuuggac ggcgguucga uucccgccgc cucacca 347

<210> SEQ ID NO 94
<211> LENGTH: 334
<212> TYPE: RNA
<213> ORGANISM: Thermomicrobium roseum

<400> SEQUENCE: 94
cagggccgua ggugcgagga uugcaggucg aggucgccca cgaacucgua aaaaggggca 60
ccaaguaacu ggcgagcgcg aacucgcucu ggcugcguaa uucacgcagc cacgucugcc 120
cggacccuuc ccuggugggu ucggagcggg cgccgcaaga ccggggugcc ccuggcccaa 180
gcgccggugc gggccagguc aagcgugauc cggcucggcu gaccgggauc cugucggugg 240
gagccuggca gcgacaguag aacaccgacu aagccuguag cauauccucg gcugaacgcu 300
cuggacgggg guucaacucc cgccagcucc acca 334

<210> SEQ ID NO 95
<211> LENGTH: 353
<212> TYPE: RNA
<213> ORGANISM: Coprothermobacter proteolyticus

<400> SEQUENCE: 95
gggggcggaa aggauucgac ggggagucgg agccuugagc ugcaggcagg guuggcugcc 60
acaccuuaaa aaggguagca aggcaaaaau aaaugccgaa ccagaauuug cacuagcugc 120
uuaauguaag cagccgcucu ccaaacugag gcugcauaag uuuggaagag cgucaaccca 180
ugcagcggcu cuuaagcagu ggcaccagcu guuuaagggu gaaaagagug gugcugggca 240
gugcgguugg gcuuccuggg cugcacuguc gagacuucac aggagggcua agccuguaga 300
cgcgaaaggu ggcggcucgu cggacgcggg uucgauuccc gccgccucca cca 353

<210> SEQ ID NO 96
<211> LENGTH: 360
<212> TYPE: RNA
<213> ORGANISM: Herpetosiphon aurantiacus

<400> SEQUENCE: 96
gggggcggaa aggauucgac ggggagggcc aaucguaagu ggcaagccga gacgcugagc 60
cucguuaaau cggcaacgcc auuaacuggc aaaaacacuu uccgcgcucc uguagcgcuu 120
gcugccuaau uaaggcaaca cgucucuacu agccucagcc cgaugggcuu guagcggcga 180
cacuuagucg ggucgcuccc cuaguuaugu cugugggcua ggggcuaaga uuaacaggcu 240
ggucguggcc cgcuuugucu aucgggugu gcaccgauaa gauuuaauca auagacuacg 300
cuuguagaug cuugcgguuu aacuuuuugg acgcggguuc gauucccgcc gccuccacca 360

<210> SEQ ID NO 97

<211> LENGTH: 355
<212> TYPE: RNA
<213> ORGANISM: Thermodesulfobacterium commune

<400> SEQUENCE: 97
gggggcggaa aggauucgac ggggauaggu aggauuaaac agcaggccgu ggucgcaccc 60
aaccacguua aauagggugc aaaaacacaa cugccaacga auacgccuac gcuuuggcag 120
ccuaagcgug cugccacgca ccuuuagacc uugccugugg gucuaaaggu gugugaccua 180
acaggcuuug ggaggcuuaa ucgguggggu uaagccuccc gagauuacau cccaccuggu 240
aggguugcuu ggugccugug acaagcaccc uacgagauuu ucccacaggc uaagccugua 300
gcgguuuaau cugaacuauc uccggacgcg gguucgauuc ccgccgccuc cacca 355

<210> SEQ ID NO 98
<211> LENGTH: 329
<212> TYPE: RNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 98
gggnnnnauu uggaauucgc cgaaugcuag aaguggaggc ugcaugccgc ggaugauucg 60
uuggccgcuu uaccaauucg gaucaaacaa cuaaaugcgg acucuaacga gcuugcccuc 120
gccgcuuaau ugacggugac guuccuccag ugaagucugu gaauuggagg agcgacuacu 180
uacaggcugg ccaaaagagc gggcgaccgg ccccaaggcg agaucuacag gccgcuggau 240
ggacggcauc cuggcaguag gaggcuggac aucgagauca aaunauugcc ugagcaugga 300
gacgcuuuca uaaaggnguu cggacaggg 329

<210> SEQ ID NO 99
<211> LENGTH: 351
<212> TYPE: RNA
<213> ORGANISM: Dictyoglomus thermophilum

<400> SEQUENCE: 99
gggggcggaa aggauucgac ggggaguaca aggaucaaaa gcugcaagcc gaggugccgu 60
uaccucguaa aacaacggca aaaaagaagu gccaacacaa auuuagcauu agcugcuuaa 120
uuuagcagcu acgcucuucu aacccgggcu ggcaggguua gaagggug uc auaaugagcc 180 agcugccccu uccgacuccc cuaaggaagg gaaagaugua ggggauaggu gcuuacagaa 240
uccugcggga gggagucugu aagugccgaa aaguuaaaac ucccgcuaag cuuguagagg 300
cuuuugauuc uugcucucug gacgcggguu cgauucccgc cgccuccacc a 351

<210> SEQ ID NO 100
<211> LENGTH: 399
<212> TYPE: RNA
<213> ORGANISM: Synechocystis sp. PCC 6803

<400> SEQUENCE: 100
ggggccgcaa ugguuucgac agguuggcga aagcuugccc gugauacagg ucgagaguga 60
gucuccucuc gcaaaucaaa ggcucaaaaa aaaguaacug cgaauaacau cgucagcuuc 120
aaacggguag ccauagcagc cuagucugua aaagcuacau uuucuuguca aagaccguuu 180
acuucuuuuc ugacuccguu aaggauuaga gguuaacccc aacggaugcu uuguuuggcu 240
cuucucuagu uagcuaaaca aucaagacuc agacuagagc aucccaccau cagggauaau 300
cgauggaccc cguccuaggg cuagaaggac uaaaccugug aaugagcgga aaguuaaauac 360 ccaguuugga cagcaguuca auucugcucg gcuccacca 399

<210> SEQ ID NO 101
<211> LENGTH: 385
<212> TYPE: RNA
<213> ORGANISM: Nostoc muscorum

<400> SEQUENCE: 101
ggguccgucg guuucgacag guuggcgaac gcuacucugu gauucagguc gagagugagu 60
cuccucugca aaucaaggcu caaaacaaaa guaaaugcga auaacaucgu uaaauuugcu 120
cguaaggacg cucuaguagc ugccuaaaua gccucuuuca gguucgagcg ucuucgguuu 180
gacuccguua aggacugaag accaaccccc aacggaugcu cuagcaaugu ucucugguug 240
gcuugcuagc uaagauuuaa ucagagcauc cuacguucgg gauaaugaac gauucccgcc 300
uugaggguca gaaaggcuaa accugugaau gagcgggggg ucaauaccca auuuggacag 360
caguucgacu cugcucgauc cacca 385

<210> SEQ ID NO 102
<211> LENGTH: 393
<212> TYPE: RNA
<213> ORGANISM: Synechococcus PCC 6301

<400> SEQUENCE: 102
ggggcuguaa ugguuucgac guguugguga auccuucacc gugauucagg ccgagaggga 60
guccacucuc guaaauccag gcucaaccaa aaguaacugc gaacaacauc guuccuuucg 120
cucguaaggc ugcuccugua gcugcuuaaa cgccacaaac uuucuggcuc gagcgucuag 180
ucguagacuc cguuaauacg ccuagacuua aaccccccaac ggaugcugag uggcggccuc 240
agguccgucc ucucgcuaag caaaaaccug agcaucccgc caacggggau aaucguuggc 300
ucccgcacag ugggucaacc gugcuaagcc ugugaacgag cggaaaguua cuagucaaug 360
cggacagcgg uucgauuccg cucagcucca cca 393

<210> SEQ ID NO 103
<211> LENGTH: 312
<212> TYPE: RNA
<213> ORGANISM: Leptolyngbya sp. (ATCC 27894)

<400> SEQUENCE: 103
ggcucaaaaa aauagaugca aacaacaucg uaccuuucgc ucguaaaacu gcaccuguug 60
cagcauaaaa caccucuaau ucagguucga gcgcuuaccg ucugacaccg uuaaagauag 120
uaagcacaac cccaacgguu gcucuagaau uucgccuuug gucggcauuc uagcuaagac 180
aauaccaaag cauccuauug uccgggacaa aggacaguuc ccgcuucgag gauuagagaa 240
gcuaaaccug ugaaugauug auagagcuaa uacccaguuu ggacacgggu ucaacucccg 300
ccagcuccac ca 312

<210> SEQ ID NO 104
<211> LENGTH: 323
<212> TYPE: RNA
<213> ORGANISM: Porphyra purpurea

<400> SEQUENCE: 104
ggggcugcaa gguuucuaca uugugaaaaa acaaauauau gaaaguaaaa cgagcucauu 60
auuagagcuu uuaguuaaau aaaugcagaa aauaauauua uugcuuuuuc ucgaaaauua 120

-continued

```
gcuguugcau aaauagucuc aauuuuugua auucgaagug auagacucuu auacacuacg    180

aauauucugu uagaguugcu cuuaauaaaa gaaaaguaaa aaaauacaaa uucuuauguu    240

uuuuaccuga auugauucaa uuuaagguua guauuuuuug auuuuuacaa uggacguggg    300

uucaaguccc accagcucca cca                                            323


<210> SEQ ID NO 105
<211> LENGTH: 294
<212> TYPE: RNA
<213> ORGANISM: Cyanophora paradoxa

<400> SEQUENCE: 105

ggggcuguuu agguuucgac guuuuuuucu aauuauguuu guuaagcaag ucgaggauuu     60

guucuaucuc gaaaaucaag aacucucaaa auuuaaacgc aacuaauauu guacguuuua    120

accguaaagc agcuuucgcu guuuaauaau uacuuuuaau uuaaaaaccu aauuuuuuua    180

ggaauuuauu uauuuauugu uuauccugcu uaaugaauua aaaaaagcua uacuugugaa    240

uaaacgcaua auuuaaaaaa acggacgugg guucaaaucc caccagcucc acca          294


<210> SEQ ID NO 106
<211> LENGTH: 371
<212> TYPE: RNA
<213> ORGANISM: Odontella sinensis

<400> SEQUENCE: 106

ggggcugacu ugguuucgac auuuaaaaau uguuacagua ugaugcaggu cgaaguuucu     60

aaucuucgua aaaaaagaga aauuuauaau aaaugcuaau aauuuaauuu cuucuguguu    120

uaaaaguuua ucaacuaagc aaaauaguuu aaauuuaagu uuugcuguuu aaguuuuaug    180

cacauuuaau gaucuaguaa auaacuuugu ucgcuauaau uuauauuuau aacuagacuu    240

uugucuuuuu uauaguuuag aauaacuuua ucauuucaaa ccucguucca ucuaguugaa    300

cuaaaccugu gaacgaauac uauaauaaaa uuuuuagaug gacgugggu cgacucccau     360

cagcuccacc a                                                         371


<210> SEQ ID NO 107
<211> LENGTH: 348
<212> TYPE: RNA
<213> ORGANISM: Thalassiorsira weissflogii

<400> SEQUENCE: 107

ggggcugauu ugguuucgac auuuaaaacu ucuuucuaug ugucagguca aaguuuguau     60

ucuuuguaaa aaaauacuaa aauacuaaua aaugcuaaua auauaauacc guuuauuuuu    120

aaagcaguaa aaacaaaaaa agaagcaaug gcuuuaaauu uugcuguaua guucauuaac    180

uuagguuauu aaauauuuuu ucauuauaac uggacuuuuu cucaguuuau aguuuagaau    240

aaauuuaaau uuugcaaaac ucguucgaaa auuuucgggc uaaaccugua aacgcaaaua    300

cuaagaaauu uuagauggac augggguucaa uucccaucag uuccacca                348


<210> SEQ ID NO 108
<211> LENGTH: 330
<212> TYPE: RNA
<213> ORGANISM: Guillardia theta

<400> SEQUENCE: 108

ggggcugauu uggauucgac auauaaauuu gcguguuuca uuaugaagca agucaaguuu     60

aaugaucuug uaaaaaacau uaaaguacaa auaaaugcaa gcaauauagu uucauuuagu    120
```

-continued

```
ucaaaacguu uagucucuuu ugcauaagca aaauguguua auaacuuucu uaguagaaau    180

uggagaaguu uacuaagauu uauauuuacu ccauaauuau uuuaaagaug guaaaaaggu    240

gauucaucau uuguauguuu cuaaacuuug ugaaagaaua gugggcucca uuuauaauga    300

acgugggguuc aaaucccacc agcuccacca                                   330
```

<210> SEQ ID NO 109
<211> LENGTH: 353
<212> TYPE: RNA
<213> ORGANISM: Mycoplasma hyorhinis

<400> SEQUENCE: 109

```
cauacauaaa aggauauaaa uugcaguggu cuuguaaacc auaagacaau uucuuuacua     60

agcggaaaag aaaacaaaaa agaagauuau ucauuauuaa ugaaugcuuc aacucaauca    120

aaucuagcuu uugcauuuua aaaaacuagu agaccaauuu gcuucucacg aauuguaaauc    180

uuuauauuag agaauaguua aaaaucugau cacuuuuuaa ugaauuuaua gaucacaggc    240

uuuuuuaauc uuuuuguuau uuuagauaaa gagucuucuu aaaaauaacu aaacuguagg    300

aauuuauauu uaauuaugcg uggacccggg uucaacuccc gccagcucca cca           353
```

<210> SEQ ID NO 110
<211> LENGTH: 411
<212> TYPE: RNA
<213> ORGANISM: Mycoplasma capricolum

<400> SEQUENCE: 110

```
ggggauguca uggauuugac aggauaucuu uaguacauau aagcaguagu guuguagacu     60

auaaauacua cuagguuuaa aaaaacgcaa auaaaaacga agaaacuuuu gaaaugccag    120

cauuuaugau gaauaaugca ucagcuggag caaacuuuau guuugcuuaa uaacuacuag    180

uuuaguuaua guauuucacg aauuauagau auuuuaagcu uuauuuauaa ccguauuacc    240

caagcuuaau agaauauaug auugcaauaa auauauuuga aaucuaauug caaaugauau    300

uuaaccuuua guuaauuuua guuaaauauu uuaauuagaa aauuaacuaa acuguagaaa    360

guauguauua auauaucuug gacgcgaguu cgauucucgc caucuccacc a             411
```

<210> SEQ ID NO 111
<211> LENGTH: 381
<212> TYPE: RNA
<213> ORGANISM: Mycoplasma pirum

<400> SEQUENCE: 111

```
caugaaugau ggacccauag aggcaguggg guaugccccu uauagcucaa gguuuaaauu     60

aaccgacaaa acugacgaaa acguugccgu ugauacaaau uuauuaauca accaacaagc    120

ucaauuuaac uacgcauuug cauaguauaa aaaaauaaau ugugcuacuc auuguaauua    180

gguuacuaaa uuacuuuguu uuauauaguc cuguaacuag uucuagugau gucuauaaac    240

uagaaugaga uuuauagacu uauuuguugg cgguugugcc auagccuaaa ucaacaaaga    300

caauuuauuu augguacuaa acuguagauu cuaugaugaa auuauuugug gaaacggguu    360

cgauucccgc caucuccacc a                                              381
```

<210> SEQ ID NO 112
<211> LENGTH: 387
<212> TYPE: RNA
<213> ORGANISM: Mycoplasma pneumoniae

<400> SEQUENCE: 112

-continued

```
gggGauguag agguuuugac auaauguuga aaggaaaaca guugcagugg gguaugcccc     60

uuacagcucu agguauaaua accgacaaaa auaacgacga aguuuuggua gauccaaugu    120

ugaucgcuaa ccaacaagca aguaucaacu acgcuuucgc uuagaacaua cuaaagcuac    180

acgaauugaa ucgccauagu uugguucgug ucacaguuua uggcucgggg uuaacugguu    240

caacuuaauc cuuaaauuau gaacuuaucg uuuacuuguu ugucuuauga ucuaaaguaa    300

gcgagacauu aaaacauaag acuaaacugu agaagcuguu uuaccaaucc uuuauggaaa    360

cgguucgau ucccgucauc uccacca                                         387
```

<210> SEQ ID NO 113
<211> LENGTH: 388
<212> TYPE: RNA
<213> ORGANISM: Mycoplasma genitalium

<400> SEQUENCE: 113

```
ggggauguuu uggguuugac auaaugcuga uagacaaaca guagcauugg gguaugcccc     60

uuacagcgcu agguucaaua accgacaaag aaaauaacga aguguuggua gauccaaauu    120

ugaucauuaa ccaacaagca aguguuaacu uugcuuuugc auaaguagau acuaaagcua    180

cagcugguga auagucauag uuugcuagcu gucauaguuu augacucgag guuaaaucgu    240

ucaauuuaac cuuuaaaaau agaacuuguu guuuccauga uuguuuugug aucaauugga    300

aacaagacaa aaauccacaa aacuaaaaug uagaagcugu uuguuguguc cuuuauggaa    360

acggguucga uucccgucau cuccacca                                       388
```

<210> SEQ ID NO 114
<211> LENGTH: 412
<212> TYPE: RNA
<213> ORGANISM: Ureaplasma urealyticum

<400> SEQUENCE: 114

```
ggggauguca cgguuucgac gugacacauu aauuuuuaau ugcagugggg uuagccccuu     60

aucgcuuucg aggcauuuua aaugcagaaa auaaaaaaauc uucugaagua gaauuaaacc    120

cagcguuuau ggcuucagcu acuaaugcaa acuacgcuuu ugcguacuaa uuaguuauua    180

guagaaacgu ucauuaacau aauuacuauu gguugguuuu ugggcuuauu uuacaauagu    240

uuuaaauuua aaauucuuau uguuguuuaa auuuaaauag auuuaacaaa uaguuaguua    300

auuuuaaauu uguuuuauua guuauuaacu acacuauuuu uaauaaaacu aaacuguaga    360

uauuauuaau uauguguugc ggaaaggggu ucgauucccc ucaucuccac ca            412
```

<210> SEQ ID NO 115
<211> LENGTH: 365
<212> TYPE: RNA
<213> ORGANISM: Mycoplasma salivarium

<400> SEQUENCE: 115

```
caggcauucg auucauuaug uugcaguggu uugcaaacca uaaggcacua ggcuuuuuua     60

aacgcaaaag accaaaaaac agaagaucaa gcaguugauc uagcauuuau gaauaauuca    120

caaaugcaau caaaucuagu uuucgcuuag uaaaauuagu caauuuauua uggugcucaa    180

cauaauaaau gguaguauga gcuuaauauc auaugauuuu aguuaauaug auaggauuug    240

uaacuaaacu auguuauaga aauuuguaaa uuauauauau gacauaggaa auuuaauuua    300

cuaaacugua gaugcauaau guugaagaug uguggaccgg gguucaacuc ccgccagcuc    360

cacca                                                                365
```

<210> SEQ ID NO 116
<211> LENGTH: 363
<212> TYPE: RNA
<213> ORGANISM: Clostridium innocuum

<400> SEQUENCE: 116
cggggauaug ucugguacag acugcagucg agugguuacg uaauaaccaa uuaaauuuaa 60
acggaaaaac uaaauuagcu aaccucuuug guggaaacca gagaauggcu uucgcugcuu 120
aauaaccgau auagguucgc agccgccucu gcaugcuucu uccuugacca uguggaugug 180
cgcguaagac gcaagggaua aggaaucugg uuugccugag aucagauuca cgaaaauucu 240
ucaggcacau ucaucagcgg auguucauga ccugcugaug ucuuaaucuu cauggacuaa 300
acuguagagg ucuguacgug ggcuguuuc uggacaggag uucgauuccc gccgccucca 360
cca 363

<210> SEQ ID NO 117
<211> LENGTH: 359
<212> TYPE: RNA
<213> ORGANISM: Mycoplasma fermentans

<400> SEQUENCE: 117
caugcauugg gugauacuaa uaucaguagu uuggcagacu auaaugcauc uaggcuuuau 60
aaucgcagaa gauaaaaaag cagaagaagu uaauauuucu ucacuuauga uugcacaaaa 120
aaugcaauca caaucaaacc uugcuuucgc uuaguuaaaa gugacaagug guuuuaaagu 180
ugacauuuuc cuauauauuu uaaaaucggc uuuuaaggag aacaggaguc ugaaaggguu 240
ccaaaaaucu auauuguuug cauuucggua guauagauua auuagaaaug auaaacugua 300
aaaaguauug guauugacuu ggugugugga cucggguuca acucccgcca gcuccacca 359

<210> SEQ ID NO 118
<211> LENGTH: 320
<212> TYPE: RNA
<213> ORGANISM: Acidobacterium capsulatum

<400> SEQUENCE: 118 cggggguugac ugcggcaaag aggcaugccg gggggugggc acccguaauc gcucgcaaaa 60
caauacuugc caacaacaau cuggcacucg cagcuuaauu aaauaaguug ccguccucug 120
aggcuucgcc ugugggccga ggcaggacgu cauacagcag gcugguuccu ucggcugggu 180
cugggccgcg gggaugagau ccacggacua gcauucugcg uaucuugucg cuucuaagcg 240
cagagugcga aaccuaaagg aaugcgacug agcauggagu cucuuuucug acaccaauuu 300
cggacgcggg uucgauuccc 320

<210> SEQ ID NO 119
<211> LENGTH: 319
<212> TYPE: RNA
<213> ORGANISM: Fusobacterium mortiferum

<400> SEQUENCE: 119
cgggguuaug agguuauagg uagcaugcca ggaugaccgc ugugagaggu caacacaucg 60
uuuagaugga aacagaaauu acgcuuuagc ugcuuaauua gucagcucac cucugguuuc 120
ucucuucugu aggagaaucc aaccgaggug uuaccaauau acagauuacc uuuagugauu 180
ucucuaagcu caaagggaca uuuuagagaa uagcuucagu uagcccuguc ugcgggagug 240
auuguugcga aauaaaauag uagacuaagc auuguagaag ccuauggcgc ugguaguuuc 300
ggacacgggu ucaacuccc 319

<210> SEQ ID NO 120
<211> LENGTH: 329
<212> TYPE: RNA
<213> ORGANISM: Fibrobacter succinogenes

<400> SEQUENCE: 120
caggguuacc gaaguguuag uugcaagucg aggucucaga cgagggcuac ucguuaaaaa 60
gucugaaaaa aaauaagugc ugacgaaaac uacgcacucg cugccuaauu aacggcaacg 120
ccgggccuca uuccgcuccc aucggggugu acguccggac gcaauauggg auagggaagu 180
gucaugccug ggggcaucuc ccgagauuuu cuaggcuggu caaacuccgc gccgaccuuc 240
uugggcgugg auaagacgag aucuuaaauu cgaagggaac acuuguagga acguacaugg 300
acgugauuuu ggacaggggu ucaacuccc 329

<210> SEQ ID NO 121
<211> LENGTH: 300
<212> TYPE: RNA
<213> ORGANISM: Artificial
<220> FEATURE:
<223> OTHER INFORMATION: isolated from rumenal fluid

<400> SEQUENCE: 121
acgcccuugu cucagacgag ggcacucguu aaaaagucug aaaagaauaa cugcagaacc 60
uguagcuaug gcugcuuaau uuaagggcaa cccuuggauc cgccuccauc ccgaaggggu 120
ggcauccgag ucgcaaaucg ggauaggaug gaucuuggca acgaggagua cauccgaaau 180
uugucgcugc uggcugaagc aucgccguuc cucuuugggc guggcaaggc aagauuaaau 240
ucagaggaua agcguguagu agcgagugag uagguguuuu uggacgcggg uucaaguccc 300

<210> SEQ ID NO 122
<211> LENGTH: 330
<212> TYPE: RNA
<213> ORGANISM: Pirellula staleyi

<400> SEQUENCE: 122
ccggauagcc ugaagcgaau acggcgugcc gugguugauc agauggccac guaaaaagcu 60
gaucacaaac uuaacugccg agagcaaucu cgcacuugcu gccuaacuaa acgguagcuu 120
ccgacugagg gcuuuagccg gagaggccca aaaguugguc accaaauccg gaccgccucg 180
ugccaugauc gaaacgcacg aggucaaaaa aguuucgauc uagugcaggg uguagccagc 240
agcuaggcga caaacugugc aaaaaucaaa uuuucugcua cgcacguaga uguguucgug 300
aaaaugucuc gggacggggg uucaacuccc 330

<210> SEQ ID NO 123
<211> LENGTH: 329
<212> TYPE: RNA
<213> ORGANISM: Planctomyces maris

<400> SEQUENCE: 123
cugguucacc guauguuaag guggcggugc cgugguugau caguuggcca cguaaaaagc 60
ugaucacaau cuaauugcaa acaagcaauu uucaauggcu gcuuaauaaa agcaaccccg 120
gcuuaggaau cucugucuga ggaguccgac agcuggucac aaaaucagac ugguaucaga 180
ucaauguccg cuccgucuga uacgagauuc gugguggacu gguuuccaac aggcucuguu 240
uaucgugccc gaagaaacga gacucaaacg auaaaaauag caccguagag gcuuuagcug 300
aggguucaca ggacgcgggu ucaacuccc 329

<210> SEQ ID NO 124
<211> LENGTH: 318
<212> TYPE: RNA
<213> ORGANISM: Artificial
<220> FEATURE:
<223> OTHER INFORMATION: isolated from sludge

<400> SEQUENCE: 124
cagggaacca ggaggugaga gaugcaugcc ggagacgcug uccgcuccgu uaucaagcag 60
cacaacaaaa uaauugcaaa caacaauuac uccuuagcag cguaagcagc uaacguucaa 120
ccucuccgga ccgccgggag gggauuuggg cgucgaaaca gcgcggacgc uccggauagg 180
acgcccauaa uauccggcua agaccauggg ucuggcucuc gcgggucuga uugucuucca 240
ccgcgcgggc cgcgaucaaa gacaacuaag cauguagguu cuugcauggc cuguucuuug 300
gacgcggguu cgauuccc 318

<210> SEQ ID NO 125
<211> LENGTH: 407
<212> TYPE: RNA
<213> ORGANISM: Porphyromonas gingivalis

<400> SEQUENCE: 125
ggggcugacc ggcuuugaca gcgugaugaa gcgguaugua agcauguagu gcgugggugg 60
cuugcacuau aaucucagac aucaaaaguu uaauuggcga aaauaacuac gcucucgcug 120
cguaaucgaa gaauaguaga uuagacgcuu caucgccgcc aaaguggcag cgacgagaca 180
ucgcccgagc agcuuuuucc cgaaguagcu cgauggugcg gugcugacaa aucgggaacc 240
gcuacaggau gcuuccugcc uguggucaga ucgaacggaa gauaaggauc gugcauuggg 300
ucguuucagc cuccgcucgc ucacgaaaau uccaacugaa acuaaacaug uagaaagcau 360
auugauucca uguuuggacg aggguucaau ucccuccagc uccacca 407

<210> SEQ ID NO 126
<211> LENGTH: 379
<212> TYPE: RNA
<213> ORGANISM: Bacteroides thetaiotaomicron

<400> SEQUENCE: 126
cagcgggcag aaaugguagg uaagcaugca gugggucggu aauuuccacu uaaaucucag 60
uuaucaaaac uuuaucuggc gaaacuaauu acgcucuugc ugcuuaaucg aaucacagua 120
gauuagcuua auccaggcac uaggugccca ggagagacau cacucggaag cuguugcucc 180
gaagcauucc gguucagugg ugcaguaaca ucggggauag ucagaagcgg ccucgcguuu 240
uugaugaaac uuuagaggau aaggcaggaa uugauggcuu ugguucugcu ccugcacgaa 300
aauuuaggca aagauaagca uguagaaagc uuaugauuuc cucguuugga cgaggguuca 360
acucccgcca gcuccacca 379

<210> SEQ ID NO 127
<211> LENGTH: 404
<212> TYPE: RNA
<213> ORGANISM: Chlorobium tepidum

<400> SEQUENCE: 127
ggggaugaca ggcuaucgac aggauaggug ugagaugucg uugcacuccg aguuucagca 60
uggacggacu cguuaaacaa gucuauguac caauagaugc agacgauuau ucguaugcaa 120

```
uggcugccug auuagcacaa guuaauucag aagccaucgu ccugcgguga augcgcuuac    180

ucugaagccg ccggauggca uaacccgcgc uugagccuac ggguucgcgc aaguaagcuc    240

cguacauuca ugcccgaggg ggugugcggg uaaccaaucg ggauaagggg acgaacgcug    300

cuggcggugu aaucggacca cgaaaaacca accaccagag augagugugg uaacugcauc    360

gagcaguguc cuggacgcgg guucaagucc cgccaucucc acca                     404
```

<210> SEQ ID NO 128
<211> LENGTH: 372
<212> TYPE: RNA
<213> ORGANISM: Chlorobium limicola

<400> SEQUENCE: 128

```
caggauacgu gugagauguc guugcacucc gaguuucagc auggacggac ucguuaaaca     60

agucuaugua ccauuagaug cagacgauua uucguaugca auggcugccu gauuagcaca    120

aguuaacuca gacgccaucg uccugcggug aaugcgcuua cucugaagcc gccggauggc    180

auaacccgcg cuugagccua cggguucgcg caaguaagcu ccguacauuc augcccgagg    240

ggcugugcgg guaauuucuc gggauaaggg gacgaacgcu gcuggcggug uaaucggccc    300

acgaaaaccc aaucaccaga gaugagugug gugacugcau cgagcagugu uuuggacgcg    360

gguucaacuc cc                                                        372
```

<210> SEQ ID NO 129
<211> LENGTH: 420
<212> TYPE: RNA
<213> ORGANISM: Chlamydia trachomatis

<400> SEQUENCE: 129

```
gggggguaa agguuucgac uuagaaauga agcguuaauu gcaugcggag ggcguuggcu     60

ggccuccuaa aaagccgaca aaacaauaaa ugccgaaccu aaggcugaau gcgaaauuau    120

cagcuucgcu gaucucgaag aucuaagagu agcugcuuaa uuagcaaagu uguuaccuaa    180

auacgggug  cccggguuc gcgagcucca ccagagguuu ucgaaacacc gucauguauc    240

ugguuagaac uuagguccuu uaauucucga ggaaaugagu uugaaauuua augagagucg    300

uuagucucua uaggggguuuc uagcugagga gacauaacgu auaguaccua ggaacuaagc    360

auguagaggu uagcggggag uuuacuaagg acgagaguuc gacucucucc accuccacca    420
```

<210> SEQ ID NO 130
<211> LENGTH: 421
<212> TYPE: RNA
<213> ORGANISM: Artificial
<220> FEATURE:
<223> OTHER INFORMATION: Chlamydia trachomatis mouse isolate

<400> SEQUENCE: 130

```
gggggguaa agguuucgac uuagaaauga agcguuaauu gcaugcggag ggcguuggcu     60

ggccuccuaa aaagccgaca aaacaauaaa ugccgaaccu aaggcugaau gcgaaauuau    120

cagcuucgcu gaucuuaaug aucuaagagu ugcugcuuaa uuagcaaagu uguuaccuaa    180

guacugguaa cccggguuc gcgagcucca ccagagguuu ucgaaacgcc gucauuuauc    240

ugguuagaau uagggccuuu uaacucucaa gggaacuaau uugaauuuua augagagucg    300

uuggucucua uagagguuuc uagcugagga gauauaacgu aaaauauucu agaaacuaag    360

cauguagagg uuagcgggga guuuacuaag gacgagaguu cgaaucucuc caccuccacc    420

a                                                                    421
```

<210> SEQ ID NO 131
<211> LENGTH: 426
<212> TYPE: RNA
<213> ORGANISM: Chlamydia pneumoniae

<400> SEQUENCE: 131 gggggguguau agguuucgac uugaaaauga aguguuaauu gcaugcggag ggcguuggcu 60
ggccuccuaa aaagccaaca aaacaauaaa ugccgaaccu aaggcugaau gcgaaauuau 120
uagcuuguuu gacucaguag aggaaagacu agcugcuuaa uuagcaaaag uuguuagcua 180
gauaaucucu agguaacccg guaucugcga gcuccaccag aggcuugcaa aauaccguca 240
uuuaucuggu uggaacuuac uuucucuaau ucucaaggaa guucguucga gauuuuugag 300
agucauuggc ugcuauagag gcuucuagcu aagggagucc aauguaaaca auucuagaag 360
auaagcaugu agagguuagc agggaguuug ucaaggacga gaguucgagu cucuccaccu 420
ccacca 426

<210> SEQ ID NO 132
<211> LENGTH: 328
<212> TYPE: RNA
<213> ORGANISM: Micrococcus luteus

<400> SEQUENCE: 132
cggugugugu cgcgucggga gaagcgggcc gaggaugcag agucaucucg ucaaacgcuc 60
ucugcaaacc aauaagugcc gaauccaagc gcacugacuu cgcucucgcu gccugaucag 120
ugaucgaguc cgucaccccg aggucgcugu cgccucggau cguggcguca gcuagauagc 180
cacugggcgu cacccucgcc gggggucgug acgccgacau caauccggcu ggguccgggu 240
uggccgcccg ucugcgggac ggccaggacc gagcaacacc cacagcagac ugcgcccgga 300
gaagaccugg caacaccuca ucggacgc 328

<210> SEQ ID NO 133
<211> LENGTH: 368
<212> TYPE: RNA
<213> ORGANISM: Mycobacterium leprae

<400> SEQUENCE: 133
ggggcugaaa gguuucgacu ucgcgcaucg aaucaaggga agcgugccgg ugcaggcaag 60
agaccaccgu aagcgucguu gcagcaauau aagcgccgau ucauaugagc gcgacuaugc 120
ucucgcugcc uaagcgaugg cuagucuguc agaccgggaa cgcccucguc ccggagccug 180
gcaucagcua gagggaucua ccgaugggu cggucgcggg acucgucggg acaccaaccg 240
cgacugggau cgucauccug gcuaguucgc gugaucagga gauccgagua gaggcauagc 300
gaacuacgca cggagaagcc uugagggaaa ugccguagga cccggguucg auucccggca 360
gcuccacc 368

<210> SEQ ID NO 134
<211> LENGTH: 360
<212> TYPE: RNA
<213> ORGANISM: Mycobacterium tuberculosis

<400> SEQUENCE: 134
ggggcugaac gguuucgacu ucgcgcaucg aaucaaggga agcgugccgg ugcaggcaag 60
agaccaccgu aagcgucguu gcgaccaaau aagcgccgau ucacaucagc gcgacuacgc 120
ucucgcugcc uaagcgacgg cuagucuguc agaccgggaa cgcccucggc ccggacccug 180
gcaucagcua ccaccgauga guccggucgc gggacuccuc gggacaacca cagcgacugg 240
gaucgucauc ucggcuaguu cgcgugaccg ggagauccga gcagaggcau agcgaacugc 300
gcacggagaa gccuugaggg aaugccguag gacccggguu cgauucccgg cagcuccacc 360

<210> SEQ ID NO 135
<211> LENGTH: 373
<212> TYPE: RNA
<213> ORGANISM: Mycobacterium avium

<400> SEQUENCE: 135
ggggcugaaa gguuucgacu ucgcgcaucg aaucaaggga agcgugccgg ugcaggcaac 60
ugaccaccgu aagcgucguu gcagauagau aagcgccgau ucacaucagc gcgacuacgc 120
ucucgcugcc uaagcgacag cuagucgagg gaucgucagc ccgggaacgc ccucgacccg 180
gagccuggcg ucagcuagag ggauccaccg augaguucgg ucgcgggacu caucgggaca 240
ccaacagcga cugggaucgu cauccuggcu uguucgcgug accaggagau ccgaguagag 300
gcauagcgaa cugcgcacgg agaagccuug agggaaugcc guaggacccg gguucgauuc 360
ccggcagcuc cac 373

<210> SEQ ID NO 136
<211> LENGTH: 331
<212> TYPE: RNA
<213> ORGANISM: Corynebacterium xerosis

<400> SEQUENCE: 136
cuucguacau ugagccaggg gaagcgugcc ggugaaggcu ggagaccacc gcaagcgucg 60
cagcaaccaa uuaagcgccg agaacucuca gcgcgacuac gcccucgcug ccuaagcagc 120
gaccgcgugu cugucagacc ggguaggccu cugauccgga cccuggcauc guuuaguggg 180
gcucgcucgc cgacuugguc gcaagggucg gcggggacac ucacuugcga cugggcccgu 240
cauccgguca uguucgacug aaccggaggg ccgagcagag accacgcgcg aacugcgcac 300
ggagaagccc uggcgaggug acggaggacc c 331

<210> SEQ ID NO 137
<211> LENGTH: 354
<212> TYPE: RNA
<213> ORGANISM: Treponema pallidum

<400> SEQUENCE: 137
ggggaugacu agguuucgac uagggaugug ggguguugcg cugcaggugg agugucgauc 60
uccugauucg gcgccuuuau aacugccaau ucugacaguu ucgacuacgc gcucgccgcg 120
uaaucgcggg ccuguguuug cgcugcucug agcgaacaua ucggcccgac gccaaacgga 180
gcuugcucuu acguugugca cggcggacgu agggggacuu uugucugugc uaagacucug 240
gcgcgugcgg ugcaggccua gcagaguccg acaaacgcag uacgcaccgc uaaaccugua 300
ggcgcgcagc acucgcucuu uaggacgggg guucgauucc ccccaucucc acca 354

<210> SEQ ID NO 138
<211> LENGTH: 362
<212> TYPE: RNA
<213> ORGANISM: Borrelia burgdorferi

<400> SEQUENCE: 138
ggggauguuu uggauuugac ugaaaauguu aauauuguaa guugcaggca gagggaaucu 60
cuuaaaacuu cuaaaauaaa ugcaaaaaau aauaacuuua caagcucaaa ucuuguaaug 120

```
gcugcuuaag uuagcagagg guuuuguuga auuuggcuuu gagguucacu uauacucuuu    180

ucgacaucaa agcuugcuua aaaauguuuu caaguugauu uuuagggacu uuuauacuug    240

agagcaauuu ggugguuugc uaguauuucc aaaccauauu gcuuaauaaa auacuagaua    300

agcuuguaga agcuuauagu auuauuuuua ggacgcgggu ucaauucccg ccaucuccac    360

ca                                                                   362
```

<210> SEQ ID NO 139
<211> LENGTH: 364
<212> TYPE: RNA
<213> ORGANISM: Borrelia garinii

<400> SEQUENCE: 139

```
ggggcugauu cuggauucga cugaaaaugc gaauauugua aguugcaggc agagggaauc     60

ucuuaaaacu ucuaaaauaa augcaaaaaa uaauaacuuu acaagcucaa accuuguaau    120

ggcugcuuaa guuagcaggg aguuucguug aauuuggcuu ugagguucac uuauacucuu    180

uucgauaucg aagcuugcuu aaaaauguuu ucaaguuaau uuuuagggac uuuuguacuu    240

gagagcaauu uggcgguuug cuaguauuuc caaaccauau ugcuuaagua aaaugcuaga    300

uaagcuugua gaagcuuaua auauuguuuu uaggacgcgg guucaauucc cgccaucucc    360

acca                                                                 364
```

<210> SEQ ID NO 140
<211> LENGTH: 363
<212> TYPE: RNA
<213> ORGANISM: Borrelia afzelii

<400> SEQUENCE: 140

```
ggggcugauu cuggauucga cugaaaaugc uaauauugua aguugcaagc agagggaauc     60

ucuuaaaacu ucuaaaauaa augcaaaaaa uaauaacuuu acaaguucaa accuuguaau    120

ggcugcuuaa guuagcagag aguuuuguug aauuuggcuu ugagauucac uuauacucuu    180

uuagacaucg aagcuugcuu aaaaauguuu ucaaguugau uuuuagggac uuuuauacuu    240

gagagcaauu uggcgguuug cuaguauuuc caaaccauau ugcuuaguaa aauacuagau    300

aagcuuguag aagcuuauag uauuguuuuu aggacgcggg uucaauuccc gccaucucca    360

cca                                                                  363
```

<210> SEQ ID NO 141
<211> LENGTH: 363
<212> TYPE: RNA
<213> ORGANISM: Borrelia crocidurae

<400> SEQUENCE: 141

```
ggggcugauu cuggauucga cuaagaacuu uaguagcaua aauggcaagc agagugaauc     60

ucuuaaaacu ucuuuaauaa augcaaaaaa uaauaacuuu acaaguucag aucuuguaau    120

ggcugcuuaa uuuagcagag aguuuuguug gauuuugcuu ugagguucaa cuuauacucu    180

uuaagacauc aaaguaugcc uaaaaauguu ucaaguugau uuuuagggac cuuuaaacuu    240

gagaguaauu uggugguuug cuuguuuucc aagccuuauu gcuuuuucua aaaauuagcu    300

aagcuuguag auauuuauga uauuauuuuu uggacgcggg uucaauuccc gccaucucca    360

cca                                                                  363
```

<210> SEQ ID NO 142
<211> LENGTH: 365
<212> TYPE: RNA

<213> ORGANISM: Borrelia hermsii

<400> SEQUENCE: 142
ggggcugauu cuggauucga cuaaaaacuu uaguagcaua aauugcaagc agagggaauc 60
ucuuaaaacu ucuuuaauaa augcaagaaa uaauaacuuu acaaguucaa aucuuguaau 120
ggcugcuuaa auuagcagag aguucugcug gauuuugcuu ugagguucag cuuauacucu 180
uuuaagacau caaagcuugc uuaaaaauau uucaaguuga uuuuuaggga cuuuuaaauu 240
ugagaguaau uuggcgguuu gcuaguuuuu ccaaaccuua uuacuuaaag aaaacacuag 300
cuaagcuugu agauauuuau gauauuauuu uuaggacgcg gguucaauuc ccgccaucuc 360
cacca 365

<210> SEQ ID NO 143
<211> LENGTH: 330
<212> TYPE: RNA
<213> ORGANISM: Alcaligenes faecalis
<400> SEQUENCE: 143 cggggggucaa gaagcagcac agggcguguc gagcaccagu acgcucguaa auccacugga 60
aaacuauaaa cgccaacgac gagcguuucg cucuagccgc uuaaggcugg gccacugcac 120
uaauuugucu uuggguuagg uagggcaacc uacagcagug uuauuuacaa agaaucgaau 180
cggucugcgc cacgaagucc gguucuaaaa cuuaguggau cgccaaggaa aggccuguca 240
auuggcauag uccaagguua aaacuuaaaa uuaauugacu acacauguag aacugucugu 300
ggacggcuug cggacggggg uucgauuccc 330

<210> SEQ ID NO 144
<211> LENGTH: 340
<212> TYPE: RNA
<213> ORGANISM: Alcaligenes eutrophus
<400> SEQUENCE: 144 cgugggguuac aaagcagugg agggcauacc gaggacccgu caccucguua aucaauggga 60
augcaauaac ugcuaacgac gaacguuacg cacuggccgc uuaauugcgg ccguccucgc 120
acuggcucgc ugacgggcua gggucgcaag accacgcgag gucauuuacg ucagauaagc 180
uccggaaggg ucacgaagcc ggggacgaaa accuagugac ucgccgucgu agagcguguu 240
cguccgcgau gcgccgguua aaucaaauga cagaacuaag uauguagaac ucucugugga 300
gggcuuacgg acgcggguuc gauucccgcc ggcuccacca 340

<210> SEQ ID NO 145
<211> LENGTH: 326
<212> TYPE: RNA
<213> ORGANISM: Ralstonia pickettii
<400> SEQUENCE: 145 cgggggguugc gaagcagcgg agggcauacc gaggacccgu caccucguua aucaauggga 60
augcaauaac ugcuaacgac gaacguuacg cacuggcagc cuaagggccg ccguccucgc 120
acuggcucgc ugacgggcua gggucgcaag accagcgagg ucauuuacgu cagauaagcu 180
uuaggugagu cacgggccua gagacgaaaa cuuagugaau cgccgucgua gagcguguuc 240
guccgcgaug cggcgguuaa aucaaaugac agaacuaagu auguagaacu cucuguggag 300
ggcuugcgga cgcggguucg auuccc 326

<210> SEQ ID NO 146

<211> LENGTH: 363
<212> TYPE: RNA
<213> ORGANISM: Neisseria gonorrhoeae

<400> SEQUENCE: 146
gggggcgacc uugguuucga cgggggguugc gaagcagaug cgggcauacc ggggucucag 60
auucccguaa aacacugaau ucaaauaguc gcaaacgacg aaacuuacgc uuuagccgcu 120
uaaggcuagc cguugcagca gucggucaau gggcugugug gugaaagcca ccgcaacguc 180
aucuuacauu gacugguuuc cagccggguu acuuggcagg aaauaaagacu uaagguaacu 240 gguuuccaaa aggccuguug gucggcauga uggaaauaag auuuucaaau agacacaacu 300
aaguauguag aacgcuuugu agaggacuuu cggacggggg uucgauuccc cccgccucca 360
cca 363

<210> SEQ ID NO 147
<211> LENGTH: 363
<212> TYPE: RNA
<213> ORGANISM: Neisseria meningitidis

<400> SEQUENCE: 147
gggggcgacc uugguuucga cgggggguugc gaagcagaug cgggcauacc ggggucucag 60
auucccguaa aacacugaau ucaaauaguc gcaaacgacg aaacuuacgc uuuagccgcu 120
uaaggcuagc cguugcagca gucggucaau gggcugugug gcgaaagcca ccgcaacguc 180
aucuuacauu gacugguuuc cugccggguu auuuggcagg aaaugagauu uaagguaacu 240
gguuuccaaa aggccuguug gucggcauga uggaaauaag auuuucaaau agacacaacu 300
aaguauguag aacgcuuugu agaggacuuu cggacggggg uucgauuccc cccgccucca 360
cca 363

<210> SEQ ID NO 148
<211> LENGTH: 333
<212> TYPE: RNA
<213> ORGANISM: Chromobacterium violaceum

<400> SEQUENCE: 148 cgggggguugc gaagcagaug agggcauacc gggauuucag ucacccccgua aaacgcugaa 60 uuuauauagu cgcaaacgac gaaacuuacg cucuggcagc cuaacggccg gccagacacu 120
acaacgguuc gcagaugggc cgggggcguc aaaacccugu agugucacuc uacaucugcu 180
agugcuguuc cggguuacuu gguucagugc gaaauaauag guaacucgcc aaaguccagc 240
cuguccgucg gcguggcaga gguuaaaucc aaaugacacg acuaaguaug uagaacucac 300
uguagaggac uuucggacgc ggguucaacu ccc 333

<210> SEQ ID NO 149
<211> LENGTH: 330
<212> TYPE: RNA
<213> ORGANISM: Nitrosomonas cryotolerans

<400> SEQUENCE: 149 cgugggguugc aaagcagcgc agggcauacc gaggaccaga auaccucgua aauacaucug 60
gaaaaaaaua gucgcaaacg acgaaaacua cgcuuuagcc gcuuaauacg gcuagccucu 120
gcaccgaugg gccuuaacgu cgggucuggc aacagacagc agagucauua gcaaggaucg 180
cguucuguag ggucacuuua cagaacguua aacaauaggu gacucgccug ccaucagccc 240
gccagcuggc gguugucagg uuaaauuaaa gagcauggcu aaguauguag aacugucugu 300
agaggacuug cggacgcggg uucaacuccc 330

<210> SEQ ID NO 150
<211> LENGTH: 331
<212> TYPE: RNA
<213> ORGANISM: Methylobacillus glycogenes

<400> SEQUENCE: 150 cgggggguugc aaagcagcgc agggcauacc gaggccuagu caccucguaa auaaacuaga 60
acaaguauag ucgcaaacga cgaaacuuac gcucuagccg cuuaaucccg gcuggacgcu 120
gcaccgaagg gccucucggu cggguggggu aacccacagc agcgucauua agagaggauc 180
gugcgauauu ggguuacuua auaucguauu aaauccaagg uaacucgccu gcuguuugcu 240
ugcucguugg ugagcaucag guuaaaucaa acaacacagc uaaguaugua gaacugucug 300
uggagggcuu gcggacgggg guucgauucc c 331

<210> SEQ ID NO 151
<211> LENGTH: 375
<212> TYPE: RNA
<213> ORGANISM: Pseudomonas testosteroni

<400> SEQUENCE: 151
ggggccgauu cuggauucga cgugggguucg ggaccggugc ggugcauguc gagcuugagu 60
gacgcucgua aaucuccauu caaaaaacua acugcaaacg acgaacguuu cgcacucgcc 120
gcuuaauccg gugagccuug caacagcacg cuagugggcu gggcaagggg guagcaauac 180
cucccggcug caagggaauu uucauuagcu ggcuggauac cgggcuucuu gguauuuggc 240
gagauuuuag gaagcuggcu acccaagcag cgugugccug cgggguuugg guggcgagau 300
uuaaaacaga gcacuaaaca uguagaucug uccggcgaag gcuuacggac gcggguucaa 360
uucccgccgg cucca 375

<210> SEQ ID NO 152
<211> LENGTH: 353
<212> TYPE: RNA
<213> ORGANISM: Variovorax paradoxus

<400> SEQUENCE: 152 cgugggguucg gagucgcagc ggggcauguc gagcugaaug cgcucguaaa acagauucaa 60
acaaacuaac ugcaaacgac gaacguuucg cacucgcugc uuaauugcca gugagccuug 120
caacaguugg ccgaugggcu gggcaagggg gucuggagca auccugaccu cccggcugca 180
aggauaacua caugggcugg cuccgauccg gguaccuugg gucggggcga gaaaauaggg 240
uacuggcguc cgguuuagcg ugugacugcg cgacuccgga agcgagacuc aaaacagauc 300
acuaaacaug uagaacugcg cgaugaaggc uugcggacgg ggguucaacu ccc 353

<210> SEQ ID NO 153
<211> LENGTH: 345
<212> TYPE: RNA
<213> ORGANISM: Hydrogenophaga palleroni

<400> SEQUENCE: 153 cgugggguucg gacgcgcagc agggcauguc gagguucugu caccucguaa aucagcagaa 60
aaaaaccaac ugcaaacgac gaacguuucg cacucgccgc uuaaacaccg gugagccuug 120
caacagcagg ccgaugggcu gggcaagggg gucgcaagac cucccggcug caagguaauu 180
uacaucggcu gguucugcgu cgggcaccuu ggcgcaggau gagauucaag gaugcuggcu 240
ucccguuuag cgugccacug cgcgacucgg gcggcgagac ccaaaucaga cggcuacaca 300
uguagaacug cucgaaaaag gcuugcggac gggguucaa cuccc 345

<210> SEQ ID NO 154
<211> LENGTH: 387
<212> TYPE: RNA
<213> ORGANISM: Bordetella pertussis

<400> SEQUENCE: 154
ggggccgauc cggauucgac gugggucaug aaacagcuca gggcaugccg agcaccagua 60
agcucguuaa uccacuggaa cacuacaaac gccaacgacg agcgucucgc ucucgccgcu 120
uaagcgguga gccgcugcac ugaucugucc uugggucagg cgggggaagg caacuuccca 180
gggggcaacc ccgaaccgca gcagcgacau ucacaaggaa ucggccaccg cuggggucac 240
acggcguugg uuuaaauuac gugaaucgcc cugguccggc ccgucgaucg gcuaagucca 300
ggguuaaauc caaauagauc gacuaagcau guagaacugg uugcggaggg cuugcggacg 360
gggguucaau uccccccggc uccacca 387

<210> SEQ ID NO 155
<211> LENGTH: 323
<212> TYPE: RNA
<213> ORGANISM: Legionella pneumophila

<400> SEQUENCE: 155 cgugggguugc aaaaccggaa gugcaugccg agaaggagau cucucguaaa uaagacucaa 60
uuaaauauaa augcaaacga ugaaaacuuu gcuggugggg aagcuaucgc ugccuaauaa 120
gcacuuuagu uaaaccauca cuguguacug gccaauaaac ccaguauccc guucgaccga 180
gcccgcuuau cgguaucgaa ucaacgguca uaagagauaa gcuagcgucc uaaucuaucc 240
cggguuaugg cgcgaaacuc agggaaucgc uguguaucau ccugcccguc ggaggagcca 300
caguuaaauu caaaagacaa ggc 323

<210> SEQ ID NO 156
<211> LENGTH: 315
<212> TYPE: RNA
<213> ORGANISM: Chromatium vinosum

<400> SEQUENCE: 156
cgugggucgc gaaaccuaag gugcaugccg aggugcgguu gaccucguaa aacccuccgc 60
aaacuuauag uugccaacga cgacaacuac gcucucgcug cuuaauccca gcgggccucu 120
gaccgucacu ugccuguggg cggcggauuc caggguaac cucacacagg aucgugguga 180
cgggaguccg gaccugaucc acuaaaaccu aacggaaucg ccgacugauc gcccugcccu 240
ucgggcggca gaaggcuaaa aacaauagag ugggcuaagc auguaggacc gagggcagag 300
ggcuugcgga cgcgg 315

<210> SEQ ID NO 157
<211> LENGTH: 318
<212> TYPE: RNA
<213> ORGANISM: Dichelobacter nodosus

<400> SEQUENCE: 157
cucgaggugc augucgagaa ugagagaauc ucguuaaaua cuuucaaaac uuauaguugc 60
aaacgacgac aacuacgcuu uagcggcuua auucccgcuu ucgcuuaccu agauuugucu 120 gugguuuac cguaagcgac auuaacacag aaucgcuggu uaacgcgucc gcuguuaauc 180
gguuaaauua agcggaaucg cuuguaaaau gccugagcgu uggcuguuua ugaguuaaac 240
cuaauuaacu gcucuaaaca uguaguacca aaaguuaagg auucgcggac gggggguucaa 300 aucccccgc cuccacca 318

<210> SEQ ID NO 158
<211> LENGTH: 354
<212> TYPE: RNA
<213> ORGANISM: Pseudomonas aeruginosa

<400> SEQUENCE: 158
ggggccgauu aggauucgac gccgguaaca aaacuugagg ggcaugccga gcugguagca 60
gaacucguaa auucgcugcu gcaaacuuau aguugccaac gacgacaacu acgcucuagc 120
ugcuuaaugc ggcuagacag ucgcuagggg augccuguaa acccgaaacg acugucagau 180
agaacaggau cgccgccaag uucgcuguag acguaacggc uaaaacucau acagcucgcu 240
ccaagcaccc ugccacucgg gcggcgcgga guuaacucag uagagcuggc uaagcaugua 300
gaaccgauag cggagagcug gcggacgggg guucaaaucc ccccggcucc acca 354

<210> SEQ ID NO 159
<211> LENGTH: 350
<212> TYPE: RNA
<213> ORGANISM: Pseudomonas fluorescens

<400> SEQUENCE: 159
cgccgguugc gaaccuuuag gugcaugccg aguugguaac agaacucgua aauccacugu 60
ugcaacuuuc uuaguugcca augacgaaac cuacggggaa uacgcucucg cugcguaagc 120
agccuuagcc cuucccuccu gguaccuucg gguccagcaa ucaucagggg augucuguaa 180
acccaaagug auugucauau agaacagaau cgccgugcag uacguugugg acgaagcggc 240
uaaaacuuac acaacucgcc caaagcaccc ugcccgucgg gucgcugagg guuaacuuaa 300
uagacacggc uacgcaugua guaccgacag cagaguacug gcggacgggg 350

<210> SEQ ID NO 160
<211> LENGTH: 323
<212> TYPE: RNA
<213> ORGANISM: Marinobacter hydrocarbonoclasticus

<400> SEQUENCE: 160
cgccggugac gaacccuugg gugcaugccg agauggcagc gaaucucgua aauccaaagc 60
ugcaacguaa uagucgcaaa cgacgaaaac uacgcacugg cggcguaagc cguuccaguc 120
guccuggcug aggcgccuau aacucaguag caacauccca ggacgucauc gcuuauaggc 180
ugcuccguuc accagagcuc acugguguuc ggcuaagauu aaagagcucg ccucuugcac 240
ccugaccuuc gggucgcuug agguuaaauc aauagaagga cacuaagcau guagaccuca 300
aggccuagug cuggcggacg cgg 323

<210> SEQ ID NO 161
<211> LENGTH: 355
<212> TYPE: RNA
<213> ORGANISM: Shewanella putrefaciens

<400> SEQUENCE: 161
gggggcgauu cuggauucga caggauucac gaaacccugg gagcaugccg aggggcgguu 60
ggccucguaa aaagccgcaa aguuauaguu gcaaacgacg auaacuacgc ucuagccgcu 120
uaaugccgcu agccaucuac cacacgcuuu gcacaugggc aguggauuug auggucaucu 180
cacaucgugc uagcgaggga acccugucug ggggugaacc gcgaaacagu accggacuca 240
ccguguggga uccugucuuu cggaguucaa acgguuaaac aauagaaaga cuaagcaugu 300
agcgccuugg auguagguuu ucuggacgcg gguucaaguc ccgccgccuc cacca 355

<210> SEQ ID NO 162
<211> LENGTH: 314
<212> TYPE: RNA
<213> ORGANISM: Pseudoalteromonas haloplanktis

<400> SEQUENCE: 162
cggaauucaa gaagcccgag gugcaugucg aggugcgguu ugccucguaa aaaagccgca 60
auuuaaagua aucgcaaacg acgauaacua cucucuagca gcuuaggcug gcuagcgcuc 120
cuuccaugua uucuugugga cuggauuuug gagugucacc cuaacaccug aucgcgacgg 180
aaacccuggc cgggguugaa gcguuaaaac uaagcggccu cgccuuuauc uaccguguuu 240
guccgggauu uaaagguuaa uuaaaugaca auacuaaaca uguaguaccg acggucgagg 300
cuuuucggac gggg 314

<210> SEQ ID NO 163
<211> LENGTH: 316
<212> TYPE: RNA
<213> ORGANISM: Aeromonas salmonicida

<400> SEQUENCE: 163
caagauucac gaaacccaag gugcaugccg aggugcggua ggccucguua acaaaccgca 60
aaaaaauagu cgcaaacgac gaaaacuacg cacuagcagc uuaauaaccu gcauagagcc 120
cuucuacccu agcuugccug uguccuaggg aaucggaagg ucauccuuca caggaucgug 180
uggaaguccu gcucggggcg gaagcauuaa aaccaaucga gcuagucaau ucguggcgug 240
ucucuccgca gcggguuggc gaauguaaag agugacuaag cauguaguac cgaggaugua 300
guaauuuugg acgggg 316

<210> SEQ ID NO 164
<211> LENGTH: 363
<212> TYPE: RNA
<213> ORGANISM: Salmonella typhimurium

<400> SEQUENCE: 164
ggggcugauu cuggauucga cgggauuugc gaaacccaag gugcaugccg aggggcgguu 60
ggccucguaa aaagccgcaa aaaaauaguc gcaaacgacg aaaccuacgc uuuagcagcu 120
uaauaaccug cuuagagccc ucucucccua gccuccgcuc uuaggacggg gaucaagaga 180
ggucaaaccc aaaagagauc gcgcggaugc ccugccuggg guugaagcgu uaaaacgaau 240
caggcuaguc ugguaguggc guguccgucc gcaggugcca ggcgaaugua aagacugacu 300
aagcauguag uaccgaggau guaggaauuu cggacgcggg uucaacuccc gccagcucca 360
cca 363

<210> SEQ ID NO 165
<211> LENGTH: 363
<212> TYPE: RNA
<213> ORGANISM: Escherichia coli

<400> SEQUENCE: 165
ggggcugauu cuggauucga cgggauuugc gaaacccaag gugcaugccg aggggcgguu 60
ggccucguaa aaagccgcaa aaaauagucg caaacgacga aacuacgcu uuagcagcuu 120 aauaaccugc uuagagcccu cucucccuag ccuccgcucu uaggacgggg aucaagagag 180
gucaaaccca aaagagaucg cguggaagcc cugccugggg uugaagcguu aaaacuuaau 240
caggcuaguu uguuaguggc guguccgucc gcagcuggca agcgaaugua aagacugacu 300
aagcauguag uaccgaggau guaggaauuu cggacgcggg uucaacuccc gccagcucca 360
cca 363

<210> SEQ ID NO 166
<211> LENGTH: 364
<212> TYPE: RNA
<213> ORGANISM: Yersinia pestis

<400> SEQUENCE: 166
ggggcugauu cuggauucga cgggauucgc gaaacccaag gugcaugccg aggugcggug 60
gccucguaaa aaaccgcaaa aaaaauaguu gcaaacgacg aaaacuacgc acuagcagcu 120
uaauaaccug cuuagagccc ucucucccua gccuccgcuc uuaggacggg gaucaagaga 180
ggucaaaccu aaaagagcuc guguggaaac cuugccuggg guggaagcau uaaaacuaau 240
caggauaguu ugucaguagc guguccaucc gcagcuggcc ggcgaaugua augauuggac 300
uaagcaugua gugccgacgg uguaguaauu ucggacgggg guucaaaucc ccccagcucc 360
acca 364

<210> SEQ ID NO 167
<211> LENGTH: 367
<212> TYPE: RNA
<213> ORGANISM: Vibrio cholerae

<400> SEQUENCE: 167
ggggcugauu caggauucga cgggaauuuu gcagucugag gugcaugccg aggugcggua 60
ggccucguua acaaaccgca aaaaaauagu cgcaaacgac gaaaacuacg cacuagcagc 120
uuaauacccu gcucagagcc cuuccucccu agcuuccgcu uguaagacgg ggaaaucagg 180
aaggucaaac caaaucaagc uggcguggau ucccccaccu gagggaugaa gcgcgagauc 240
uaauucaggu uagccauucg uuagcguguc gguucgcagg cgguggugaa auuaaagauc 300
gacuaagcau guaguaccaa agaugaaugg uuuucggacg gggguucaac ucccccccagc 360 uccacca 367

<210> SEQ ID NO 168
<211> LENGTH: 366
<212> TYPE: RNA
<213> ORGANISM: Haemophilus influenzae

<400> SEQUENCE: 168
ggggcugauu cuggauucga cgggauuagc gaagcccaag gugcacgucg aggugcggua 60
ggccucguaa auaaaccgca aaaaaauacu cgcaaacgac gaacaauacg cuuuagcagc 120
uuaauaaccu gcauuuagcc uucgcgcucc agcuuccgcu cguaagacgg ggauaacgcg 180
gagucaaacc aaaacgagau cguguggaag ccaccguuug aggaucgaag cacuaaauug 240
aaucaaacua gcuuaaguuu agcgugucug uccgcaugcu uaagugaaau uaaagacgag 300
acuaaacgug uaguacugaa gguagaguaa uuucggacgg ggguucaacu ccccccagcu 360
ccacca 366

<210> SEQ ID NO 169
<211> LENGTH: 366
<212> TYPE: RNA

<213> ORGANISM: Haemophilus actinomycetemcomitans

<400> SEQUENCE: 169
ggggcugauu cuggauucga cgggauuagc gaagcccgaa gugcacgucg aggugcggua 60
ggccucguaa auaaaccgca aaaaaauagu cgcaaacgac gaacaauacg cuuuagcagc 120
uuaauaaccu gccuuuagcc uucgcucccc agcuuccgcu cguaagacgg ggauaaagcg 180
gagucaaacc aaaacgagau cguguggaag ccaccguuug aggaucgaag cauuaaauua 240
aaucaaagua gcuuaauugu cgcguguccg ucagcaggau uaagugaauu uaaagaccgg 300
acuaaacgug uagugcuaac ggcagaggaa uuucggacgg ggguucaacu ccccccagcu 360
ccacca 366

<210> SEQ ID NO 170
<211> LENGTH: 354
<212> TYPE: RNA
<213> ORGANISM: Desulfovibrio desulfuricans

<400> SEQUENCE: 170
cggggacgug gaagccguag cggcaggucg aggcgccgcu ggccucguaa aaagcggcac 60
aaaaguaauu gccaacaacg auuacgacua cgcuuacgcu gccuaauaac agcgaggcaa 120
ugaccguuua acggucgcgc cgaucagggc caugccugau aacccugauu cacuuaucag 180
gcuggcgaaa accggcucuc gccgggguuu uucgcgagga guuuaccggc gggauuccug 240
cguugugccu ggucaggggc caacagcgcg gugaaauaca uacuugaccu aaaccuguag 300
augcuucgug uggaauguuc ucggacgggg guucaaaucc ccccggcucc acca 354

<210> SEQ ID NO 171
<211> LENGTH: 366
<212> TYPE: RNA
<213> ORGANISM: Myxococcus xanthus

<400> SEQUENCE: 171
gggggcggaa aggauucgac gggggcauug aaguucgaga cgcgugccga gcuugucagg 60
uagcucguaa auucaacccg gcaaagacac aaaagccaac gacaacguug agcucgcgcu 120
ggcugccuaa aaacagccca uagugcgcgg ucccccgcc cucggccugu gggguuggga 180
cagaccguca uaaugcaggc uggcugccga gggugccugg acccgaggug gcgagaucuu 240
cccaggaccg gcucugagua ucccguccgu gggagccuca gggacguagc aaaucgcgga 300
cuacgcacgu agggucgaag agcggacggc uuucggacgc ggguucgauu cccgccgccu 360
ccacca 366

<210> SEQ ID NO 172
<211> LENGTH: 346
<212> TYPE: RNA
<213> ORGANISM: Bdellovibrio bacteriovirus

<400> SEQUENCE: 172
gggggcggaa aggauucgac gggggugcug aagcauaagg agcauaccgg ggcggaugag 60
gaccucguua aaaacgucca cuuuguaauu ggcaacgauu acgcacuugc agcuuaauua 120
agcagcacga ucaaccuugu gguggguuccg cacuuggauu gaucgucauu uagggaccuc 180
ggcguguugg guuuucucca gcagacaugc uuaaauuuac ugggggagag gucuuaggga 240

-continued uuuugucugu ggaagcccga ggaccaaucu aaaacacuga cuaaguaugu agcgccuuau 300
cguggaucau uugcggacgg ggguucgauu cccgccgccu ccacca 346

<210> SEQ ID NO 173
<211> LENGTH: 386
<212> TYPE: RNA
<213> ORGANISM: Helicobacter pylori

<400> SEQUENCE: 173
ggggcugacu uggauuucga cagauuucuu gucgcacaga uagcaugcca agcgcugcuu 60
guaaaacagc aacaaaaaua acuguaaaca acacagauua cgcuccagcu uacgcuaaag 120
cugcgugagu uaaucuccuu uuggagcugg acugauuaga auuucuagcg uuuuaaucgc 180
uccauaaccu uaagcuagac gcuuuuaaaa ggugguucgc cuuuuaaacu aagaaacaag 240
aacucuugaa acuaucucaa gguuuuagaa aguuggacca gagcuaguuu uaaggcuaaa 300
aaaccaacca auuuucuaag cauuguagaa guuuguguuu agggcaagau uuuuggacug 360
ggguucgauu ccccacagcu ccacca 386

<210> SEQ ID NO 174
<211> LENGTH: 359
<212> TYPE: RNA
<213> ORGANISM: Campylobacter jejuni

<400> SEQUENCE: 174
gggagcgacu uggcuucgac aggaguaagu cugcuuagau ggcaugucgc uuugggcaaa 60
gcguaaaaag cccaaauaaa auuaaacgca aacaacguua aauucgcucc ugcuuacgcu 120
aaagcugcgu aaguucaguu gagccugaaa uuuaagucau acuaucuagc uuaauuuucg 180
gucauuuuug auaguguagc cuugcguuug acaagcguug aggugaaaua aagucuuagc 240
cuugcuuuug aguuuuggaa gaugagcgaa guagggugaa guagucaucu uugcuaagca 300
uguagagguc uuugugggau uauuuuugga caggggguucg auuccccucg cuuccacca 359

<210> SEQ ID NO 175
<211> LENGTH: 355
<212> TYPE: RNA
<213> ORGANISM: Sulfurospirillum deleyianum

<400> SEQUENCE: 175
caggaguagu uuuagcuuau ggcugcaugu cgggagugag ggucuuccgu uacacaaccu 60
ucaaacaaua acugcuaaca acaguaacua ucguccugcu uacgcgcuag cugcguaagu 120
uuaacaaaua auggacugcu cuccccuuug augcuaucuu aggaggucuu ggagaguauc 180
auagauuuga uagcuauauu acaugaacgc cuuuacaugu aaugaaguua aaggcucguu 240
uucguaguuu ucugauuguu guacgaagca aaauuaaaca cuaucaacaa uaucuaagca 300
uguagacguc auagguggcu auuuuuggac ugggguucaa cucccgccag cucca 355